US010233503B2

(12) United States Patent
Badosa

(10) Patent No.: US 10,233,503 B2
(45) Date of Patent: Mar. 19, 2019

(54) METHOD FOR THE IDENTIFICATION OF THE ORIGIN OF A CANCER OF UNKNOWN PRIMARY ORIGIN BY METHYLATION ANALYSIS

(75) Inventor: Manel Esteller Badosa, Barcelona (ES)

(73) Assignee: FUNDACIÓ INSTITUT D'INVESTIGACIÓ BIOMÈDICA DE BELLVITGE (IDIBELL), Barcelona (ES)

( * ) Notice: Subject to any disclaimer, the term of this patent is extended or adjusted under 35 U.S.C. 154(b) by 0 days.

(21) Appl. No.: 14/402,736

(22) PCT Filed: May 24, 2012

(86) PCT No.: PCT/EP2012/059687
§ 371 (c)(1),
(2), (4) Date: Nov. 21, 2014

(87) PCT Pub. No.: WO2013/174432
PCT Pub. Date: Nov. 28, 2013

(65) Prior Publication Data
US 2016/0017430 A1    Jan. 21, 2016

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/154* (2013.01)

(58) Field of Classification Search
None
See application file for complete search history.

(56) References Cited

U.S. PATENT DOCUMENTS

| 2001/0028333 | A1  | 10/2001 | Numazaki et al. |              |
|---|---|---|---|---|
| 2009/0191548 | A1* | 7/2009  | Berlin          | C12Q 1/6881 435/6.12 |
| 2010/0035242 | A1* | 2/2010  | Lofton-Day      | C12Q 1/6886 435/6.12 |
| 2011/0028333 | A1* | 2/2011  | Christensen     | C12Q 1/6869 506/8 |

FOREIGN PATENT DOCUMENTS

WO    2007/035676 A2    3/2007

OTHER PUBLICATIONS

Richter et al. BMC Cancer. 2009. 9: 455.*
Esteller et al Cancer Research. Apr. 2001. 61: 3225-3229.*
Greco et al Oncologist. 9(6): 644-652.*
Varadhachary et al J Clinical Oncology. Sep. 2008. 26(27): 4442.*
Neben et al Dtsch Arztebl Int. 2008. 105(43): 733-740.*
)Pavlidis et al Acta Oncologia. 2007. 46(5): 592-601.*

Crider K.S. et al., *Folate and DNA Methylation: A Review of Molecular Mechanisms and the Evidence for Folate's Role*, Adv. Nutr. 2012, 3: 21-28.
Fernandez, A., et al, Suppl. Material, 2011 Genome Research. vol. 22(2).
Houshdaran, S et al., DNA Methylation Profiles of Ovarian Epithelial Carcinoma Tumors and Cell Lines, PLOS ONE , 5 (2): pp. e9359-e9359, Feb. 2010.
Chung, W et al., "Identification of Novel Tumor Markers in Prostate, Colon and Breast Cancer by Unbiased Methylation Profiling," PLOS ONE, 3 (4):pp. e2079-e2079, Apr. 2008.
Irizarry, R.A. et al., "The human colon cancer methylome shows similar hypo- and hypermethylation at conserved tissue-specific CpG island Shores," Nature Genetics, 41 (2): 178-186, Feb. 2009.
Park, S.Y. et al., "Methylation Profiles of CpG Island Loci in Major Types of Human Cancers," Journal of Korean Medical Sciences, 22 (2): 311-317, 2007.
Kang, G.H. et al., "DNA methylation profiles of gastric carcinoma characterized by quantitative DNA methylation analysis," Laboratory Investigation, 88 (2): 161-170, 2008.
Tan, A.C. et al, "Characterizing DNA methylation patterns in pancreatic cancer genome," Molecular Oncology, 3 (2009), pp. 425-438.
Smith, J.F. et al., "Identification of DNA Methylation in 3' Genomic Regions that are Associated with Upregulation of Gene Expression in Colorectal Cancer," Epigenetics, 2 (3) (2007), pp. e1-e12.
Esteller, M. et al., "A Gene Hypermethylation Profile of Human Cancer," Cancer Research, 61: 3225-3229, Apr. 15, 2001.
Costello, J.F. et al., "Aberrant CpG—island methylation has non-random and tumour-type—specific patterns," Nature Genetics, 25:132-138, Feb. 2000.
Fernandez, A. et al., "A DNA methylation fingerprint of 1628 human samples," Genome Research, vol. 22 (2): 407-419 (2011).
Marina Bibikova et al, High-throughput DNA methylation profiling using universal bead arrays; Genome Research 16: 383-393 (2006).
J. Bridgewater et al, Gene Expression profiling may improve diagnosis in patients with carcinoma of unknown primary; British Journal of Cancer (2008) 98, 1425-1430.
Cindy A. Eads, et al, MethyLight: a high-throughput assay to measure DNA methylation; Nucleic Acids Research, 2000, vol. 28, No. 8, e32, i-viii.
Claudia Gebhard et al, Genome-Wide Profiling of CpG Methylation Identifies Novel Targets of Aberrant Hypermethylation in Myeloid Leukemia; Cancer Res, 2006; 66: (12); 6118-6128.
Mark L. Gonzalgo and Peter A. Jones, Rapid quantification of methylation differences at specific sites using methylation-sensitive single nucleotide primer extension (Ms-SNuPE); Nucleic Acids Research, 1997, vol. 25, No. 12, 2529-2531.

(Continued)

*Primary Examiner* — Carla J Myers
(74) *Attorney, Agent, or Firm* — Dinsmore & Shohl LLP

(57) ABSTRACT

The invention relates to methods and reagents for the identification of the origin of a carcinoma of unknown primary origin (CUP) based on the determination of the methylation profile in the genome of the CUP. The invention relates as well to methods for selecting a suitable therapy for a patient suffering a CUP as well as to methods for personalized medicine of patient suffering a CUP based on the use of a treatment which is adequate for the primary tumor from which the CUP is derived. The invention also relates to kits comprising reagents adequate for performing the above methods as well as to computer systems and programs which can be used for implementing the methods of the invention.

19 Claims, 4 Drawing Sheets

(56) References Cited

OTHER PUBLICATIONS

Figure 1A:
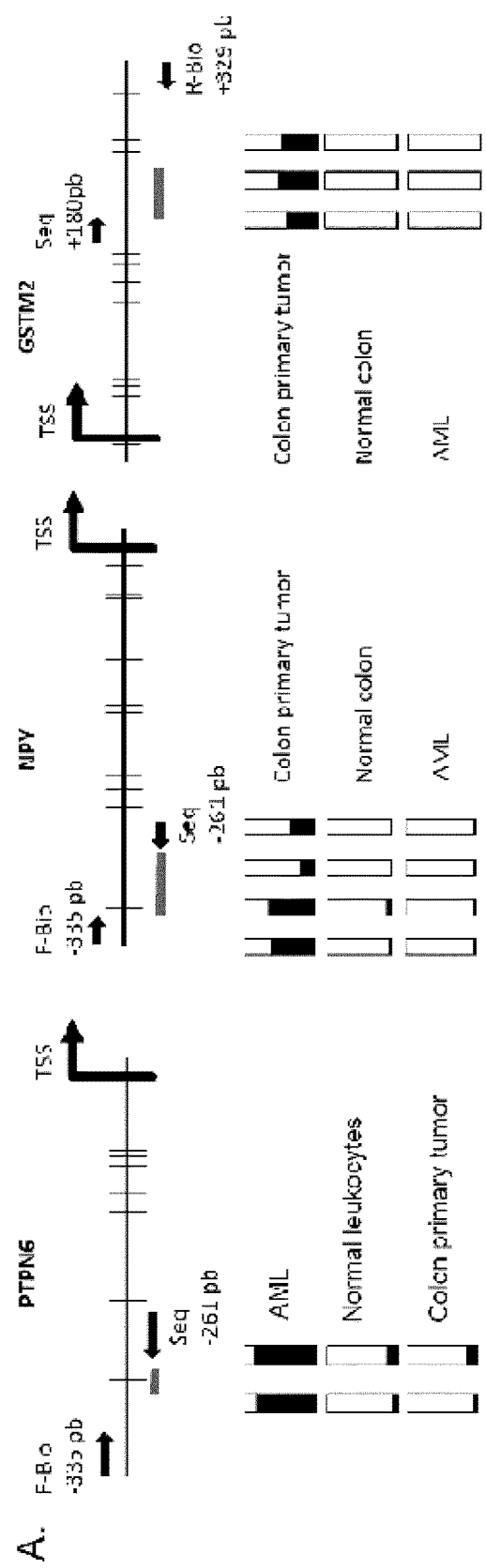

James G. Herman et al, Methylation-specific PCR: A novel PCR assay for methylation status of CpG islands; Proc. Natl. Acad. Sci, USA, vol. 93, 9821-9826, Sep. 1996.
Nicolas Jouve de La Barreda, Biomarcadores epigeneticos; Department of Cellular and Genetic Biology; University of Alcala; 87-112, 2010.
Seog-Yun Park et al, Methylation Profiles of CpG Island Loci in Major Types of Human Cancers; J Korean Med Sci 2007; 22:311-7.
Tibor A. Rauch et al, High-resolution mapping of DNA hypermethylation and hypomethylation in lung cancer; PNAS, Jan. 8, 2008, vol. 105, No. 1, 252-257.
Ramin Sadri and Peter J. Hornsby, Rapid Analysis of DNA methylation using new restriction enzyme sites created by bisulfate modification; Nucleic Acids Research, 1996, vol. 24, No. 24, 5058-5059.
Joseph Sambrook and Michael R. Green, Molecular Cloning, a Laboratory Manual, Fourth Edition, vol. 1, 2012.
Masahiko Shiraishi et al, Isolation of DNA fragments associated with methylated CpG islands in human adenocarcinomas of the lung using a methylated DNA binding column and denaturing gradient gel electrophoresis; Proc. Natl. Acad. Sci. USA, vol. 96, 2913-2918, Mar. 1999.
Minoru Toyota et al, Identification of Differentially Methylated Sequences in Colorectal Cancer by Methylated CpG Island Amplification; Cancer Research 5, 2307-2312, May 15, 1999.
Michael Weber et al, Chromosome-wide and promoter-specific analyses identify sites of differential DNA methylation in normal and transformed human cells; Nature Genetics, vol. 37, No. 8, Aug. 2005, 853-862.
Tomasz K. Wojdacz et al, Methylation-sensitive high-resolution melting; Nature Protocols, vol. 3, No. 12, 2008, 1903-1908.
Zhenggang Xiong and Peter W. Laird, Cobra: a sensitive and quantitative DNA methylation assay; Nucleic Acids Research, 1997, vol. 25, No. 12, 2532-2534.

* cited by examiner

METHOD FOR THE IDENTIFICATION OF THE ORIGIN OF A CANCER OF UNKNOWN PRIMARY ORIGIN BY METHYLATION ANALYSIS

BACKGROUND OF THE INVENTION

This invention provides materials, methods, algorithms, kits, etc. for identifying the origin of a carcinoma of unknown primary origin.

BACKGROUND OF THE INVENTION

Carcinoma of unknown primary (CUP) is a set of heterogeneous, biopsy-confirmed malignancies wherein metastatic disease presents without an identifiable primary tumor site or tissue of origin (ToO). This problem represents approximately 3-5 percent of all cancers, making it the seventh most common malignancy. The prognosis and therapeutic regimen of patients are dependent on the origin of the primary tumor, underscoring the need to identify the site of the primary tumor. A variety of methods are currently used to resolve this problem. Serum tumor Markers can be used for differential diagnosis. Although they lack adequate specificity, they can be used in combination with pathologic and clinical information. Immunohistochemical (IHC) methods can be used to identify tumor lineage but very few IHC Markers are 100 percent specific. Therefore, pathologists often use a panel of IHC Markers. Several studies have demonstrated accuracies of 66-88 percent using four to 14 IHC Markers. More expensive diagnostic workups include imaging methods such as chest x-ray, computed tomographic (CT) scans, and positron emission tomographic (PET) scans. Each of these methods can identify the primary in 30 to 50 percent of cases. Despite these sophisticated technologies, the ability to resolve CUP cases is only 20-30 percent ante mortem. A promising new approach lies in the ability of genome-wide gene expression profiling to identify the origin of tumors. In order for these expression profiling technologies to be useful in the clinical setting, two major obstacles must be overcome. First, since gene expression profiling was conducted entirely on primary tissues, gene marker candidates must be validated on metastatic tissues to confirm that their tissue specific expression is preserved in metastasis. Second, the gene expression profiling technology must be able to utilize formalin-fixed, paraffin-embedded (FFPE) tissue, since fixed tissue samples are the standard material in current practice. Formalin fixation results in degradation of the RNA so existing microarray protocols will not perform as reliably. Additionally, the profiling technology must be robust, reproducible, and easily accessible.

Accordingly, there is a need in the art for methods for the identification of the origin of a CUP which overcome the problems of the methods known in the prior art.

SUMMARY OF THE INVENTION

In a first aspect, the invention relates to a method for identifying the origin of a cancer of unknown primary origin (CUP) comprising the steps of:
 (i) determining the methylation profile in a selected region of a DNA isolated from said CUP and
 (ii) comparing the methylation profile of said selected region with the methylation profile of the same region in a DNA sample isolated from at least one primary tumor wherein a substantial identity between the methylation profile obtained in step (i) and the methylation profile of the primary tumor is indicative that the CUP derives from said primary tumor.

In a second aspect, the invention relates to a method for selecting a therapy for a cancer of unknown primary origin (CUP) comprising the steps of:
 (i) determining the methylation profile in a selected region of a DNA isolated from said CUP and
 (ii) comparing the methylation profile of said selected region with the methylation profile of the same region in a DNA sample isolated from at least one primary tumor wherein a substantial identity between the methylation profile obtained in (i) and the methylation profile of the primary tumor is indicative that the CUP is to be treated with a therapy which is suitable for said primary tumor.

In a third aspect, the invention relates to a method for treating a cancer of unknown primary origin (CUP) in a subject comprising the steps of:
 (i) determining the methylation profile in a selected region of a DNA isolated from said CUP,
 (ii) comparing the methylation profile of said selected region with the methylation profile of the same region in a DNA sample isolated from at least one primary tumor and
 (iii) treating the subject with a therapy adequate for said primary tumor wherein the methylation profile obtained in (i) shows a substantial identity with the methylation profile of the primary tumor.

In a further aspect, the invention relates to a kit for use in a method according to the invention comprising a plurality of primers or probes specific for determining a methylation status of a CpG site expressed by a CUP.

In yet another aspect, the invention relates to a computer system that is provided with means for implementing the methods according to the invention.

In another aspect, the invention relates to a computer program comprising a programming code to execute the steps of the methods according to the invention.

LEGENDS TO THE FIGURES

Figure 1B:
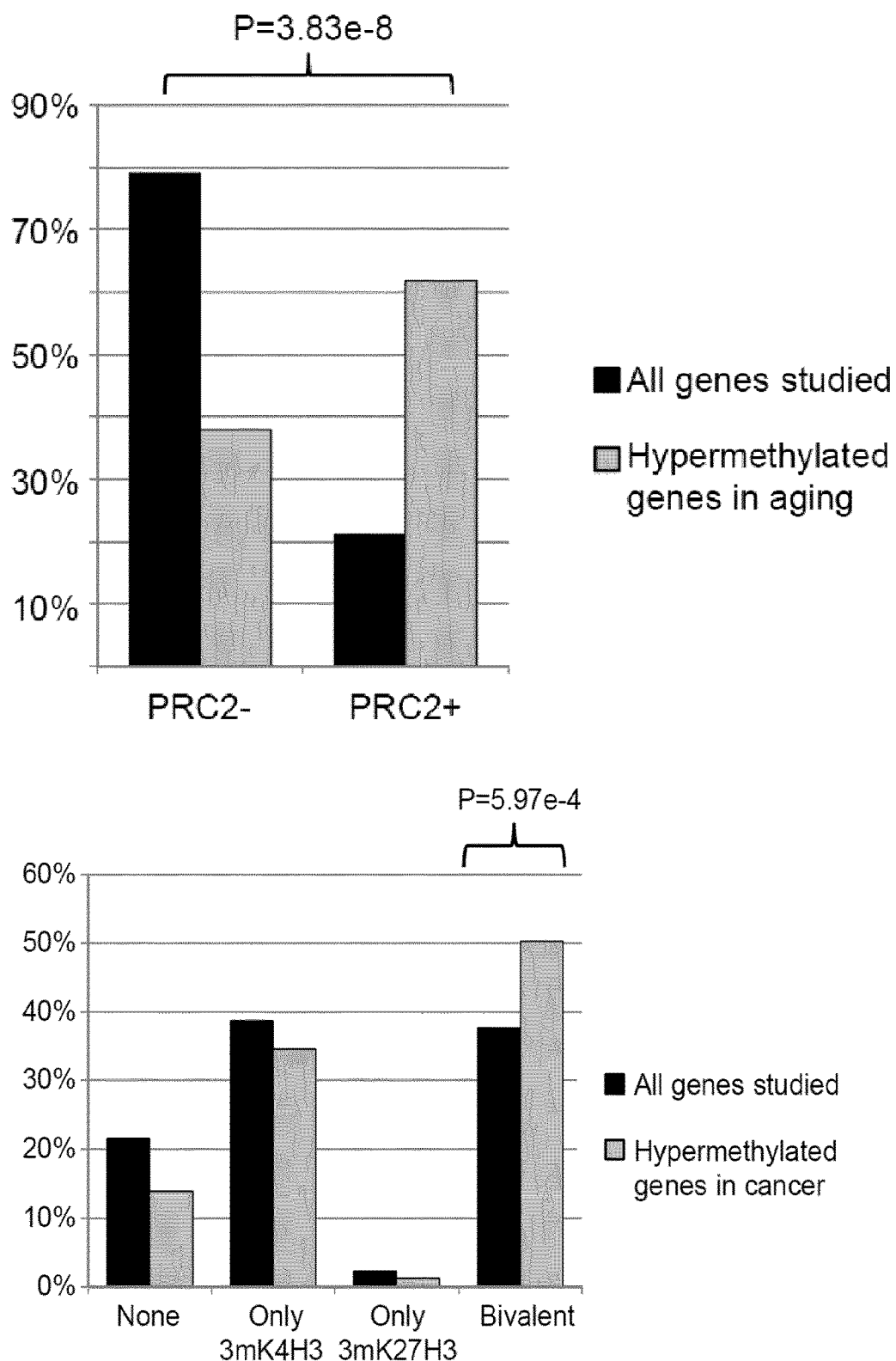
Figure 1C:
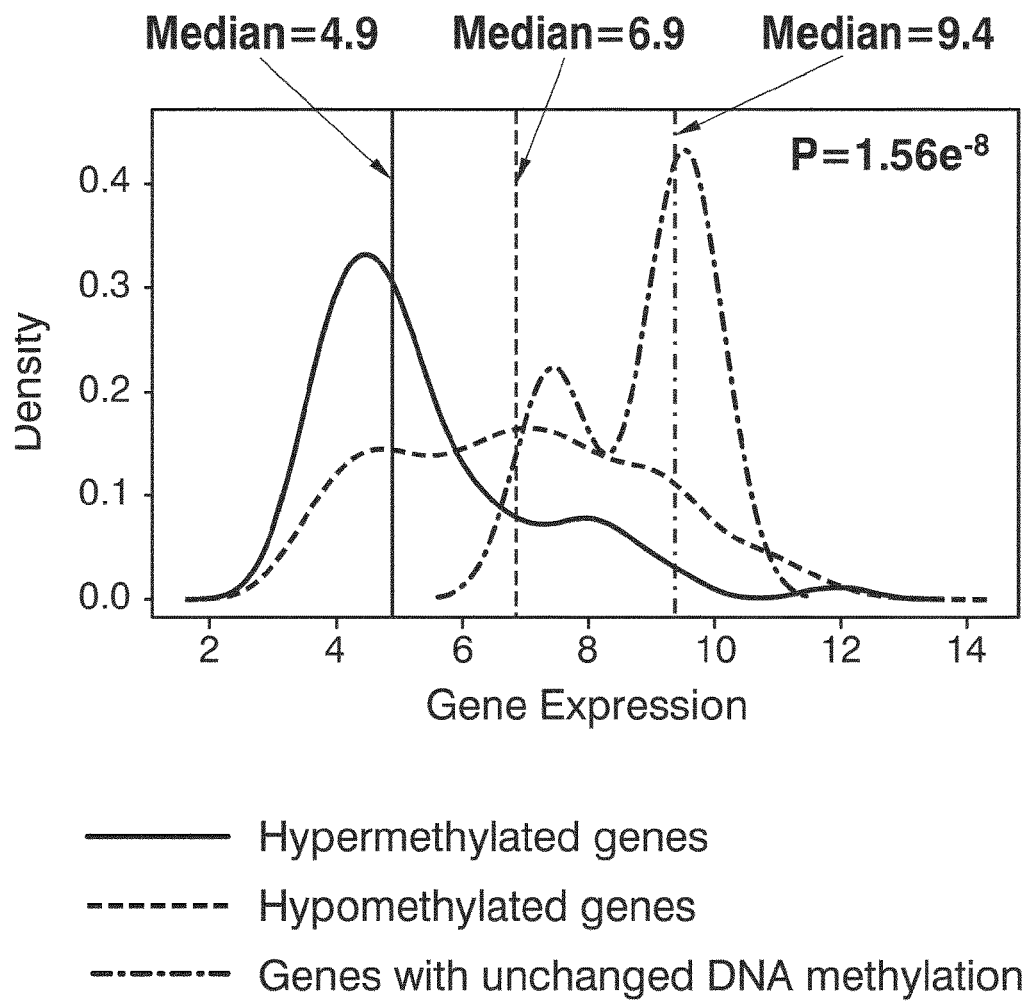

FIG. 1. A. Examples of cancer type-specific CpG methylation in particular genes further validated by pyrosequencing. The bars correspond to the analyzed CpG sites and black color represents the methylation percentage. B. Bar plot displaying the percentage of genes enriched for polycomb repressor complex 2 (Lee et al., 2006, Cell 125: 301-313) (left panel) or for 3mK4H3 and/or 3mK27H3 (Pan et al., 2007. Cell Stem Cell 1: 299-312.) (right panel) in embryonic stem cells. As compared to all the genes studied with the methylation array, the group of genes hypermethylated in cancer is significantly enriched for bivalent domains and targets of the polycomb complex. C. Density plot of microarray-based gene expression data in colon cancer patients. Hypermethylated genes (solid line) and hypomethylated genes (dashed line) show lower and higher expression levels, respectively, as compared to the rest of the genes studied with the methylation array (dashed-dotted line). The gene expression differences among the distinct methylation groups are statistically significant (Kruskal-Wallis test). Gene expression data are shown in a log 2 scale.

Figure 2:
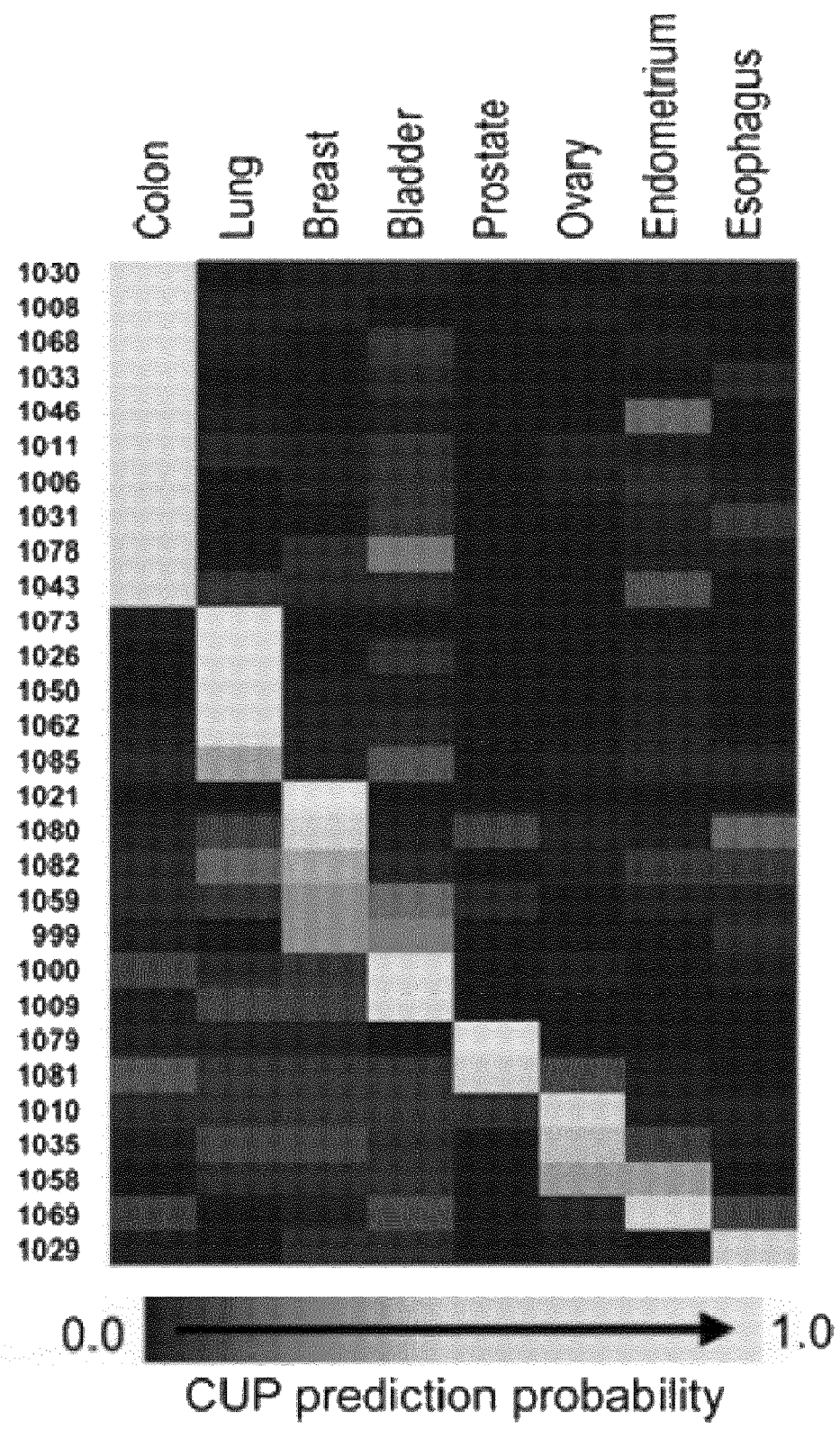

FIG. 2. Scenarios of DNA methylation changes in human tumorigenesis. CpG methylation prediction heatmap showing the CUP classification to a specific tumor type.

DETAILED DESCRIPTION OF THE INVENTION

The authors of the present invention have developed a method for the identification of the origin of a tumour of unknown primary origin based in the comparison of the DNA methylation fingerprint with the methylation fingerprint from a collection of primary tumors. This method can predict the tumor type of close to 100% of the provided CUP samples, i.e. as long as the tumor type is represented in the original collection of DNA methylation fingerprinted cancers, the method will provide the organ of origin. Moreover, the method has the advantage that, in addition to the identification of the origin of the CUP, it can also provide additional information on the tumor (e.g. receptor status and chemosensitivity prediction).

Identifying the primary origin of CUPs therefore provides knowledge of the survival chances of an individual having contracted cancer. It also provides insights on which sort of treatment should be offered to the individual having contracted cancer, thus providing an improved treatment response of the individual. Likewise, the individual may be spared treatment that is inefficient in treating the particular type of cancer and thus spare the individual severe side effects associated with treatment that may even not be suitable for the type of cancer. It is likely that for a person skilled in the art, in at least some instances, identification of the site of origin of a CUP correlates with prognosis or responsiveness. In such circumstances, it is possible that the same set of interaction partners can act as both a classification panel and a prognosis or predictive panel.

Definitions of Terms

The expression "cancer of unknown primary origin" or "CUP", as used herein, refers to a cancer which is found in one or more metastatic sites but for which the primary site is not known.

The terms "CG" or "CpG" can be used interchangeably and refer to regions of a DNA molecule where a cytosine nucleotide occurs next to a guanine nucleotide in the linear sequence of bases (linear strand) within the DNA molecule. Nucleotides forming a linear strand in a DNA molecule are linked through a phosphate. Therefore, a CG site is also referred to as a "CpG" site, a shorthand for cytosine-phosphate-guanine. The "CpG" notation is further used to distinguish the linear sequence of cytosine and guanine from the CG base-pairing of cytosine and guanine, where cytosine and guanine are located on opposite strands of a DNA molecule. Cytosines in CpG dinucleotides can be methylated to form 5-methylcytosine. In mammals, methylating the cytosine within a gene may turn the gene off. Enzymes that add a methyl group to a cytosine within a DNA molecule are referred to as DNA methyltransferases.

As used here, the term "CpG island" refers to a short DNA sequence rich in CpG dinucleotide and can be found in the 5' region of about one half of all human genes. The term "CpG site" refers to the CpG dinucleotide within the CpG islands. CpG islands are typically, but not always, between about 0.2 to about 1 kb in length.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "methylation" as used herein, refers to the covalent attachment of a methyl group at the C5-position of the nucleotide base cytosine within the CpG dinucleotides of gene regulatory region. The term "methylation state" or "methylation status" refers to the presence or absence of 5-methyl-cytosine ("5-mCyt") at one or a plurality of CpG dinucleotides within a DNA sequence. As used herein, the terms "methylation status" and "methylation state" are used interchangeably. A methylation site is a sequence of contiguous linked nucleotides that is recognized and methylated by a sequence-specific methylase. A methylase is an enzyme that methylates (i.e., covalently attaches a methyl group) one or more nucleotides at a methylation site.

As used herein, the term "methylation profile" refers to a set of data representing the methylation states of one or more loci within a molecule of DNA. The profile can indicate the methylation state of every base in an individual, can have information regarding a subset of the base pairs in a genome, or can have information regarding regional methylation density of each locus.

The term "methylation status" refers to the the presence or absence of 5-methyl-cytosine ("5-mCyt") at one or a plurality of CpG dinucleotides present on the DNA sequence of a target DNA methylation gene. As used herein, the terms "methylation status" and "methylation state" are used interchangeably. Methylation status at one or more particular CpG methylation sites (each having two CpG dinucleotide sequences) within a DNA sequence include "unmethylated", "fully-methylated" and "hemimethylated".

The term "primary tumor", as used herein, refers to a tumor that originated in the location or organ in which it is present and did not metastasize to that location from another location The term "primer" generally refers to an oligonucleotide that acts as a point of initiation of a template-directed synthesis using methods such as PCR (polymerase chain reaction) or LCR (ligase chain reaction) under appropriate conditions.

The term "nucleic acid probe" or "probe" refers to a labeled or unlabeled oligonucleotide capable of selectively hybridizing to a target or template nucleic acid under suitable conditions.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. In some embodiments, the term "treatment" can also mean prolonging survival as compared to expected survival if not receiving treatment. Those in need of treatment include those already diagnosed with a disease or condition, as well as those likely to develop a disease or condition due to genetic susceptibility or other factors which contribute to the disease or condition, such as a non-limiting example, weight, diet and health of a subject are factors which may contribute to a subject likely to develop diabetes mellitus. Those in need of treatment also include subjects in need of medical or surgical attention, care, or management. The subject is usually ill or injured, or at an increased risk of becoming ill relative to an average member of the population and in need of such attention, care, or management.

The term "computer-readable medium" may refer to any storage device used for storing data accessible by a computer, as well as any other means for providing access to data by a computer. Examples of a storage device-type computer-readable medium include: a magnetic hard disk; a floppy disk; an optical disk, such as a CD-ROM and a DVD; a magnetic tape; a memory chip.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "lymphoid neoplasia", as used herein, refers to a neoplasm arising from a malignant change in a B or T lymphocyte and includes, without limitation, any type of lymphoma. The two major types of lymphoma are Hodgkin's disease and non-Hodgkin lymphoma. Hodgkin disease is a relatively simple disease involving only four main types. In contrast, non-Hodgkin lymphoma (NHL) is a term applied to many different types of lymphatic cancer including the following subtypes; precursor B cell lymphoma, small lymphocytic lymphoma/chronic lymphocytic leukemia, marginal zone lymphomas (nodal marginal zone lymphoma, extranodal MALT, splenic), hairy cell leukemia, follicular lymphoma, mantle cell lymphoma, diffuse large B cell lymphoma, Burkitt's lymphoma, anaplastic large cell lymphoma, peripheral T cell lymphoma and mycosis fungoides. Other lymphoid neoplasms that are not strictly related to non-Hodgkin lymphoma but are covered by this invention includes acute lymphoblastic leukemia, lymphoplasmacytoid lymphoma, T-cell chronic lymphocytic leukemia/prolymphocytic leukemia, and any other cancers of lymphoid origin that are not easily classified.

The term "head and neck cancer", as used herein, refers to a group of biologically similar cancers that start in the upper aerodigestive tract, including the lip, oral cavity (mouth), nasal cavity (inside the nose), paranasal sinuses, pharynx, and larynx. 90% of head and neck cancers are squamous cell carcinomas (SCCHN),[1] originating from the mucosal lining (epithelium) of these regions. Head and neck squamous cell carcinomas (HNSCC's) make up the vast majority of head and neck cancers, and arise from mucosal surfaces throughout this anatomic region. These include tumors of the nasal cavities, paranasal sinuses, oral cavity, nasopharynx, oropharynx, hypopharynx, and larynx.

The term "pancreatic cancer" or "pancreas cancer" as used herein relates to cancer which is derived from pancreatic cells including but not limited to, adenocarcinomas, adenosquamous carcinomas, signet ring cell carcinomas, hepatoid carcinomas, colloid carcinomas, undifferentiated carcinomas, undifferentiated carcinomas with osteoclast-like giant cells and islet cell carcinomas.

The term "endometrial cancer", as used herein, refers to a malignancy that arises from the inner lining of the uterus (endometrium). The term refers to, but is not limited to endometrial carcinomas and endometrial adenocarcinomas. Endometrial cancers as used herein also include other well-known cell types such as papillary serous carcinoma, clear cell carcinoma, papillary endometrioid carcinoma, and mucinous carcinoma.

As used herein, "colon cancer," also called "colorectal cancer" or "bowel cancer," refers to a malignancy that arises in the large intestine (colon) or the rectum (end of the colon), and includes cancerous growths in the colon, rectum, and appendix, including adenocarcinoma.

As used herein, the term "prostate cancer" describes an uncontrolled (malignant) growth of cells originating from the prostate gland.

The term "glioma", as used herein, refers to a type of cancer that starts in the brain or spine and which arises from glial cells and/or its precursors including Ependymomas (gliomas derived from ependymal cells), astrocytomas (gliomas derived from astrocytes and which includes glioblastoma multiforme, oligodendrogliomas, (gliomas derived from oligodendrocytes) and mixed gliomas, such as oligoastrocytomas (derived from cells from different types of glia).

The term "ovarian cancer", as used herein, refers to a group of tumours that originate in the ovaries and includes, without limitation, serous ovarian cancer, non-invasive ovarian cancer, mixed phenotype ovarian cancer, mucinous ovarian cancer, endometrioid ovarian cancer, clear cell ovarian cancer, papillary serous ovarian cancer, Brenner cell, and undifferentiated adenocarcinoma.

The term "lung cancer", as used herein, refers to any uncontrolled cell growth in tissues of the lung, including but not limited to, small cell lung carcinoma, combined small cell lung carcinoma, non-small cell lung carcinoma, sarcomatoid carcinoma, salivary gland tumors, carcinoid tumor, adenosquamous carcinoma, pleuropulmonary blastoma and carcinoid tumor.

The term "bladder cancer", as used herein, refers to any of several types of malignant growths of the urinary bladder and includes, without limitation, transitional cell carcinoma, squamous cell carcinoma, adenocarcinoma, sarcoma and small cell carcinoma.

The term "melanoma" as used herein refers to any form of cancer that begins in melanocytes Melanoma includes, but is not limited to, the following subtypes: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, and metastatic melanoma The term breast cancer or malignant breast neoplasm is commonly used as the generic name for cancers originating from breast tissue, most commonly from the inner lining of milk ducts or the lobules that supply the ducts with milk. Depending on their receptor status as detected by immunohistochemistry, in particular on the presence or absence of estrogen receptor (ER), progesterone receptor (PR) and on the level of expression of HER2/neu (normal expression/under-expression vs over-expression), breast cancers may be divided into ER positive (ER+) breast cancer, ER negative (ER−) breast cancer, PR positive (PR+) breast cancer, PR negative (PR−) breast cancer, HER2 positive (HER2+) breast cancer (cancer over-expressing HER2), HER2 negative (HER2−) breast cancer (cancer expressing normal levels of HER2 or under-expressing HER2, or not expressing a detectable level of HER2), hormone receptor negative breast cancer, i.e. breast cancer with neither of estrogen nor progesterone receptors (abbreviated by ER−/PR− breast cancer); and triple negative breast cancer, i.e. breast cancer with neither of estrogen nor progesterone receptors and with normal expression/under-expression (or with the absence of detectable level of expression) of HER2 (abbreviated by ER−/PR−/HER2− breast cancer). Depending on their gene expression pattern, breast cancers may be divided into luminal subtype A breast cancer, luminal subtype B breast cancer, normal-like breast cancer, HER2+ breast cancer and basal-like breast cancer (Sorlie et al. (2001) Proc. Nat. Acad. Sci. 98:10869-10874). Luminal A and B subtypes are largely ER positive. In contrast, HER2+ breast cancers show an increased high expression of genes associated with the HER2 amplicon and normal-like breast cancers share molecular features of normal breast tissue.

As used herein, the term "myeloid neoplasms" refers to cancers of cells of the myeloid lineage, e.g., myeloid (myelocytic or myelogenous) leukemias derived from granulocytes (e.g., neutrophils, eosinophils, and basophils) or monocytes; for example, chronic myelocytic leukemia, acute myelocytic leukemia, chronic neutrophilic leukemia, chronic eosinophilic leukemia, and myelodyplastic syndromes.

The term "testicular cancer", as used herein, refers to a cancer that develops in the testicles. The term "testicular cancer" includes but is not limited to malignant cancer such as seminomas, nonseminomas, choriocarcinoma, embryonal carcinoma, immature teratoma, yolk sac tumors, Leydig and sertoli cell tumors, PNET, leiomyosarcoma, rhabdomyosarcoma, and mesothelioma The term "stomach tumor" or "stomach cancer" refers to any tumor or cancer of the stomach, including, e.g., adenocarcinomas (such as diffuse type and intestinal type), and less prevalent forms such as lymphomas, leiomyosarcomas, and squamous cell carcinomas.

Method for the Determination of the Origin of a Cancer of Unknown Primary Origin (CUP)

In a first aspect, the invention relates to a method for identifying the origin of a cancer of unknown primary origin (CUP) (hereinafter first method of the invention) comprising the steps of:
 (i) determining the methylation status of at least one CpG site in a DNA isolated from a sample containing cells from said CUP and
 (ii) comparing the methylation status of said at least one CpG site obtained in (i) with the methylation status of the same CpG site in a DNA sample isolated from at least one primary tumor
wherein a substantial identity between the methylation status obtained in (i) and the methylation status of the primary tumor is indicative that the CUP derives from said primary tumor.

In some embodiments, the methylation level is determined in a a CpG island or in a non-CpG island.

In a first step, the methylation profile of a selected region in a DNA isolated from said CUP is determined. The determination is carried out in a sample containing cells derived from the CUP. The biological sample can be virtually any biological sample, particularly a sample that contains RNA or DNA from the subject. The biological sample can be a tissue sample which contains about 1 to about 10,000,000, about 1000 to about 10,000,000, or about 1,000,000 to about 10,000,000 somatic cells. However, it is possible to obtain samples that contain smaller numbers of cells, even a single cell in embodiments that utilize an amplification protocol such as PCR. The sample need not contain any intact cells, so long as it contains sufficient biological material to assess methylation profile. The sample may be any suitable sample comprising cellular matter of the tumor. Suitable sample types include cell lines, histological slides, biopsies, paraffin-embedded tissue, body fluids, stool, colonic effluent, urine, blood plasma, blood serum, whole blood, isolated blood cells, cells isolated from the blood and all possible combinations thereof.

In a preferred embodiment, the sample is a CUP sample. The sample may be provided in histological slides, biopsies, paraffin-embedded tissue, frozen tissue, formalin fixed tissue, body fluids, stool, colonic effluent, urine, blood plasma, blood serum, whole blood, isolated blood cells, cells isolated from the blood and combinations thereof.

The genomic DNA is then isolated from the sample. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Wherein the sample DNA is not enclosed in a membrane (e.g. circulating DNA from a blood sample) methods standard in the art for the isolation and/or purification of DNA may be employed. Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. The person skilled in the art may also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

Once the nucleic acids have been extracted, the genomic double stranded DNA is used in the analysis, methylation analysis may be carried out by any means known in the art. A variety of methylation analysis procedures are known in the art and may be used to practice the invention. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes. The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al., 1996, Proc. Nat. Acad. Sci. USA, 93, 9821-9826; U.S. Pat. Nos. 5,786,146, 6,017,704, 6,200, 756, 6,265,171 (Herman and Baylin) U.S. Pat. Pub. No. 2010/0144836 (Van Engeland et al); which are hereby incorporated by reference in their entirety). Briefly, DNA is modified by sodium bisulfite converting unmethylated, but not methylated cytosines to uracil, and subsequently amplified with primers specific for methylated versus unmethylated DNA. MSP requires only small quantities of DNA, is sensitive to 0.1 percent methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes. The ColoSure™ test is a commercially available test for colon cancer based on the MSP technology and measurement of methylation of the vimentin gene (Itzkowitz et al, 2007, Clin Gastroenterol. Hepatol. 5(1), 111-117). Alternatively, one may use quantitative multiplexed methylation specific PCR (QM-PCR), as described by Fackler et al. Fackler et al, 2004, Cancer Res. 64(13) 4442-4452; or Fackler et al, 2006, Clin. Cancer Res. 12(11 Pt 1) 3306-3310.

In an embodiment, the methylation profile of selected CpG sites is determined using MethyLight and Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al), the contents of which are hereby incorporated by reference in their entirety). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both. The MethyLight assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase. The MethyLight technology is used for the commercially available tests for lung cancer (epi proLung BL Reflex Assay); colon cancer (epi proColon assay and mSEPT9 assay) (Epigenomics, Berlin, Germany) PCT Pub. No. WO 2003/064701 (Schweikhardt and Sledziewski), the contents of which is hereby incorporated by reference in its entirety.

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32, e10, the contents of which is hereby incorporated by reference in its entirety).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites. Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi), the contents of which are hereby incorporated by reference in their entirety). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

Alternatively, one may use 5-methyl cytidine antibodies to bind and precipitate methylated DNA. Antibodies are available from Abeam (Cambridge, Mass.), Diagenode (Sparta, N.J.) or Eurogentec (c/o AnaSpec, Fremont, Calif.). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918). 5.3.4. Methylation Specific Restriction Enzymatic Methods For example, there are methyl-sensitive enzymes that preferentially or substantially cleave or digest at their DNA recognition sequence if it is non-methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, Hpall, Hhal, Maell, BstUI and Acil. An enzyme that can be used is Hpall that cuts only the unmethylated sequence CCGG. Another enzyme that can be used is Hhal that cuts only the unmethylated sequence GCGC. Both enzymes are available from New England BioLabs®, Inc. Combinations of two or more methyl-sensitive enzymes that digest only unmethylated DNA can also be used. Suitable enzymes that digest only methylated DNA include, but are not limited to, Dpnl, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . Pu$^m$C(N$_{40-3000}$) Pu$^m$C . . . 3' (New England BioLabs, Inc., Beverly, Mass.). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

The MCA technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al.) the contents of which are hereby incorporated by reference in their entirety). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat. Prot. 3(12) 1903-1908; Balic et al, 2009 J. Mol. Diagn. 11 102-108; and US Pat. Pub. No. 2009/0155791 (Wojdacz et al), the contents of which are hereby incorporated by reference in their entirety). A variety of commercially available real time PCR machines have HRM systems including the Roche LightCycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined is using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al.) which is hereby incorporated by reference in its entirety. For methylation analysis, the assay can be adopted to detect bisulfite introduced methylation dependent C to T sequence changes. These methods are particularly useful for performing multiplexed amplification reactions and multiplexed primer extension reactions (e g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 117-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyrosequencing (WO 2009/049916 (Bayeyt et al). These references for these techniques are hereby incorporated by reference in their entirety.

Following reaction or separation of nucleic acid in a methylation specific manner, the nucleic acid may be subjected to sequence-based analysis. Furthermore, once it is determined that one particular melanoma genomic sequence is hypermethylated or hypomethylated compared to the benign counterpart, the amount of this genomic sequence can be determined. Subsequently, this amount can be compared to a standard control value and serve as an indication for the melanoma. In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits of the invention may use any nucleic acid amplification or detection methods known to one skilled in the art, such as those described in U.S. Pat. No. 5,525,462 (Takarada et al); U.S. Pat. No. 6,114,117 (Hepp et al); U.S. Pat. No. 6,127,120 (Graham et al); U.S. Pat. No. 6,344,317 (Urnovitz); U.S. Pat. No. 6,448,001 (Oku); U.S. Pat. No. 6,528,632 (Catanzariti et al); and PCT Pub. No. WO 2005/111209 (Nakajima et al); all of which are incorporated herein by reference in their entirety.

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicase amplification, rolling circle amplification, transcription amplification, self-sustained sequence replication, nucleic acid sequence-based amplification (NASBA), each of which provides sufficient amplification. Branched-DNA technology may also be used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and is thus not described in detail herein. For a review of PCR methods and protocols, see, e.g., Innis et al, eds., PCR Protocols, A Guide to Methods and Application, Academic Press, Inc., San Diego, Calif. 1990; U.S. Pat. No. 4,683,202 (Mullis); which are incorporated herein by reference in their entirety. PCR reagents and protocols are also available from commercial vendors, such as Roche Molecular Systems. PCR may be carried out as an automated process with a thermostable enzyme. In this process, the temperature of the reaction mixture is cycled through a denaturing region, a primer annealing region, and an extension reaction region automatically. Machines specifically adapted for this purpose are commercially available.

Amplified sequences may also be measured using invasive cleavage reactions such as the Invader® technology (Zou et al, 2010, Association of Clinical Chemistry (AACC) poster presentation on Jul. 28, 2010, "Sensitive Quantification of Methylated Markers with a Novel Methylation Specific Technology," available at www.exactsciences.com; and U.S. Pat. No. 7,011,944 (Prudent et al.) which are incorporated herein by reference in their entirety).

Suitable next generation sequencing technologies are widely available. Examples include the 454 Life Sciences platform (Roche, Branford, Conn.) (Margulies et al. 2005 Nature, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al, 2006, Genome Res. 16, 383-393; U.S. Pat. Nos. 6,306,597 and 7,598,035 (Macevicz); U.S. Pat. No. 7,232,656 (Balasubramanian et al.)); or DNA Sequencing by Ligation, SOLiD System (Applied Biosystems/Life Technologies; U.S. Pat. Nos. 6,797,470, 7,083,917, 7,166, 434, 7,320,865, 7,332,285, 7,364,858, and 7,429,453 (Barany et al); or the Helicos True Single Molecule DNA sequencing technology (Harris et al, 2008 Science, 320, 106-109; U.S. Pat. Nos. 7,037,687 and 7,645,596 (Williams et al); U.S. Pat. No. 7,169,560 (Lapidus et al); U.S. Pat. No. 7,769,400 (Harris)), the single molecule, real-time (SMRT™) technology of Pacific Biosciences, and sequencing (Soni and Meller, 2007, Clin. Chem. 53, 1996-2001) which are incorporated herein by reference in their entirety. These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, Nat. Prot. 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., 2003, J. Biotech. 102, 117-124). Such a system can be used to exponentially amplify amplification products generated by a process described herein, e.g., by ligating a heterologous nucleic acid to the first amplification product generated by a process described herein.

In some embodiments, the determination of the methylation profile in the first method of the invention comprises determining the methylation status of more than at least 1, 2, 3, 4, 5, 6, 7, 8, 9, 10, 15, 20, 25, 30, 35, 40, 50, 75, or 100, 150, 200, 250, 300, 400, 500, 750, or 1000 CpG sites within a DNA sample. In one aspect of this embodiment, the method of the invention is used to determine the methylation status of from 1 to 1000 CpG sites, 2 to 1000 CpG sites, 3 to 1000 CpG sites, 4 to 1000 CpG sites, 5 to 1000 CpG sites, 6 to 1000 CpG sites, 7 to 1000 CpG sites, 8 to 1000 CpG sites, 9 to 1000 CpG sites, or 10 to 1000 CpG sites.

In a second step, the first method of the invention comprises comparing the methylation profile of said selected region with the methylation profile of the same region in a DNA sample isolated from at least one primary tumor.

The primary tumor can be an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor. In some embodiments, the cancer comprises a gastrointestinal cancer, gastric cancer, hepatocellular carcinoma, liver cancer, gastrointestinal stromal tumor (GIST), esophageal cancer, pancreatic cancer or colorectal cancer.

In a preferred embodiment, the primary tumor is selected from the group consisting of a lymphoid neoplasia, head and neck cancer, pancreatic cancer, endometrial cancer, colon cancer, prostate cancer, glioma, ovarian cancer, lung cancer, bladder cancer, melanoma, breast cancer, a myeloid neoplasia, testicular cancer, stomach cancer.

In a preferred embodiment of the first method of the invention, the methylation profile is determined by determining the methylation status in one or more CpG sites as defined in Table 1A or in Table 1B and the resulting methylation profile is compared with the methylation profile in same CpG sites in a DNA sample from a lymphoid neoplasia. In the following tables, the CpG sites are defined using the GoldenGate code which can be seen as GENE_P/EXXX_R/F, wherein GENE is the gene name, P/E indicates whether the CpG site is present in the promoter or exon, XXX corresponds to the distance in base pair from the CpG site to the transcription initiation site as described in the database genome.ucsc.edu and R/F indicates that the site is present in the forward or reverse strand of the DNA molecule. The design of the GoldenGate was done using human genome version 36.1 (or its equivalent UCSC hg18).

TABLE 1A

List of CpG sites with specific differential hypermethylation and hypomethylation in lymphoid neoplasias (n: 200). CpG island associated (CGI): Yes (Y) or not (N).

| Lymphoid neoplasias hypermetylation (n: 200) | CGI | Lymphoid neoplasias hypomethylation (n: 54) | CGI |
|---|---|---|---|
| DBC1_P351_R | Y | DDR1_P332_R | N |
| NEFL_P209_R | Y | BLK_P14_F | N |
| HTR1B_P222_F | Y | LTA_P214_R | N |
| HS3ST2_E145_R | Y | NOTCH4_P938_F | N |
| IGSF4_P86_R | Y | RUNX3_P393_R | Y |
| DLK1_E227_R | Y | BLK_P668_R | N |
| SLC22A3_E122_R | Y | PADI4_P1011_R | N |
| ISL1_P379_F | Y | RUNX3_P247_F | Y |
| MYOD1_E156_F | Y | PLA2G2A_P528_F | N |
| DBC1_E204_F | Y | HLA-DOB_E432_R | N |
| IGFBP3_P423_R | Y | LCK_E28_F | Y |
| SOX1_P294_F | Y | DES_P1006_R | N |
| FAT_P279_R | Y | PMP22_P975_F | N |
| MOS_E60_R | Y | TMPRSS4_P552_F | N |
| SLIT2_P208_F | Y | RHOH_P953_R | N |
| HS3ST2_P171_F | Y | IL18BP_E285_F | N |
| PALM2-AKAP2_P420_R | Y | KLK11_P103_R | N |
| CFTR_P372_R | Y | RUNX3_E27_R | N |
| HTR1B_E232_R | Y | BGN_P333_R | N |
| RAB32_P493_R | Y | AOC3_P890_R | N |
| DIO3_P674_F | Y | LEFTY2_P561_F | N |
| NGFB_E353_F | Y | CCL3_E53_R | N |
| CHGA_E52_F | Y | IL12B_P1453_F | Y |
| IGF2_E134_R | Y | NOS2A_P288_R | N |
| SFRP1_P157_F | Y | NAT2_P11_F | N |
| SFRP1_E398_R | Y | E2F5_P516_R | Y |
| FGFR2_P460_R | Y | MPL_P657_F | N |
| PTGS2_P308_F | Y | PTHR1_P258_F | N |
| SEMA3C_E49_R | Y | PRSS1_E45_R | N |
| EYA4_P794_F | Y | PLA2G2A_E268_F | N |
| GATA6_P726_F | Y | CPA4_E20_F | N |
| CDH13_P88_F | Y | PI3_P1394_R | N |
| CDH13_E102_F | Y | TRIM29_P135_F | N |
| TFAP2C_E260_F | Y | EPHX1_E152_F | N |
| TUSC3_E29_R | Y | EPHX1_P1358_R | N |
| PITX2_E24_R | Y | DLC1_P695_F | N |
| MLF1_E243_F | Y | DSG1_P159_R | N |
| PLS3_E70_F | Y | SFTPB_P689_R | N |
| WNT2_P217_F | Y | IGF1_P933_F | N |
| FRZB_E186_R | Y | CLDN4_P1120_R | N |
| EYA4_E277_F | Y | IGF1_E394_F | N |
| HOXA9_E252_R | Y | HLA-DPB1_P540_F | N |
| ISL1_E87_R | Y | CSF1R_P73_F | N |
| HOXA9_P1141_R | Y | AIM2_E208_F | N |
| FZD9_E458_F | Y | IL1B_P829_F | N |
| ONECUT2_E96_F | Y | GRB7_P160_R | N |
| SOX17_P287_R | Y | MAGEC3_E307_F | N |
| ASCL2_P360_F | Y | AATK_E63_R | N |

TABLE 1A-continued

List of CpG sites with specific differential hypermethylation and hypomethylation in lymphoid neoplasias (n: 200). CpG island associated (CGI): Yes (Y) or not (N).

| Lymphoid neoplasias hypermetylation (n: 200) | CGI | Lymphoid neoplasias hypomethylation (n: 54) | CGI |
|---|---|---|---|
| FAT_P973_R | Y | MMP9_E88_R | N |
| KDR_E79_F | Y | KRT13_P676_F | N |
| CDH11_P354_R | Y | IAPP_E280_F | N |
| GABRB3_E42_F | Y | SMARCB1_P220_R | Y |
| HOXA11_P698_F | Y | IFNG_P188_F | N |
| DCC_P471_R | Y | KRT1_P798_R | N |
| DSC2_E90_F | Y | | |
| IMPACT_P234_R | Y | | |
| GALR1_E52_F | Y | | |
| ADAMTS12_E52_R | Y | | |
| TJP1_P390_F | Y | | |
| IGFBP3_E65_R | Y | | |
| SLC5A8_E60_R | Y | | |
| TIMP3_seq_7_S38_F | Y | | |
| PENK_P447_R | Y | | |
| KDR_P445_R | Y | | |
| ISL1_P554_F | Y | | |
| ADCYAP1_P398_F | Y | | |
| CDH11_P203_R | Y | | |
| CDH1_P52_R | Y | | |
| ETV1_P515_F | Y | | |
| EGFR_E295_R | Y | | |
| NTRK2_P10_F | Y | | |
| CTSL_P81_F | Y | | |
| SOX1_P1018_R | Y | | |
| SCGB3A1_E55_R | Y | | |
| RBP1_E158_F | Y | | |
| CALCA_E174_R | Y | | |
| HOXB13_P17_R | Y | | |
| ALOX12_E85_R | Y | | |
| FGFR2_P266_R | Y | | |
| DAPK1_P10_F | Y | | |
| RET_seq_54_S260_F | Y | | |
| NGFB_P13_F | Y | | |
| TJP1_P326_R | Y | | |
| PENK_E26_F | Y | | |
| ERBB4_P541_F | Y | | |
| TAL1_P594_F | Y | | |
| NTRK2_P395_R | Y | | |
| IPF1_P234_F | Y | | |
| FGF3_P171_R | Y | | |
| IHH_E186_F | Y | | |
| ASCL1_P747_F | Y | | |
| DES_E228_R | Y | | |
| DCC_P177_F | Y | | |
| SLIT2_E111_R | Y | | |
| SOX2_P546_F | Y | | |
| TPEF_seq_44_S88_R | Y | | |
| ASCL2_P609_R | Y | | |
| SOX17_P303_F | Y | | |
| TNK1_P41_R | Y | | |
| DCC_E53_R | Y | | |
| NRG1_E74_F | Y | | |
| AGTR1_P41_F | Y | | |
| MAF_P826_R | Y | | |
| IHH_P246_R | Y | | |
| TMEFF2_P152_R | Y | | |
| PRKCDBP_E206_F | Y | | |
| IGFBP2_P306_F | Y | | |
| COL18A1_P365_R | Y | | |
| TFAP2C_P765_F | Y | | |
| RAB32_E314_R | Y | | |
| CCKBR_P480_F | Y | | |
| SLC5A8_P38_R | Y | | |
| FOSL2_E384_R | Y | | |
| EGFR_P260_R | Y | | |
| EPHA7_E6_F | Y | | |
| DAPK1_E46_R | Y | | |
| PTGS2_P524_R | Y | | |
| WT1_P853_F | Y | | |
| PDGFRA_E125_F | N | | |
| NTSR1_P318_F | Y | | |
| IGSF4_P454_F | Y | | |

TABLE 1A-continued

List of CpG sites with specific differential hypermethylation and hypomethylation in lymphoid neoplasias (n: 200). CpG island associated (CGI): Yes (Y) or not (N).

| Lymphoid neoplasias hypermetylation (n: 200) | CGI | Lymphoid neoplasias hypomethylation (n: 54) | CGI |
|---|---|---|---|
| CYP1B1_E83_R | Y | | |
| RBP1_P426_R | Y | | |
| PLXDC2_E337_F | Y | | |
| WT1_E32_F | Y | | |
| PALM2-AKAP2_P183_R | Y | | |
| F2R_P839_F | Y | | |
| RASGRF1_E16_F | Y | | |
| NOTCH3_P198_R | Y | | |
| CEBPA_P706_F | Y | | |
| EVI1_E47_R | Y | | |
| HS3ST2_P546_F | Y | | |
| LOX_P313_R | Y | | |
| DAPK1_P345_R | Y | | |
| CDH11_E102_R | Y | | |
| ERG_E28_F | Y | | |
| GRB10_E85_R | Y | | |
| GATA6_P21_R | Y | | |
| CCNA1_E7_F | Y | | |
| EPHA5_P66_F | Y | | |
| HOXB13_E21_F | Y | | |
| NPY_E31_R | Y | | |
| EPHB1_E202_R | Y | | |
| IGFBP7_P297_F | Y | | |
| COL18A1_P494_R | Y | | |
| NOTCH3_E403_F | Y | | |
| TUSC3_P85_R | Y | | |
| MT1A_P49_R | Y | | |
| BMP2_E48_R | Y | | |
| IGFBP1_E48_R | Y | | |
| ERBB4_P255_F | Y | | |
| IGFBP2_P353_R | Y | | |
| CALCA_P75_F | Y | | |
| ADCYAP1_P455_R | Y | | |
| PAX6_P50_R | Y | | |
| IGF2AS_E4_F | Y | | |
| GABRB3_P92_F | Y | | |
| RIPK4_P172_F | Y | | |
| TWIST1_E117_R | Y | | |
| ALK_E183_R | Y | | |
| EPHA3_P106_R | Y | | |
| TBX1_P885_R | Y | | |
| PAX6_E129_F | Y | | |
| RET_seq_53_S374_F | Y | | |
| TWIST1_P355_R | Y | | |
| GRB10_P260_F | Y | | |
| BDNF_E19_R | Y | | |
| CDH1_P45_F | Y | | |
| EPHA5_E158_R | Y | | |
| TRIP6_P1090_F | Y | | |
| DIO3_P90_F | Y | | |
| OPCML_E219_R | Y | | |
| FGF5_P238_R | Y | | |
| HRASLS_E72_R | Y | | |
| ASCL1_E24_F | Y | | |
| EPHA7_P205_R | Y | | |
| HOXA11_E35_F | Y | | |
| HLF_E192_F | Y | | |
| IRAK3_P185_F | Y | | |
| INHA_P1189_F | Y | | |
| PYCARD_P150_F | Y | | |
| MT1A_P600_F | Y | | |
| LOX_P71_F | Y | | |
| PDGFRA_P1429_F | Y | | |
| FLT4_P180_R | Y | | |
| GAS7_E148_F | Y | | |
| DST_E31_F | Y | | |
| TEK_E75_F | N | | |
| THBS1_E207_R | Y | | |
| ROR2_E112_F | Y | | |
| IGFBP1_P12_R | Y | | |
| HIC2_P498_F | Y | | |
| MMP2_E21_R | Y | | |
| IHH_P529_F | Y | | |
| INHA_P1144_R | Y | | |
| PROK2_P390_F | Y | | |
| NRG1_P558_R | Y | | |
| TGFBI_P173_F | Y | | |
| FZD9_P175_F | Y | | |
| MEST_P62_R | Y | | |

TABLE 1B

List of CpG sites with specific highly-specific differential hypermethylation and hypomethylation in lymphoid neoplasias (n: 200). CpG island associated (CGI): Yes (Y) or not (N).

| Lymphoid neoplasias (hypermethylation) (n: 69) | CGI | Lymphoid neoplasias (hypomethylation) (n: 27) | CGI |
|---|---|---|---|
| IGSF4_P86_R | Y | DDR1_P332_R | N |
| FAT_P279_R | Y | LTA_P214_R | N |
| RAB32_P493_R | Y | NOTCH4_P938_F | N |
| IGF2_E134_R | Y | BLK_P668_R | N |
| FGFR2_P460_R | Y | PLA2G2A_P528_F | N |
| PTGS2_P308_F | Y | LCK_E28_F | Y |
| SEMA3C_E49_R | Y | DES_P1006_R | N |
| TFAP2C_E260_F | Y | PMP22_P975_F | N |
| ONECUT2_E96_F | Y | RHOH_P953_R | N |
| FAT_P973_R | Y | IL18BP_E285_F | N |
| IMPACT_P234_R | Y | BGN_P333_R | N |
| TJP1_P390_R | Y | NAT2_P11_F | N |
| IGFBP3_E65_R | Y | E2F5_P516_R | Y |
| CDH11_P203_R | Y | MPL_P657_F | N |
| CDH1_P52_R | Y | PLA2G2A_E268_F | N |
| ETV1_P515_F | Y | EPHX1_E152_F | N |
| EGFR_E295_R | Y | EPHX1_P1358_R | N |
| NTRK2_P10_F | Y | SFTPB_P689_R | N |
| CTSL_P81_F | Y | IGF1_P933_F | N |
| RBP1_E158_F | Y | IGF1_E394_F | N |
| FGFR2_P266_R | Y | HLA-DPB1_P540_F | N |
| DAPK1_P10_F | Y | CSF1R_P73_F | N |
| RET_seq_54_S260_F | Y | IL1B_P829_F | N |
| TJP1_P326_R | Y | GRB7_P160_R | N |
| ERBB4_P541_F | Y | MMP9_E88_R | N |
| NTRK2_P395_R | Y | KRT13_P676_F | N |
| SOX2_P546_F | Y | SMARCB1_P220_R | Y |
| TNK1_P41_R | Y | | |
| MAF_P826_R | Y | | |
| IHH_P246_R | Y | | |
| IGFBP2_P306_F | Y | | |
| COL18A1_P365_R | Y | | |
| RAB32_E314_R | Y | | |
| CCKBR_P480_F | Y | | |
| EGFR_P260_R | Y | | |
| EPHA7_E6_F | Y | | |
| DAPK1_E46_R | Y | | |
| PDGFRA_E125_F | N | | |
| IGSF4_P454_F | Y | | |
| PLXDC2_E337_F | Y | | |
| PALM2-AKAP2_P183_R | Y | | |
| F2R_P839_F | Y | | |
| CEBPA_P706_F | Y | | |
| EVI1_E47_R | Y | | |
| LOX_P313_R | Y | | |
| DAPK1_P345_R | Y | | |
| GRB10_E85_R | Y | | |
| HOXB13_E21_F | Y | | |
| NOTCH3_E403_F | Y | | |
| MT1A_P49_R | Y | | |
| BMP2_E48_R | Y | | |
| IGFBP1_E48_R | Y | | |
| ERBB4_P255_F | Y | | |
| IGFBP2_P353_R | Y | | |

TABLE 1B-continued

List of CpG sites with specific highly-specific differential hypermethylation and hypomethylation in lymphoid neoplasias (n: 200). CpG island associated (CGI): Yes (Y) or not (N).

| Lymphoid neoplasias (hypermethylation) (n: 69) | CGI | Lymphoid neoplasias (hypomethylation) (n: 27) | CGI |
|---|---|---|---|
| PAX6_P50_R | Y | | |
| RIPK4_P172_F | Y | | |
| PAX6_E129_F | Y | | |
| GRB10_P260_F | Y | | |
| CDH1_P45_F | Y | | |
| HRASLS_E72_R | Y | | |
| EPHA7_P205_R | Y | | |
| HLF_E192_F | Y | | |
| INHA_P1189_F | Y | | |
| LOX_P71_F | Y | | |
| PDGFRA_P1429_F | Y | | |
| DST_E31_F | Y | | |
| THBS1_E207_R | Y | | |
| IHH_P529_F | Y | | |
| INHA_P1144_R | Y | | |

In another embodiment of the first method of the invention, the methylation profile is determined by determining the methylation status in one or more CpG sites as defined in Table 2A or in Table 2B and the resulting methylation profile is compared with the methylation profile in same CpG sites in a DNA sample from a head and neck cancer.

TABLE 2A

List of CpG sites with specific differential hypermethylation and hypomethylation in head and neck cancer. CpG island associated (CGI): Yes (Y) or not (N).

| Head and neck cancer (hypermethylation) (n: 171) | CGI | Head and neck cancer (hypomethylation) (n: 20) | CGI |
|---|---|---|---|
| LCN2_P141_R | N | MMP2_P303_R | Y |
| PI3_P274_R | N | ERN1_P809_R | Y |
| KRT13_P341_R | N | MT1A_P600_F | Y |
| SLC22A18_P216_R | N | DLC1_E276_F | N |
| TMPRSS4_E83_F | N | RAB32_P493_R | Y |
| LCN2_P86_R | N | ICAM1_P386_R | Y |
| VAMP8_P241_F | N | JAK3_P156_R | N |
| KRT5_E196_R | Y | RUNX3_P247_F | Y |
| TRIP6_P1274_R | Y | TNFSF8_E258_R | N |
| TRIM29_P261_F | N | HLA-DPA1_P28_R | N |
| DSG1_P159_R | N | RUNX3_P393_R | Y |
| PENK_E26_F | Y | OSM_P188_F | Y |
| LY6G6E_P45_R | N | MPO_P883_R | N |
| TRIP6_P1090_F | Y | DLC1_P695_F | N |
| PSCA_P135_F | N | FANCE_P356_R | Y |
| JAK3_P1075_R | N | RUNX3_E27_R | N |
| STAT5A_P704_R | N | SERPINA5_P156_F | N |
| MST1R_E42_R | Y | HLA-DPA1_P205_R | N |
| HLA-DOB_E432_R | N | TNFSF8_P184_F | Y |
| EMR3_P39_R | N | DLC1_P88_R | N |
| NBL1_E205_R | N | | |
| NBL1_P24_F | N | | |
| ZIM3_P718_R | N | | |
| FGF1_P357_R | N | | |
| MAP3K8_P1036_F | Y | | |
| TGFB3_E58_R | N | | |
| AATK_E63_R | N | | |
| SERPINB5_P19_R | Y | | |
| MSH2_P1008_F | Y | | |
| CREBBP_P712_R | Y | | |
| MMP14_P13_F | Y | | |
| GRB7_P160_R | N | | |
| SFN_E118_F | Y | | |
| GLI2_E90_F | N | | |
| MST1R_P87_R | Y | | |
| TNFRSF1A_P678_F | N | | |
| GLI2_P295_F | Y | | |
| IL1RN_E42_F | N | | |

TABLE 2A-continued

List of CpG sites with specific differential hypermethylation and hypomethylation in head and neck cancer. CpG island associated (CGI): Yes (Y) or not (N).

| Head and neck cancer (hypermethylation) (n: 171) | CGI | Head and neck cancer (hypomethylation) (n: 20) | CGI |
|---|---|---|---|
| BCR_P422_F | Y | | |
| CXCL9_E268_R | N | | |
| FGF1_E5_F | N | | |
| FER_P581_F | N | | |
| SEPT9_P58_R | Y | | |
| TRIM29_P135_F | N | | |
| SRC_P164_F | N | | |
| WEE1_P924_R | N | | |
| ALOX12_E85_R | Y | | |
| KCNK4_E3_F | Y | | |
| EGF_E339_F | N | | |
| S100A2_P1186_F | N | | |
| MOS_E60_R | Y | | |
| CD9_P585_R | Y | | |
| AATK_P519_R | Y | | |
| HOXA5_E187_F | Y | | |
| EPHA5_P66_F | Y | | |
| PTPN6_P282_R | N | | |
| CLDN4_P1120_R | N | | |
| SNCG_P98_R | Y | | |
| AATK_P709_R | Y | | |
| HOXA9_E252_R | Y | | |
| DHCR24_P652_R | N | | |
| CSF1R_P73_F | N | | |
| KRT5_P308_F | N | | |
| FRK_P36_F | N | | |
| EPHA2_P203_F | Y | | |
| IL1RN_P93_R | N | | |
| IFNGR2_P377_R | Y | | |
| RIPK3_P124_F | N | | |
| IL12B_P392_R | N | | |
| KLK11_P103_R | N | | |
| HS3ST2_E145_R | Y | | |
| HOXA9_P1141_R | Y | | |
| IGF1_E394_F | N | | |
| SLC14A1_P369_R | N | | |
| LEFTY2_P561_F | Y | | |
| DDIT3_P1313_R | Y | | |
| PADI4_P1158_R | N | | |
| HOXA11_P698_F | Y | | |
| HOXB2_P99_F | Y | | |
| FASTK_P598_R | Y | | |
| TRIM29_E189_F | Y | | |
| LIG3_P622_R | Y | | |
| SNCG_E119_F | N | | |
| SPDEF_P6_R | N | | |
| SNCG_P53_F | Y | | |
| CALCA_E174_R | Y | | |
| ALOX12_P223_R | Y | | |
| OGG1_E400_F | Y | | |
| HS3ST2_P171_F | Y | | |
| CEACAM1_P44_R | N | | |
| CALCA_P171_F | Y | | |
| DBC1_E204_F | Y | | |
| DES_P1006_R | N | | |
| DDR1_P332_R | N | | |
| NPR2_P1093_F | Y | | |
| NID1_P677_F | N | | |
| GSTM2_P453_R | N | | |
| GRB7_E71_R | N | | |
| KCNK4_P171_R | N | | |
| HTR1B_E232_R | Y | | |
| GFAP_P56_R | N | | |
| SOX1_P294_F | Y | | |
| IL1A_E113_R | N | | |
| PITX2_E24_R | Y | | |
| HOXA5_P479_F | Y | | |
| PADI4_P1011_R | N | | |
| PLAT_E158_F | N | | |
| ASCL1_P747_F | Y | | |
| HTR1B_P222_F | Y | | |
| DSG1_E292_F | N | | |
| PRSS8_E134_R | Y | | |

TABLE 2A-continued

List of CpG sites with specific differential hypermethylation and hypomethylation in head and neck cancer. CpG island associated (CGI): Yes (Y) or not (N).

| Head and neck cancer (hypermethylation) (n: 171) | CGI | Head and neck cancer (hypomethylation) (n: 20) | CGI |
| --- | --- | --- | --- |
| AIM2_E208_F | N | | |
| CSF3_P309_R | N | | |
| CHI3L2_E10_F | N | | |
| SOX17_P303_F | Y | | |
| RARA_P176_R | N | | |
| ZIM3_P451_R | Y | | |
| DIO3_E230_R | Y | | |
| DLK1_E227_R | Y | | |
| ASB4_P391_F | N | | |
| SOX17_P287_R | Y | | |
| CAPG_E228_F | N | | |
| CSF1R_E26_F | N | | |
| ARHGDIB_P148_R | N | | |
| FZD9_E458_F | Y | | |
| CYP2E1_P416_F | N | | |
| THBS2_P605_R | N | | |
| TAL1_P594_F | Y | | |
| MMP14_P208_R | N | | |
| SEPT9_P374_F | Y | | |
| FGFR4_P610_F | N | | |
| ZP3_P220_F | N | | |
| IGFBP5_P9_R | Y | | |
| SEPT5_P441_F | Y | | |
| SPARC_P195_F | N | | |
| S100A4_E315_F | N | | |
| PENK_P447_R | Y | | |
| S100A2_E36_R | N | | |
| PTHR1_P258_F | N | | |
| TNFRSF10C_P7_F | Y | | |
| CD9_P504_F | Y | | |
| RAD50_P191_F | Y | | |
| MYH11_P22_F | Y | | |
| IHH_E186_F | Y | | |
| BMP4_P199_R | Y | | |
| DCC_P471_R | Y | | |
| PTPRH_E173_F | N | | |
| BCR_P346_F | Y | | |
| EYA4_E277_F | Y | | |
| SERPINE1_P519_F | N | | |
| PTK6_E50_F | Y | | |
| TBX1_P885_R | Y | | |
| ESR1_P151_R | Y | | |
| CD81_P272_R | Y | | |
| SEMA3A_P658_R | N | | |
| TGFBI_P173_F | Y | | |
| HGF_E102_R | N | | |
| CTSL_P264_R | Y | | |
| TNK1_P221_F | Y | | |
| NOTCH3_P198_R | Y | | |
| VAMP8_P114_F | Y | | |
| EPHA2_P340_R | N | | |
| BAX_E281_R | Y | | |
| CPA4_E20_F | N | | |
| CD82_P557_R | Y | | |
| IGFBP3_P423_R | Y | | |
| CTSD_P726_F | Y | | |
| MYOD1_E156_F | Y | | |
| SEPT5_P464_R | Y | | |
| TPEF_seq_44_S88_R | Y | | |
| CPA4_P1265_R | N | | |

TABLE 2B

List of CpG sites with highly-specific specific differential hypermethylation and hypomethylation in head and neck cancer. CpG island associated (CGI): Yes (Y) or not (N).

| Head and neck cancer (hypermethylation) (n: 97) | CGI | Head and neck cancer (hypomethylation) (n: 10) | CGI |
| --- | --- | --- | --- |
| LCN2_P141_R | N | ERN1_P809_R | Y |
| PI3_P274_R | N | MT1A_P600_F | Y |
| KRT13_P341_R | N | DLC1_E276_F | N |
| SLC22A18_P216_R | N | RAB32_P493_R | Y |
| TMPRSS4_E83_F | N | ICAM1_P386_R | Y |
| VAMP8_P241_F | N | JAK3_P156_R | N |
| KRT5_E196_R | Y | TNFSF8_E258_R | N |
| TRIP6_P1274_R | Y | FANCE_P356_R | Y |
| DSG1_P159_R | N | SERPINA5_P156_F | N |
| LY6G6E_P45_R | N | DLC1_P88_R | N |
| PSCA_P135_F | N | | |
| JAK3_P1075_R | N | | |
| MST1R_E42_R | Y | | |
| HLA-DOB_E432_R | N | | |
| EMR3_P39_R | N | | |
| NBL1_E205_R | N | | |
| NBL1_P24_F | N | | |
| ZIM3_P718_R | N | | |
| FGF1_P357_R | N | | |
| MAP3K8_P1036_F | Y | | |
| AATK_E63_R | N | | |
| SERPINB5_P19_R | Y | | |
| MSH2_P1008_F | Y | | |
| CREBBP_P712_R | Y | | |
| MMP14_P13_F | Y | | |
| GRB7_P160_R | N | | |
| SFN_E118_F | Y | | |
| GLI2_E90_F | N | | |
| MST1R_P87_R | Y | | |
| TNFRSF1A_P678_F | N | | |
| GLI2_P295_F | Y | | |
| IL1RN_E42_F | N | | |
| CXCL9_E268_R | N | | |
| FGF1_E5_F | N | | |
| FER_P581_F | N | | |
| SEPT9_P58_R | Y | | |
| TRIM29_P135_F | N | | |
| SRC_P164_F | N | | |
| WEE1_P924_R | N | | |
| EGF_E339_F | N | | |
| AATK_P519_R | Y | | |
| CLDN4_P1120_R | N | | |
| CSF1R_P73_F | N | | |
| KRT5_P308_F | N | | |
| FRK_P36_F | N | | |
| EPHA2_P203_F | Y | | |
| RIPK3_P124_F | N | | |
| IL12B_P392_R | N | | |
| KLK11_P103_R | N | | |
| IGF1_E394_F | N | | |
| PADI4_P1158_R | N | | |
| HOXB2_P99_F | Y | | |
| FASTK_P598_R | Y | | |
| TRIM29_E189_F | Y | | |
| LIG3_P622_R | N | | |
| SPDEF_P6_R | N | | |
| OGG1_E400_F | Y | | |
| CEACAM1_P44_R | N | | |
| CALCA_P171_F | Y | | |
| DES_P1006_R | N | | |
| NPR2_P1093_F | Y | | |
| NID1_P677_F | N | | |
| KCNK4_P171_R | N | | |
| GFAP_P56_R | N | | |
| IL1A_E113_R | N | | |
| HOXA5_P479_F | Y | | |
| PADI4_P1011_R | N | | |
| PLAT_E158_F | N | | |
| DSG1_E292_F | N | | |
| PRSS8_E134_R | Y | | |
| AIM2_E208_F | N | | |
| CSF3_P309_R | N | | |

TABLE 2B-continued

List of CpG sites with highly-specific specific differential hypermethylation and hypomethylation in head and neck cancer. CpG island associated (CGI): Yes (Y) or not (N).

| Head and neck cancer (hypermethylation) (n: 97) | CGI | Head and neck cancer (hypomethylation) (n: 10) | CGI |
|---|---|---|---|
| ZIM3_P451_R | Y | | |
| ASB4_P391_F | N | | |
| CAPG_E228_F | N | | |
| CSF1R_E26_F | N | | |
| CYP2E1_P416_F | N | | |
| THBS2_P605_R | N | | |
| MMP14_P208_R | N | | |
| FGFR4_P610_F | N | | |
| ZP3_P220_F | N | | |
| S100A4_E315_F | N | | |
| S100A2_E36_R | N | | |
| PTHR1_P258_F | N | | |
| RAD50_P191_F | Y | | |
| PTPRH_E173_F | N | | |
| PTK6_E50_F | Y | | |
| SEMA3A_P658_R | N | | |
| HGF_E102_R | N | | |
| CTSL_P264_R | Y | | |
| TNK1_P221_F | Y | | |
| VAMP8_P114_F | N | | |
| EPHA2_P340_R | N | | |
| CPA4_E20_F | N | | |
| CD82_P557_R | Y | | |
| CTSD_P726_F | Y | | |
| CPA4_P1265_R | N | | |

In another embodiment of the first method of the invention, the methylation profile is determined by determining the methylation status in one or more CpG sites as defined in Table 3A or in Table 3B and the resulting methylation profile is compared with the methylation profile in same CpG sites in a DNA sample from a pancreatic cancer.

TABLE 3A

List of CpG sites with specific differential hypermethylation and hypomethylation in pancreatic cancer. CpG island associated (CGI): Yes (Y) or not (N).

| Pancreatic cancer (hypermethylation) (n: 150) | CGI | Pancreatic cancer (hypomethylation) (n: 98) | CGI |
|---|---|---|---|
| CDH13_E102_F | Y | SERPINB5_P19_R | Y |
| GAS7_E148_F | Y | S100A2_P1186_F | N |
| TWIST1_E117_R | Y | PI3_P274_R | N |
| CCNA1_P216_F | Y | SFN_E118_F | Y |
| SLIT2_P208_F | Y | IAPP_E280_F | N |
| FLT3_E326_R | Y | TRIM29_P135_F | N |
| CCNA1_E7_F | Y | PTPRH_P255_F | N |
| NPY_P295_F | Y | NOS2A_E117_R | N |
| GALR1_E52_F | Y | CYP2E1_P416_F | N |
| WT1_E32_F | Y | SFTPA1_E340_R | N |
| RASGRF1_E16_F | Y | CREBBP_P712_R | Y |
| SFRP1_E398_R | Y | NDN_P1110_F | N |
| TPEF_seq_44_S88_R | Y | TRIM29_E189_F | Y |
| MYOD1_E156_F | Y | CSF2_E248_R | N |
| NTRK3_P636_R | Y | ITK_P114_F | N |
| MDR1_seq_42_S300_R | Y | TRIM29_P261_F | N |
| DBC1_P351_R | Y | TRIP6_P1090_F | Y |
| EYA4_E277_F | Y | IL1RN_E42_F | N |
| FGF8_P473_F | Y | SEPT9_P58_R | Y |
| HS3ST2_P171_F | Y | GLI2_P295_F | Y |
| SOX1_P294_F | Y | TFF2_P178_F | N |
| CDH13_P88_F | Y | CXCL9_E268_R | N |
| NTRK3_P752_F | Y | TFF1_P180_R | N |
| SEZ6L_P249_F | Y | MST1R_E42_R | Y |
| NTRK3_E131_F | Y | PI3_E107_F | N |
| DLK1_E227_R | Y | GLI2_E90_F | N |
| HOXA9_P1141_R | Y | NBL1_P24_F | N |

TABLE 3A-continued

List of CpG sites with specific differential hypermethylation and hypomethylation in pancreatic cancer. CpG island associated (CGI): Yes (Y) or not (N).

| Pancreatic cancer (hypermethylation) (n: 150) | CGI | Pancreatic cancer (hypomethylation) (n: 98) | CGI |
|---|---|---|---|
| SOX17_P303_F | Y | CSF2_P605_F | N |
| MYH11_P22_F | Y | NOS3_P38_F | N |
| SOX1_P1018_R | Y | TMPRSS4_P552_F | N |
| HIC2_P498_F | Y | UGT1A1_P315_R | N |
| MOS_E60_R | Y | NID1_P677_F | N |
| IGFBP3_P423_R | Y | NBL1_E205_R | N |
| ERG_E28_F | Y | S100A2_E36_R | N |
| HS3ST2_E145_R | Y | LCN2_P141_R | N |
| FLT1_P302_F | Y | UGT1A1_E11_F | N |
| TBX1_P885_R | Y | PRSS1_E45_R | N |
| TAL1_P594_F | Y | IFNG_E293_F | N |
| SOX17_P287_R | Y | NCL_P1102_F | Y |
| HOXA9_E252_R | Y | APBA2_P305_R | N |
| ADCYAP1_P398_F | Y | SPI1_P929_F | N |
| TMEFF2_P152_R | Y | FGFR4_P610_F | N |
| PENK_P447_R | Y | SRC_P164_F | N |
| MMP2_P303_R | Y | SEPT9_P374_F | Y |
| BMP3_P56_R | Y | EMR3_P39_R | N |
| COL1A2_E299_F | Y | KRT1_P798_R | N |
| TFPI2_P9_F | Y | PRSS8_E134_R | Y |
| NGFB_E353_F | Y | MST1R_P87_R | Y |
| TUSC3_E29_R | Y | CPA4_E20_F | N |
| FLT1_P615_R | Y | IFNG_P188_F | N |
| CHGA_E52_F | Y | NOS2A_P288_R | N |
| GABRB3_E42_F | Y | SLC22A3_P634_F | Y |
| SFRP1_P157_F | Y | KIAA0125_E29_F | N |
| NEFL_P209_R | Y | NOTCH4_E4_F | N |
| SEZ6L_P299_F | Y | SNCG_E119_F | N |
| ASCL2_P360_F | Y | ZP3_P220_F | N |
| HS3ST2_P546_F | Y | PTK6_E50_F | Y |
| FLT4_P180_R | Y | CLDN4_P1120_R | N |
| EPHA5_E158_R | Y | MPO_E302_R | N |
| FLT1_E444_F | Y | BRCA1_P835_R | Y |
| GABRB3_P92_F | Y | LCN2_P86_R | N |
| ESR1_P151_R | Y | GUCY2F_P255_F | N |
| CCND2_P898_R | Y | PTPRH_E173_F | N |
| RET_seq_53_S374_F | Y | PTPN6_P282_R | N |
| NEFL_E23_R | Y | GML_P281_R | N |
| COL1A2_P48_R | Y | PSCA_P135_F | N |
| EYA4_P794_F | Y | LIG3_P622_R | N |
| SLC5A8_E60_R | Y | CEACAM1_P44_R | N |
| SLIT2_E111_R | Y | WNT8B_E487_F | N |
| FLI1_E29_F | Y | BMP4_P199_R | Y |
| WT1_P853_F | Y | GABRG3_E123_R | N |
| KDR_P445_R | Y | MAPK4_E273_R | N |
| MYH11_P236_R | Y | CAPG_E228_F | N |
| HOXA11_P698_F | Y | FGF1_P357_R | N |
| THY1_P149_R | Y | DLC1_P695_F | N |
| ADAMTS12_E52_R | Y | VAMP8_P241_F | N |
| SCGB3A1_E55_R | Y | APOA1_P261_F | N |
| ESR1_E298_R | Y | MAGEC3_E307_F | N |
| TMEFF2_E94_R | Y | CCR5_P630_R | N |
| PROK2_P390_F | Y | PWCR1_P811_F | N |
| KIT_P367_R | Y | TRIP6_P1274_R | Y |
| HOXA9_P303_F | Y | CASP8_E474_F | N |
| NPY_E31_R | Y | CTLA4_P1128_F | Y |
| TFPI2_P152_R | Y | GABRA5_P862_R | N |
| TFPI2_E141_F | Y | GFAP_P56_R | N |
| PITX2_E24_R | Y | MMP10_E136_R | N |
| DES_E228_R | Y | KLK10_P268_R | N |
| ASCL1_E24_F | Y | IL12B_P1453_F | Y |
| GSTM2_E153_F | Y | PADI4_P1011_R | N |
| NPY_P91_F | Y | PWCR1_P357_F | N |
| FZD9_E458_F | Y | AATK_E63_R | N |
| TIMP3_seq_7_S38_F | Y | HLA-DOB_E432_R | N |
| NGFB_P13_F | Y | IL1RN_P93_R | N |
| MMP2_P197_F | Y | FRK_P36_F | N |
| DBC1_E204_R | Y | EPHA2_P203_F | Y |
| GSTM2_P109_R | N | SPP1_P647_F | N |
| CDH11_E102_R | Y | PTHR1_P258_F | N |
| ADCYAP1_P455_R | Y | BAX_E281_R | Y |
| COL1A1_P5_F | Y | | |
| TWIST1_P355_R | Y | | |

TABLE 3A-continued

List of CpG sites with specific differential hypermethylation and hypomethylation in pancreatic cancer. CpG island associated (CGI): Yes (Y) or not (N).

| Pancreatic cancer (hypermethylation) (n: 150) | CGI | Pancreatic cancer (hypomethylation) (n: 98) | CGI |
|---|---|---|---|
| ATP10A_P147_F | Y | | |
| FRZB_E186_R | Y | | |
| SMO_P455_R | Y | | |
| CALCA_E174_R | Y | | |
| HCK_P858_F | Y | | |
| PENK_E26_F | Y | | |
| MMP2_E21_R | Y | | |
| TIAM1_P117_F | Y | | |
| TSP50_P137_F | Y | | |
| PTCH2_P568_R | Y | | |
| BMP3_E147_F | Y | | |
| GUCY2D_E419_R | Y | | |
| ASCL2_P609_R | Y | | |
| GDF10_P95_R | Y | | |
| CCND2_P887_F | Y | | |
| GDF10_E39_F | Y | | |
| FLT3_P302_F | Y | | |
| IGFBP7_P297_F | Y | | |
| SLC5A8_P38_R | Y | | |
| FGF5_E16_F | Y | | |
| CALCA_P75_F | Y | | |
| POMC_P53_F | Y | | |
| DCC_E53_R | Y | | |
| KIT_P405_F | Y | | |
| ZIM2_P22_F | Y | | |
| ASCL1_P747_F | Y | | |
| TUSC3_P85_R | Y | | |
| TMEFF1_P234_F | Y | | |
| POMC_P400_R | Y | | |
| POMC_E254_F | Y | | |
| FGF3_E198_R | Y | | |
| BDNF_E19_R | Y | | |
| EYA4_P508_F | Y | | |
| ROR2_E112_F | Y | | |
| SGCE_E149_F | Y | | |
| HCK_P46_R | Y | | |
| ADCYAP1_E163_R | Y | | |
| TPEF_seq_44_S36_F | Y | | |
| ADAMTS12_P250_R | Y | | |
| HOXA5_E187_F | Y | | |
| NRG1_E74_F | Y | | |
| MCAM_P265_R | Y | | |
| ER_seq_a1_S60_F | Y | | |
| MT1A_P600_F | Y | | |
| GSTM1_P266_F | Y | | |
| GSTM2_P453_R | N | | |
| EPHA5_P66_F | Y | | |
| MFAP4_P197_F | N | | |
| RET_P717_F | N | | |
| HIC2_P528_R | Y | | |

TABLE 3B

List of CpG sites with highly-specific differential hypermethylation and hypomethylation in pancreatic cancer. CpG island associated (CGI): Yes (Y) or not (N).

| Pancreatic cancer (hypermethylation) (n: 150) | CGI | Pancreatic cancer (hypomethylation) (n: 98) | CGI |
|---|---|---|---|
| FGF8_P473_F | Y | CYP2E1_P416_F | N |
| SEZ6L_P249_F | Y | CREBBP_P712_R | Y |
| FLT1_P302_F | Y | NDN_P1110_F | N |
| FLT1_P615_R | Y | CSF2_E248_R | N |
| SEZ6L_P299_F | Y | SEPT9_P58_R | Y |
| FLT1_E444_F | Y | TFF1_P180_F | N |
| NEFL_E23_R | Y | CSF2_P605_F | N |
| COL1A2_P48_R | Y | LCN2_P141_R | N |
| MYH11_P236_R | Y | UGT1A1_E11_F | N |
| MMP2_P197_F | Y | NCL_P1102_F | Y |

TABLE 3B-continued

List of CpG sites with highly-specific differential hypermethylation and hypomethylation in pancreatic cancer. CpG island associated (CGI): Yes (Y) or not (N).

| Pancreatic cancer (hypermethylation) (n: 150) | CGI | Pancreatic cancer (hypomethylation) (n: 98) | CGI |
|---|---|---|---|
| COL1A1_P5_F | Y | SPI1_P929_F | N |
| SMO_P455_R | Y | FGFR4_P610_F | N |
| PTCH2_P568_R | Y | SEPT9_P374_F | Y |
| GDF10_P95_R | Y | MST1R_P87_R | N |
| GDF10_E39_F | Y | SLC22A3_P634_F | Y |
| POMC_P53_F | Y | KIAA0125_E29_F | N |
| ZIM2_P22_F | Y | SNCG_E119_F | N |
| TMEFF1_P234_F | Y | GUCY2F_P255_F | N |
| POMC_E254_F | Y | GML_P281_R | N |
| FGF3_E198_R | Y | LIG3_P622_R | N |
| SGCE_E149_F | Y | WNT8B_E487_F | N |
| ADCYAP1_E163_R | Y | BMP4_P199_R | Y |
| TPEF_seq_44_S36_F | Y | GABRG3_E123_R | N |
| MCAM_P265_R | Y | MAPK4_E273_R | N |
| RET_P717_F | N | FGF1_P357_R | N |
| HIC2_P528_R | Y | APOA1_P261_F | N |
| | | PWCR1_P811_F | N |
| | | CTLA4_P1128_F | N |
| | | GFAP_P56_R | N |
| | | KLK10_P268_R | N |
| | | PWCR1_P357_F | N |
| | | IL1RN_P93_R | N |
| | | FRK_P36_F | N |
| | | EPHA2_P203_F | Y |

In another embodiment of the first method of the invention, the methylation profile is determined by determining the methylation status in one or more CpG sites as defined in Table 4A or in Table 4B and the resulting methylation profile is compared with the methylation profile in same CpG sites in a DNA sample from a endometrial cancer.

TABLE 4A

List of CpG sites with specific differential hypermethylation and hypomethylation in endometrial cancer. CpG island associated (CGI): Yes (Y) or not (N).

| Endometrial cancer hypermethylation (n: 102) | CGI | Endometrial cancer hypomethylation (n: 22) | CGI |
|---|---|---|---|
| PENK_E26_F | Y | BLK_P14_F | N |
| DLK1_E227_R | Y | IFNG_E293_F | N |
| SOX1_P294_F | Y | MEST_P62_R | Y |
| NEFL_P209_R | Y | EMR3_E61_F | N |
| HTR1B_P222_F | Y | PTHLH_E251_F | N |
| NPY_P295_F | Y | NBL1_P24_F | N |
| CDH13_P88_F | Y | SPP1_P647_F | N |
| CDH13_E102_F | Y | CEACAM1_P44_R | N |
| HTR1B_E232_R | Y | MST1R_E42_R | Y |
| DCC_P471_R | Y | NID1_P677_F | N |
| ADCYAP1_P455_R | Y | PTHLH_P15_R | N |
| ADCYAP1_P398_F | Y | MEST_P4_F | Y |
| TPEF_seq_44_S88_R | Y | PI3_E107_F | N |
| NPY_E31_R | Y | PTPN6_P282_R | N |
| PENK_P447_R | Y | PTPRH_E173_F | N |
| HS3ST2_E145_R | Y | EMR3_P39_R | N |
| HS3ST2_P171_F | Y | IL2_P607_R | N |
| CFTR_P372_R | Y | CLDN4_P1120_R | N |
| DBC1_E204_F | Y | TRIP6_P1090_F | Y |
| ASCL2_P360_F | Y | ASB4_P52_R | N |
| MOS_E60_R | Y | GFI1_P208_R | Y |
| TERT_P360_R | Y | TRIP6_P1274_R | Y |
| EPHA5_E158_R | Y | | |
| DBC1_P351_R | Y | | |
| OPCML_E219_R | Y | | |
| DIO3_P674_F | Y | | |
| DCC_P177_F | Y | | |
| SOX1_P1018_R | Y | | |
| THY1_P149_R | Y | | |

TABLE 4A-continued

List of CpG sites with specific differential hypermethylation and hypomethylation in endometrial cancer. CpG island associated (CGI): Yes (Y) or not (N).

| Endometrial cancer hypermethylation (n: 102) | CGI | Endometrial cancer hypomethylation (n: 22) | CGI |
|---|---|---|---|
| RASSF1_E116_F | Y | | |
| ASCL1_P747_F | Y | | |
| GSTM2_E153_F | Y | | |
| SLC5A8_E60_R | Y | | |
| MYOD1_E156_F | Y | | |
| ISL1_E87_R | Y | | |
| GUCY2D_E419_R | Y | | |
| HOXA9_E252_R | Y | | |
| HCK_P858_F | Y | | |
| ZNF215_P129_R | Y | | |
| PRKCDBP_E206_F | Y | | |
| SEPT9_P374_F | Y | | |
| PLS3_E70_F | Y | | |
| CD40_P372_R | Y | | |
| TMEFF2_E94_R | Y | | |
| CALCA_E174_R | Y | | |
| GSTM1_P266_F | Y | | |
| CYP1B1_E83_R | Y | | |
| SPARC_P195_F | N | | |
| SLC22A3_E122_R | Y | | |
| TMEFF2_P152_R | Y | | |
| ISL1_P379_F | Y | | |
| DIO3_P90_F | Y | | |
| NTRK3_P752_F | Y | | |
| RASSF1_P244_F | Y | | |
| HOXA11_P698_F | Y | | |
| AGTR1_P41_F | Y | | |
| MLF1_E243_F | Y | | |
| EYA4_E277_F | Y | | |
| HLA-F_E402_F | Y | | |
| NTRK3_P636_R | Y | | |
| FLI1_E29_F | Y | | |
| BDNF_E19_R | Y | | |
| TJP2_P330_R | Y | | |
| TSP50_P137_F | Y | | |
| ISL1_P554_F | Y | | |
| ABO_P312_F | Y | | |
| STAT5A_E42_F | N | | |
| FGF2_P229_F | Y | | |
| MFAP4_P10_R | N | | |
| MME_E29_F | Y | | |
| MDR1_seq_42_S300_R | Y | | |
| MLH1_P381_F | Y | | |
| GSTM2_P109_R | N | | |
| GSTM2_P453_R | N | | |
| NTSR1_P318_F | Y | | |
| JAK3_E64_F | Y | | |
| NRG1_P558_R | Y | | |
| TUSC3_E29_R | Y | | |
| ZNF215_P71_R | Y | | |
| APC_P14_F | Y | | |
| GABRB3_E42_F | Y | | |
| NTRK3_E131_F | Y | | |
| IRAK3_P185_F | Y | | |
| TIMP3_seq_7_S38_F | Y | | |
| TAL1_P594_F | Y | | |
| WT1_P853_F | Y | | |
| BMP3_P56_R | Y | | |
| MMP2_P303_R | Y | | |
| BMP3_E147_F | Y | | |
| IRAK3_P13_F | Y | | |
| IRAK3_E130_F | Y | | |
| EPHA3_P106_R | Y | | |
| CD9_P585_R | Y | | |
| FRZB_E186_R | Y | | |
| WNT2_P217_F | Y | | |
| TNFRSF10D_E27_F | Y | | |
| WT1_E32_F | Y | | |
| DAB2IP_E18_R | Y | | |
| TIAM1_P117_F | Y | | |
| CDH11_P354_R | Y | | |
| PITX2_E24_R | Y | | |
| CHFR_P501_F | Y | | |

TABLE 4B

List of CpG sites with highly-specific differential hypermethylation and hypomethylation in endometrial cancer. CpG island associated (CGI): Yes (Y) or not (N).

| Endometrial cancer (hypermethylation) (n: 102) | CGI | Endometrial cancer (hypomethylation) (n: 22) | CGI |
|---|---|---|---|
| HLA-F_E402_F | Y | PTHLH_E251_F | N |
| ABO_P312_F | Y | PTHLH_P15_R | N |
| MLH1_P381_F | Y | IL2_P607_R | N |
| JAK3_E64_F | Y | ASB4_P52_R | N |
| | | GFI1_P208_R | Y |

In another embodiment of the first method of the invention, the methylation profile is determined by determining the methylation status in one or more CpG sites as defined in Table 5A or in Table 5B and the resulting methylation profile is compared with the methylation profile in same CpG sites in a DNA sample from a colon cancer.

TABLE 5A

List of CpG sites with specific differential hypermethylation and hypomethylation in colon cancer. CpG island associated (CGI): Yes (Y) or not (N).

| Colon cancer (hypermethylation) (96) | CGI | Colon cancer (hypomethylation) (3) | CGI |
|---|---|---|---|
| EYA4_E277_F | Y | PI3_E107_F | N |
| TWIST1_E117_R | Y | NEU1_P745_F | Y |
| SFRP1_P157_F | Y | S100A2_E36_R | N |
| SLIT2_E111_R | Y | | |
| TMEFF2_E94_R | Y | | |
| SFRP1_E398_R | Y | | |
| NPY_E31_R | Y | | |
| TFPI2_P9_F | Y | | |
| NPY_P295_F | Y | | |
| TFPI2_P152_R | Y | | |
| FLT4_P180_R | Y | | |
| HS3ST2_E145_R | Y | | |
| SLIT2_P208_R | Y | | |
| DAB2IP_E18_R | Y | | |
| GAS7_E148_F | Y | | |
| NGFB_P13_F | Y | | |
| TMEFF2_P152_R | Y | | |
| NTSR1_P318_F | Y | | |
| FLI1_E29_F | Y | | |
| GSTM2_E153_F | Y | | |
| RASGRF1_E16_F | Y | | |
| MME_E29_F | Y | | |
| NGFB_E353_F | Y | | |
| EYA4_P794_F | Y | | |
| FGF5_P238_R | Y | | |
| CD40_P372_R | Y | | |
| WNT2_P217_F | Y | | |
| IGFBP3_P423_R | Y | | |
| NTRK3_P752_F | Y | | |
| WT1_E32_F | Y | | |

TABLE 5A-continued

List of CpG sites with specific differential hypermethylation and hypomethylation in colon cancer. CpG island associated (CGI): Yes (Y) or not (N).

| Colon cancer (hypermethylation) (96) | CGI | Colon cancer (hypomethylation) (3) |
|---|---|---|
| SCGB3A1_E55_R | Y | |
| HS3ST2_P171_F | Y | |
| AGTR1_P41_F | Y | |
| DBC1_E204_F | Y | |
| FLT3_E326_R | Y | |
| TBX1_P885_R | Y | |
| DLK1_E227_R | Y | |
| CDH13_P88_F | Y | |
| TPEF_seq_44_S88_R | Y | |
| ESR1_E298_R | Y | |
| NTRK3_E131_F | Y | |
| THY1_P149_R | Y | |
| NPY_P91_F | Y | |
| ER_seq_a1_S60_F | Y | |
| ALK_E183_R | Y | |
| FGF5_E16_F | Y | |
| ALK_P28_F | Y | |
| TWIST1_P355_R | Y | |
| ADCYAP1_P398_F | Y | |
| ESR1_P151_R | Y | |
| SOX17_P287_R | Y | |
| IRAK3_P13_F | Y | |
| GABRB3_P92_F | Y | |
| SOX1_P294_F | Y | |
| HOXA5_E187_F | Y | |
| HTR1B_E232_R | Y | |
| EPHA5_E158_R | Y | |
| CDH13_E102_F | Y | |
| MOS_E60_R | Y | |
| MYOD1_E156_F | Y | |
| CHFR_P501_F | Y | |
| EYA4_P508_F | Y | |
| HIC-1_seq_48_S103_R | Y | |
| CYP1B1_E83_R | Y | |
| KDR_P445_R | Y | |
| MYH11_P22_F | Y | |
| ADAMTS12_E52_R | Y | |
| NTRK3_P636_R | Y | |
| DCC_P471_R | Y | |
| TUSC3_E29_R | Y | |
| KDR_E79_F | Y | |
| CSPG2_E38_F | Y | |
| PENK_P447_R | Y | |
| HCK_P858_F | Y | |
| ADCYAP1_P455_R | Y | |
| CSPG2_P82_R | Y | |
| NRG1_P558_R | Y | |
| IGF2AS_E4_F | Y | |
| GABRB3_E42_F | Y | |
| CCNA1_P216_F | Y | |
| SOX17_P303_F | Y | |
| CDH11_P354_R | Y | |
| FGF3_P171_R | Y | |
| GSTM2_P109_R | N | |
| DBC1_P351_R | Y | |
| OPCML_E219_R | Y | |
| WT1_P853_F | Y | |
| COL1A2_E299_F | Y | |
| TFPI2_E141_F | Y | |
| PDE1B_P263_R | Y | |
| IRAK3_E130_F | Y | |
| HS3ST2_P546_F | Y | |
| MMP2_P303_R | Y | |
| NEFL_P209_R | Y | |
| TIAM1_P117_F | Y | |
| TUSC3_P85_R | Y | |

TABLE 5B

List of CpG sites with highly-specific differential hypermethylation and hypomethylation in colon cancer. CpG island associated (CGI): Yes (Y) or not (N).

| Colon cancer (hypermethylation) (3) | CGI | Colon cancer (hypomethylation) (1) | CGI |
|---|---|---|---|
| ALK_P28_F | Y | NEU1_P745_F | Y |
| CSPG2_E38_F | Y | | |
| PDE1B_P263_R | Y | | |

In another embodiment of the first method of the invention, the methylation profile is determined by determining the methylation status in one or more CpG sites as defined in Table 6A or in Table 6B and the resulting methylation profile is compared with the methylation profile in same CpG sites in a DNA sample from a prostate cancer.

TABLE 6A

List of CpG sites with specific differential hypermethylation and hypomethylation in prostate cancer. CpG island associated (CGI): Yes (Y) or not (N).

| Prostate cancer (hypermethylation) (n: 76) | CGI | Prostate cancer (hypomethylation) (n: 4) | CGI |
|---|---|---|---|
| GSTP1_E322_R | Y | MEST_P4_F | Y |
| GSTM2_E153_F | Y | DLC1_P695_F | N |
| RARB_P60_F | Y | MEST_P62_R | Y |
| COL18A1_P494_R | Y | PTPN6_P282_R | N |
| PDGFRB_P273_F | Y | | |
| APC_P14_F | Y | | |
| MFAP4_P10_R | N | | |
| SCGB3A1_E55_R | Y | | |
| ALOX12_P223_R | Y | | |
| POMC_P400_R | Y | | |
| ALOX12_E85_R | Y | | |
| GSTM2_P109_R | N | | |
| PDGFRB_E195_R | N | | |
| TJP2_P330_R | Y | | |
| IGFBP7_P297_F | Y | | |
| GSTP1_P74_F | Y | | |
| GSTP1_seq_38_S153_R | Y | | |
| RARA_P176_R | N | | |
| RARB_E114_F | Y | | |
| NEU1_P745_F | Y | | |
| ADAMTS12_E52_R | Y | | |
| TRIP6_E33_F | Y | | |
| SERPINE1_E189_R | Y | | |
| SEPT9_P374_F | Y | | |
| MFAP4_P197_F | N | | |
| ADAMTS12_P250_R | Y | | |
| CFTR_P372_R | Y | | |
| KIT_P367_R | Y | | |
| PDGFRB_P343_F | Y | | |
| TERT_P360_R | Y | | |
| GSTM2_P453_R | N | | |
| CD40_P372_R | Y | | |
| HFE_E273_R | Y | | |
| RASSF1_E116_F | Y | | |
| HHIP_E94_F | Y | | |
| TBX1_P885_R | Y | | |
| NOTCH4_E4_F | N | | |
| FGF2_P229_F | Y | | |
| HDAC9_E38_F | N | | |
| SPARC_P195_F | N | | |
| CD9_P585_R | Y | | |
| KIT_P405_F | Y | | |
| APC_E117_R | Y | | |
| RBP1_P426_R | Y | | |
| HDAC9_P137_R | N | | |
| EYA4_E277_F | Y | | |
| SERPINE1_P519_F | N | | |
| GADD45A_P737_R | N | | |
| NGFR_P355_F | Y | | |
| COL1A2_E299_F | Y | | |

TABLE 6A-continued

List of CpG sites with specific differential hypermethylation and hypomethylation in prostate cancer. CpG island associated (CGI): Yes (Y) or not (N).

| Prostate cancer (hypermethylation) (n: 76) | CGI | Prostate cancer (hypomethylation) (n: 4) | CGI |
|---|---|---|---|
| PTGS2_P524_R | Y | | |
| APC_P280_R | Y | | |
| SPARC_E50_R | Y | | |
| SLC14A1_P369_R | N | | |
| SNCG_E119_F | N | | |
| CDKN1B_P1161_F | N | | |
| CSPG2_P82_R | Y | | |
| PTCH2_E173_F | Y | | |
| PYCARD_P150_F | Y | | |
| CCND2_P887_F | Y | | |
| KLK10_P268_R | N | | |
| TMEFF1_P626_R | Y | | |
| TRIM29_P261_F | N | | |
| PYCARD_E87_F | Y | | |
| PYCARD_P393_F | N | | |
| CCND2_P898_R | Y | | |
| LEFTY2_P561_F | N | | |
| CHI3L2_E10_F | N | | |
| CD9_P504_F | Y | | |
| VIM_P811_R | Y | | |
| CDH13_E102_F | Y | | |
| RARA_E128_R | N | | |
| IFNGR2_P377_R | Y | | |
| TEK_E75_F | N | | |
| SLC14A1_E295_F | N | | |
| SLC5A5_E60_F | Y | | |

TABLE 6B

List of CpG sites with highly specific differential hypermethylation in prostate cancer. CpG island associated (CGI): Yes (Y) or not (N).

| Prostate cancer (hypermethylation) (n: 28) | CGI |
|---|---|
| RARB_P60_F | Y |
| PDGFRB_P273_F | Y |
| PDGFRB_E195_R | N |
| GSTP1_P74_F | Y |
| GSTP1_seq_38_S153_R | Y |
| RARB_E114_F | Y |
| NEU1_P745_F | Y |
| TRIP6_E33_F | Y |
| SERPINE1_E189_R | Y |
| PDGFRB_P343_F | Y |
| HFE_E273_F | Y |
| HHIP_E94_F | Y |
| HDAC9_E38_F | N |
| HDAC9_P137_R | N |
| GADD45A_P737_R | N |
| NGFR_P355_F | Y |
| APC_P280_R | Y |
| SPARC_E50_R | Y |
| CDKN1B_P1161_F | N |
| PTCH2_E173_F | Y |
| KLK10_P268_R | N |
| TMEFF1_P626_R | Y |
| PYCARD_E87_F | Y |
| PYCARD_P393_F | N |
| VIM_P811_R | Y |
| RARA_E128_R | N |
| SLC14A1_E295_F | N |
| SLC5A5_E60_F | Y |

In another embodiment of the first method of the invention, the methylation profile is determined by determining the methylation status in one or more CpG sites as defined in Table 7A or in Table 7B and the resulting methylation profile is compared with the methylation profile in same CpG sites in a DNA sample from a glioma.

TABLE 7A

List of CpG sites with specific differential hypermethylation and hypomethylation in glioma. CpG island associated (CGI): Yes (Y) or not (N).

| Glioma hypermethylation (n: 66) | CGI | Glioma hypomethylation (n: 64) | CGI |
|---|---|---|---|
| FZD9_E458_F | Y | MPO_P883_R | N |
| HOXA11_P698_F | Y | IL8_E118_R | N |
| TES_P182_F | Y | NOTCH4_E4_F | N |
| HOXA9_E252_R | Y | CASP10_P334_F | N |
| CD81_P272_R | Y | SERPINE1_P519_F | N |
| HTR1B_E232_R | Y | MMP14_P13_F | Y |
| TNFRSF10A_P171_F | Y | CCL3_E53_R | N |
| TNFRSF10A_P91_F | Y | CASP10_P186_F | N |
| HOXA9_P1141_R | Y | S100A2_E36_R | N |
| TES_E172_F | Y | HLA-DPA1_P205_R | N |
| TAL1_P594_F | Y | MMP9_P189_F | N |
| HTR1B_P222_F | Y | JAK3_P1075_R | N |
| FLT3_E326_R | Y | TRIP6_P1090_F | Y |
| AHR_P166_R | Y | PTHR1_P258_F | N |
| GATA6_P21_R | Y | TRIP6_P1274_R | Y |
| MEST_E150_F | Y | PADI4_P1011_R | N |
| IRAK3_E130_F | Y | MMP2_P303_R | Y |
| PENK_E26_F | Y | CSF3R_P8_F | N |
| MOS_E60_R | Y | S100A2_P1186_F | N |
| NEFL_P209_R | Y | SH3BP2_E18_F | N |
| HOXA11_E35_F | Y | GSTM2_E153_F | Y |
| NPY_P295_F | Y | EMR3_P39_R | N |
| GATA6_P726_F | Y | PSCA_E359_F | N |
| TNFRSF10D_E27_F | Y | HDAC1_P414_R | Y |
| DSC2_E90_F | Y | CASP10_E139_F | N |
| HOXA5_E187_F | Y | PRSS1_E45_R | N |
| DIO3_P674_F | Y | ALPL_P433_F | Y |
| ALOX12_E85_R | Y | RIPK3_P24_F | N |
| ISL1_P379_F | Y | EMR3_E61_F | N |
| TFAP2C_P765_F | Y | RIPK3_P124_F | N |
| IRAK3_P13_F | Y | TMPRSS4_P552_F | N |
| MEST_P62_R | Y | HLA-DPA1_P28_R | N |
| IRAK3_P185_F | Y | GFAP_P1214_F | N |
| PCTK1_E77_R | Y | LEFTY2_P561_F | N |
| GFI1_P45_R | Y | STAT5A_P704_R | N |
| NPY_E31_R | Y | CD86_P3_F | N |
| DIO3_E230_R | Y | TNFSF10_E53_F | N |
| DDIT3_P1313_R | Y | NOS2A_P288_R | N |
| FLT3_P302_F | Y | KLK11_P103_R | N |
| MEST_P4_F | Y | FGFR2_P460_R | Y |
| IPF1_P750_F | Y | SPDEF_P6_R | N |
| TUSC3_E29_R | Y | STAT5A_E42_F | N |
| BCR_P346_F | Y | VAV1_P317_F | N |
| FZD9_P175_F | Y | DSG1_P159_R | N |
| HOXA9_P303_F | Y | FAS_P322_R | N |
| IPF1_P234_F | Y | SPP1_E140_R | N |
| DNAJC15_P65_F | Y | CHI3L2_E10_F | N |
| PALM2-AKAP2_P420_R | Y | PGR_P790_F | N |
| MDR1_seq_42_S300_R | Y | TNFSF8_P184_F | Y |
| PRKCDBP_E206_F | Y | TJP2_P518_F | Y |
| AHR_E103_F | Y | GSTM2_P453_R | N |
| RASSF1_E116_F | Y | ITK_P114_F | N |
| MYOD1_E156_F | Y | CPA4_E20_F | N |
| DSP_P36_F | Y | PI3_P1394_R | N |
| ISL1_E87_R | Y | MPO_E302_R | N |
| TAL1_E122_F | Y | ACVR1_P983_F | N |
| ICA1_P72_R | Y | GSTM2_P109_R | N |
| IGFBP1_P12_R | Y | LTB4R_E64_R | N |
| RARA_P176_R | N | CCR5_P630_R | N |
| DIO3_P90_F | Y | KRT1_P798_R | N |
| WRN_P969_F | Y | AOC3_P890_R | N |
| PENK_P447_R | Y | IL10_P85_F | N |
| TERT_P360_R | Y | SPI1_E205_F | Y |
| SOX17_P287_R | Y | IFNG_E293_F | N |
| SFRP1_P157_F | Y | | |
| WT1_P853_F | Y | | |

TABLE 7B

List of CpG sites with highly-specific differential hypermethylation and hypomethylation in glioma. CpG island associated (CGI): Yes (Y) or not (N).

| Glioma (hypermethylation) (n: 15) | CGI | Glioma (hypomethylation) (n: 29) | CGI |
|---|---|---|---|
| TES_P182_F | Y | IL8_E118_R | N |
| TNFRSF10A_P171_F | Y | CASP10_P334_F | N |
| TNFRSF10A_P91_F | Y | SERPINE1_P519_F | N |
| TES_E172_F | Y | MMP14_P13_F | Y |
| AHR_P166_R | Y | CASP10_P186_F | N |
| MEST_E150_F | Y | MMP9_P189_F | N |
| PCTK1_E77_R | Y | SH3BP2_E18_F | N |
| GFI1_P45_R | Y | GSTM2_E153_F | Y |
| MEST_P4_F | Y | CASP10_E139_F | N |
| DNAJC15_P65_F | Y | ALPL_P433_F | Y |
| AHR_E103_F | Y | RIPK3_P24_F | N |
| DSP_P36_F | Y | GFAP_P1214_F | N |
| TAL1_E122_F | Y | STAT5A_P704_R | N |
| ICA1_P72_R | Y | CD86_P3_F | N |
| WRN_P969_F | Y | TNFSF10_E53_F | N |
|  |  | FGFR2_P460_R | Y |
|  |  | SPDEF_P6_R | N |
|  |  | STAT5A_E42_F | N |
|  |  | VAV1_P317_F | N |
|  |  | FAS_P322_R | N |
|  |  | SPP1_E140_R | N |
|  |  | CHI3L2_E10_F | N |
|  |  | TJP2_P518_F | N |
|  |  | GSTM2_P453_R | N |
|  |  | ACVR1_P983_F | N |
|  |  | GSTM2_P109_R | N |
|  |  | LTB4R_E64_R | N |
|  |  | IL10_P85_F | N |
|  |  | SPI1_E205_F | Y |

In another embodiment of the first method of the invention, the methylation profile is determined by determining the methylation status in one or more CpG sites as defined in Table 8A or in Table 8B and the resulting methylation profile is compared with the methylation profile in same CpG sites in a DNA sample from an ovarian cancer.

TABLE 8A

List of CpG sites with specific differential hypermethylation and hypomethylation in ovarian cancer. CpG island associated (CGI): Yes (Y) or not (N).

| Ovarian cancer hypermethylation (n: 40) | CGI | Ovarian cancer hypomethylation (n: 16) | CGI |
|---|---|---|---|
| CFTR_P372_R | Y | MEST_P4_F | Y |
| HCK_P858_F | Y | PI3_E107_F | N |
| MOS_E60_R | Y | NBL1_P24_F | N |
| HOXA9_E252_R | Y | PTPN6_P282_R | N |
| TAL1_P594_F | Y | WEE1_P924_R | N |
| DIO3_P674_F | Y | S100A2_P1186_F | N |
| PENK_E26_F | Y | NID1_P677_F | N |
| SOX1_P294_F | Y | CTLA4_E176_R | N |
| LEFTY2_P561_F | N | GLI2_E90_F | N |
| CALCA_E174_R | Y | MST1R_E42_R | Y |
| THY1_P149_R | Y | GPATC3_P410_R | N |
| HOXA11_P698_F | Y | TRIM29_E189_F | Y |
| ALOX12_P223_R | Y | GLI2_P295_F | Y |
| DIO3_P90_F | Y | EMR3_E61_F | N |
| GLI3_P453_R | Y | MSH2_P1008_F | Y |
| ATP10A_P147_F | Y | IFNG_E293_F | N |
| ASCL1_P747_F | Y |  |  |
| MFAP4_P10_R | N |  |  |
| HS3ST2_E145_R | Y |  |  |
| ALOX12_E85_R | Y |  |  |
| DCC_E53_R | Y |  |  |
| HS3ST2_P171_F | Y |  |  |
| FRZB_E186_R | Y |  |  |
| THY1_P20_R | Y |  |  |
| TNFRSF10C_P7_F | Y |  |  |
| HOXA9_P303_F | Y |  |  |
| DDR2_P743_R | N |  |  |
| RASSF1_P244_F | Y |  |  |
| DBC1_P351_R | Y |  |  |
| MFAP4_P197_F | N |  |  |
| ZNF215_P71_R | Y |  |  |
| EPHA5_P66_F | Y |  |  |
| HCK_P46_R | Y |  |  |
| MMP2_P303_R | Y |  |  |
| CYP1B1_E83_R | Y |  |  |
| PITX2_E24_R | Y |  |  |
| ZNF215_P129_R | Y |  |  |
| TSP50_P137_F | Y |  |  |
| SEPT9_P374_F | Y |  |  |
| SEPT5_P441_F | Y |  |  |

TABLE 8B

List of CpG sites with highly specific differential hypermethylation and hypomethylation in ovarian cancer. CpG island associated (CGI): Yes (Y) or not (N).

| Ovarian cancer* (n: 3) | CGI | Ovarian cancer* (n: 4) | CGI |
|---|---|---|---|
| GLI3_P453_R | Y | WEE1_P924_R | N |
| THY1_P20_R | Y | CTLA4_E176_R | N |
| DDR2_P743_R | N | GPATC3_P410_R | N |
|  |  | MSH2_P1008_F | Y |

In another embodiment of the first method of the invention, the methylation profile is determined by determining the methylation status in one or more CpG sites as defined in Table 9A or in Table 9B and the resulting methylation profile is compared with the methylation profile in same CpG sites in a DNA sample from a lung cancer.

TABLE 9A

List of CpG sites with specific differential hypermethylation and hypomethylation in lung cancer. CpG island associated (CGI): Yes (Y) or not (N).

| Lung cancer hypermethylation (n: 39) | CGI | Lung cancer hypomethylation (n: 1) | CGI |
|---|---|---|---|
| HOXA9_E252_R | Y | SPI1_P48_F | N |
| MOS_E60_R | Y |  |  |
| HS3ST2_E145_R | Y |  |  |
| EYA4_P794_F | Y |  |  |
| TAL1_P594_F | Y |  |  |
| STAT5A_E42_F | N |  |  |
| HOXA9_P1141_R | Y |  |  |
| TPEF_seq_44_S88_R | Y |  |  |
| FZD9_E458_F | Y |  |  |
| DIO3_P90_F | Y |  |  |
| FRZB_E186_R | Y |  |  |
| HCK_P858_F | Y |  |  |
| DLK1_E227_R | Y |  |  |
| JAK3_P156_R | N |  |  |
| NOTCH4_E4_F | N |  |  |
| ASCL2_P609_R | Y |  |  |
| HOXA11_P698_F | Y |  |  |
| SOX17_P287_R | Y |  |  |
| PENK_E26_F | Y |  |  |
| HS3ST2_P171_F | Y |  |  |
| HTR1B_E232_R | Y |  |  |
| GP1BB_P278_R | Y |  |  |

TABLE 9A-continued

List of CpG sites with specific differential hypermethylation and hypomethylation in lung cancer. CpG island associated (CGI): Yes (Y) or not (N).

| Lung cancer hypermethylation (n: 39) | CGI | Lung cancer hypomethylation (n: 1) | CGI |
|---|---|---|---|
| SOX1_P294_F | Y | | |
| POMC_P400_R | Y | | |
| CFTR_P372_R | Y | | |
| FGF2_P229_F | Y | | |
| CDH13_P88_F | Y | | |
| RBP1_P426_R | Y | | |
| CALCA_E174_R | Y | | |
| CSPG2_P82_R | Y | | |
| APC_P14_F | Y | | |
| ZNF215_P71_R | Y | | |
| CHGA_E52_F | Y | | |
| HOXB13_P17_R | Y | | |
| COL1A2_E299_F | Y | | |
| TJP2_P518_F | Y | | |
| GAS7_E148_F | Y | | |
| TBX1_P885_R | Y | | |
| GSTM2_E153_F | Y | | |

TABLE 9B

List of CpG sites with highly specific differential hypermethylation and hypomethylation in lung cancer. CpG island associated (CGI): Yes (Y) or not (N).

| Lung cancer* (n: 2) | CGI | Lung cancer* (n: 1) | CGI |
|---|---|---|---|
| JAK3_P156_R | N | SPI1_P48_F | N |
| GP1BB_P278_R | Y | | |

In another embodiment of the first method of the invention, the methylation profile is determined by determining the methylation status in one or more CpG sites as defined in Table 10A or in Table 10B and the resulting methylation profile is compared with the methylation profile in same CpG sites in a DNA sample from a bladder cancer.

TABLE 10A

List of CpG sites with specific differential hypermethylation and hypomethylation in bladder cancer. CpG island associated (CGI): Yes (Y) or not (N).

| Bladder cancer hypermethylation (n: 36) | CGI | Bladder cancer hypomethylation (n: 80) | CGI |
|---|---|---|---|
| HOXA9_E252_R | Y | TRIM29_P261_F | N |
| HOXA11_P698_F | Y | PI3_E107_F | N |
| TJP2_P330_R | Y | CEACAM1_P44_R | N |
| TJP2_P518_F | Y | IFNG_E293_F | N |
| PENK_E26_F | Y | NOS2A_E117_R | N |
| CYP1B1_E83_R | Y | NOS3_P38_F | N |
| WT1_P853_F | Y | PSCA_P135_F | N |
| TAL1_P594_F | Y | PTPRH_P255_F | N |
| DLK1_E227_R | Y | TMPRSS4_E83_F | N |
| SLIT2_P208_F | Y | SRC_E100_R | N |
| HOXA9_P303_F | Y | CDH17_P376_F | N |
| FLT3_E326_R | Y | AATK_E63_R | N |
| SOX17_P287_R | Y | THBS2_P605_R | N |
| PENK_P447_R | Y | CDH17_E31_F | N |
| NPY_E31_R | Y | KRT5_E196_R | Y |
| NPY_P295_F | Y | P2RX7_P597_F | N |
| SOX1_P294_F | Y | IL1RN_E42_F | N |
| CDH11_P354_R | Y | AIM2_P624_F | N |
| TPEF_seq_44_S88_R | Y | NBL1_P24_F | N |
| MYOD1_E156_F | Y | PI3_P274_R | N |
| HOXA11_E35_F | Y | NID1_P677_F | N |
| LEFTY2_P561_F | N | SERPINB5_P19_R | Y |
| GSTM1_P266_F | Y | S100A2_P1186_F | N |
| SLIT2_E111_R | Y | SLC14A1_E295_F | N |
| HS3ST2_E145_R | Y | CLDN4_P1120_R | N |
| GSTM1_P363_F | Y | EMR3_E61_F | N |
| TERT_P360_R | Y | PTPRH_E173_F | N |
| HS3ST2_P171_F | Y | BCR_P422_F | Y |
| PITX2_E24_R | Y | TRIM29_P135_F | N |
| TERT_E20_F | Y | EMR3_P39_R | N |
| NPR2_P618_F | Y | VAMP8_P114_F | N |
| NEFL_P209_R | Y | MST1R_E42_R | Y |
| ISL1_P554_F | Y | PTPN6_P282_R | N |
| TWIST1_P355_R | Y | TRPM5_P979_F | N |
| HIC-1_seq_48_S103_R | Y | IGFBP1_P12_R | Y |
| SOX1_P1018_R | Y | VAMP8_E7_F | N |
| | | SFN_E118_F | Y |
| | | TFF2_P178_F | N |
| | | IGFBP1_E48_R | Y |
| | | EDNRB_P709_R | N |
| | | GPR116_E328_R | N |
| | | CXCL9_E268_R | N |
| | | VAMP8_P241_F | N |
| | | UGT1A1_P315_R | N |
| | | PGR_P790_F | N |
| | | GLI2_P295_F | Y |
| | | CASP8_E474_F | N |
| | | GABRA5_P862_R | N |
| | | TRIP6_P1090_F | Y |
| | | AIM2_E208_F | N |
| | | NID1_P714_R | N |
| | | HDAC1_P414_R | Y |
| | | TIMP1_P615_R | N |
| | | BRCA1_P835_R | Y |
| | | PTK6_E50_F | Y |
| | | ARHGDIB_P148_R | N |
| | | PRSS8_E134_R | Y |
| | | VAV1_E9_F | Y |
| | | KRT13_P341_R | N |
| | | OSM_P188_F | Y |
| | | GABRA5_P1016_F | N |
| | | RIPK3_P124_F | N |
| | | TRIM29_E189_F | Y |
| | | CSF1R_E26_F | N |
| | | JAK3_P1075_R | N |
| | | NBL1_E205_R | N |
| | | LCN2_P86_R | N |
| | | MMP19_E274_R | N |
| | | GLI2_E90_F | N |
| | | ZP3_P220_F | N |
| | | MMP10_E136_R | N |
| | | HPN_P823_F | N |
| | | AFF3_P122_F | N |
| | | SRC_P164_F | N |
| | | PADI4_E24_F | N |
| | | CAPG_E228_F | N |
| | | MAPK10_E26_F | N |
| | | SFTPA1_E340_R | N |
| | | PSCA_E359_F | N |
| | | APBA2_P305_R | N |

TABLE 10B

List of CpG sites with specific differential hypermethylation and hypomethylation in bladder cancer. CpG island associated (CGI): Yes (Y) or not (N).

| Bladder cancer (hypermethylation) (n: 2) | CGI | Bladder cancer (hypomethylation) (n: 27) | CGI |
|---|---|---|---|
| TERT_E20_F | Y | TMPRSS4_E83_F | N |
| NPR2_P618_F | Y | SRC_E100_R | N |
| | | CDH17_P376_F | N |

TABLE 10B-continued

List of CpG sites with specific differential hypermethylation and hypomethylation in bladder cancer. CpG island associated (CGI): Yes (Y) or not (N).

| Bladder cancer (hypermethylation) (n: 2) | CGI | Bladder cancer (hypomethylation) (n: 27) | CGI |
|---|---|---|---|
| | | THBS2_P605_R | N |
| | | CDH17_E31_F | N |
| | | KRT5_E196_R | Y |
| | | P2RX7_P597_F | N |
| | | AIM2_P624_F | N |
| | | SLC14A1_E295_F | N |
| | | BCR_P422_F | Y |
| | | VAMP8_P114_F | N |
| | | TRPM5_P979_F | N |
| | | IGFBP1_P12_R | Y |
| | | VAMP8_E7_F | N |
| | | IGFBP1_E48_R | Y |
| | | EDNRB_P709_R | N |
| | | GPR116_E328_R | N |
| | | NID1_P714_R | N |
| | | TIMP1_P615_R | N |
| | | ARHGDIB_P148_R | N |
| | | KRT13_P341_R | N |
| | | GABRA5_P1016_F | N |
| | | CSF1R_E26_F | N |
| | | MMP19_E274_R | N |
| | | HPN_P823_F | N |
| | | PADI4_E24_F | N |
| | | MAPK10_E26_F | N |

In another embodiment of the first method of the invention, the methylation profile is determined by determining the methylation status in one or more CpG sites as defined in Table 11A or in Table 11B and the resulting methylation profile is compared with the methylation profile in same CpG sites in a DNA sample from a melanoma.

TABLE 11A

List of CpG sites with specific differential hypermethylation and hypomethylation in melanoma. CpG island associated (CGI): Yes (Y) or not (N).

| Melanoma hypermethylation (n: 28) | CGI | Melanoma hypomethylation (n: 5) | CGI |
|---|---|---|---|
| ALOX12_P223_R | Y | EVI2A_P94_R | N |
| ALOX12_E85_R | Y | IFNG_E293_F | N |
| MET_E333_F | Y | PI3_P1394_R | N |
| SNCG_E119_F | N | TNFSF8_P184_F | Y |
| GRB7_E71_R | N | VAV1_E9_F | Y |
| AATK_P709_R | Y | | |
| DDR1_P332_R | N | | |
| DHCR24_P652_R | N | | |
| SNCG_P53_F | Y | | |
| RARA_P176_R | N | | |
| IL1RN_P93_R | N | | |
| TGFB3_E58_R | N | | |
| TNFRSF10D_E27_F | Y | | |
| STAT5A_P704_R | N | | |
| COL1A2_P407_R | N | | |
| POMC_P400_R | Y | | |
| IGFBP5_P9_R | Y | | |
| SNCG_P98_R | Y | | |
| BMP4_P123_R | Y | | |
| CYP1B1_E83_R | Y | | |
| KCNK4_E3_F | Y | | |
| IL17RB_P788_R | Y | | |
| IL6_E168_F | N | | |
| BMP4_P199_R | Y | | |
| S100A2_P1186_F | N | | |
| FRZB_E186_R | Y | | |
| TRIP6_P1090_F | Y | | |
| LCN2_P86_R | N | | |

TABLE 11B

List of CpG sites with highly specific differential hypermethylation and hypomethylation in melanoma. CpG island associated (CGI): Yes (Y) or not (N).

| Melanoma (hypermethylation) (n: 4) | CGI | Melanoma (hypermethylation) (n: 1) | CGI |
|---|---|---|---|
| MET_E333_F | Y | EVI2A_P94_R | N |
| COL1A2_P407_R | N | | |
| IL17RB_P788_R | Y | | |
| IL6_E168_F | N | | |

In another embodiment of the first method of the invention, the methylation profile is determined by determining the methylation status in one or more CpG sites as defined in Table 12A or in Table 12B and the resulting methylation profile is compared with the methylation profile in same CpG sites in a DNA sample from breast cancer.

TABLE 12A

List of CpG sites with specific differential hypermethylation and hypomethylation in breast cancer. CpG island associated (CGI): Yes (Y) or not (N).

| Breast cancer (hypomethylation) (n: 18) | CGI | Breast cancer (hypomethylation) (n: 1) | CGI |
|---|---|---|---|
| CFTR_P372_R | Y | PI3_E107_F | N |
| HOXA9_E252_R | Y | | |
| RBP1_P426_R | Y | | |
| TNFRSF10D_E27_F | Y | | |
| MME_E29_F | Y | | |
| TSP50_P137_F | Y | | |
| TERT_P360_R | Y | | |
| APC_P14_F | Y | | |
| GSTP1_E322_R | Y | | |
| RASSF1_E116_F | Y | | |
| SOX1_P294_F | Y | | |
| SOX17_P287_R | Y | | |
| MOS_E60_R | Y | | |
| CDH13_P88_F | Y | | |
| APC_E117_R | Y | | |
| BMP4_P123_R | Y | | |
| IRAK3_P185_F | Y | | |
| IGFBP3_P423_R | Y | | |

In another embodiment of the first method of the invention, the methylation profile is determined by determining the methylation status in one or more CpG sites as defined in Table 13A or in Table 13B and the resulting methylation profile is compared with the methylation profile in same CpG sites in a DNA sample from a myeloid neoplasia.

TABLE 13A

List of CpG sites with specific differential hypermethylation and hypomethylation in myeloid neoplasias. CpG island associated (CGI): Yes (Y) or not (N).

| Myeloid neoplasias hypermethylation (n: 15) | CGI | Myeloid neoplasias hypomethylation (n: 2) | CGI |
|---|---|---|---|
| FOSL2_E384_R | Y | TRIP6_P1274_R | Y |
| PTPN6_P282_R | N | LMO2_E148_F | N |
| FZD9_E458_F | Y | | |
| HS3ST2_E145_R | Y | | |
| DBC1_P351_R | Y | | |
| HIC-1_seq_48_S103_R | Y | | |
| EPHB1_E202_R | Y | | |
| MOS_E60_R | Y | | |
| DBC1_E204_F | Y | | |
| MYOD1_E156_F | Y | | |

TABLE 13A-continued

List of CpG sites with specific differential hypermethylation and hypomethylation in myeloid neoplasias. CpG island associated (CGI): Yes (Y) or not (N).

| Myeloid neoplasias hypermethylation (n: 15) | CGI | Myeloid neoplasias hypomethylation (n: 2) | CGI |
|---|---|---|---|
| BAX_E281_R | Y | | |
| CFTR_P372_R | Y | | |
| DIO3_P674_F | Y | | |
| CDH11_P354_R | Y | | |
| IGSF4C_E65_F | Y | | |

TABLE 13B

List of CpG site with specific differential hypermethylation and hypomethylation in myeloid neoplasias. CpG island associated (CGI): Yes (Y) or not (N).

| Myeloid neoplasias (n: 1) | CGI | Myeloid neoplasias (n: 1) | CGI |
|---|---|---|---|
| IGSF4C_E65_F | Y | LMO2_E148_F | N |

In another embodiment of the first method of the invention, the methylation profile is determined by determining the methylation status in one or more CpG sites as defined in Table 14A or in Table 14B and the resulting methylation profile is compared with the methylation profile in same CpG sites in a DNA sample from a testicular cancer.

TABLE 14A

List of CpG sites with specific differential hypermethylation in testicular cancer (n: 10). CpG island associated (CGI): Yes (Y) or not (N).

| Testicular cancer hypermethylation (n: 10) | CGI |
|---|---|
| BCR_P346_F | Y |
| SEPT5_P464_R | Y |
| GSTM1_P363_F | Y |
| IPF1_P750_F | Y |
| BCR_P422_F | Y |
| HOXA5_E187_F | Y |
| TBX1_P520_F | N |
| HIC-1_seq_48_S103_R | Y |
| ARHGDIB_P148_R | N |
| GPATC3_P410_R | N |

TABLE 14B

List of CpG sites with highly-specific differential hypermethylation in testicular cancer (n: 10). CpG island associated (CGI): Yes (Y) or not (N).

| Testis cancer (hypermethylation) (n: 2) | CGI | Testis cancer (hypomethylation) (n: 1) | CGI |
|---|---|---|---|
| TBX1_P520_F | N | H19_P1411_R | Y |
| GPATC3_P410_R | N | | |

In another embodiment of the first method of the invention, the methylation profile is determined by determining the methylation status in one or more CpG sites as defined in Table 15A or in Table 15B and the resulting methylation profile is compared with the methylation profile in same CpG sites in a DNA sample from a stomach cancer.

TABLE 15A

List of CpG sites with specific differential hypermethylation and hypomethylation in stomach cancer (n: 10). CpG island associated (CGI): Yes (Y) or not (N).

| Stomach cancer hypermethylation (n: 7) | CGI | Stomach cancer hypomethylation (n: 2) | CGI |
|---|---|---|---|
| GAS7_E148_F | Y | TNFSF8_P184_F | Y |
| TGFB3_E58_R | N | CSF3R_P8_F | N |
| SFRP1_P157_F | Y | | |
| SOX1_P294_F | Y | | |
| MDR1_seq_42_S300_R | Y | | |
| HS3ST2_E145_R | Y | | |
| CCKAR_P270_F | N | | |

TABLE 15B

List of CpG sites with highly specific differential hypermethylation in stomach cancer (n: 1). CpG island associated (CGI): Yes (Y) or not (N).

| Stomach cancer (hypermethylation) (n: 1) | CGI |
|---|---|
| CCKAR_P270_F | N |

Once the methylation profile of the CUP and of one or more primary tumors have been compared, the CUP is identified as deriving from a given primary tumor wherein a substantial identity is found between the methylation profile obtained in step (i) and the methylation profile of said primary tumor. It will be understood that the methylation profile of the CUP can be compared with the methylation profile of the primary tumors in a recursive or sequential manner (the methylation profile of the CUP is compared with the methylation profile of a first primary tumor and if no substantial identity is found, then the methylation profile of the CUP is compared with the me methylation profile of a second primary tumor and so consecutively until a primary tumor is found the methylation profile of which shows a substantial identity with the methylation profile of the CUP). Alternatively, the methylation profile of the CUP can be compared with all entries in a dataset of methylation profiles from a collection of primary tumors, and select the primary tumor which shows a methylation profile showing a substantial identity with the methylation profile of the CUP.

The comparison of the methylation profiles and the correlation between the identity of the profiles and the determination of the origin of the CUP can be done using any appropriate state of the art mathematical method. Well-known mathematical methods for establishing correlation between datasets employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA). Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis.

Details relating to these statistical methods are found in the following references: Ruczinski et al., 12 J. OF COMPUTATIONAL AND GRAPHICAL STATISTICS 475-511 (2003); Friedman, J. F L, 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. F L, Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

As will be understood by those skilled in the art, the determination of the origin of the CUP using the method of the invention, although preferred to be, need not be correct for 100% of the CUPs to be diagnosed or evaluated. The term, however, requires that a statistically significant portion of CUPs can be correctly identified. Whether the determination of the origin of a CUP is statistically significant can be determined without further ado by the person skilled in the art using various well known statistic evaluation tools, e.g., determination of confidence intervals, p-value determination, cross-validated classification rates and the like etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.01, 0.005 or lower.

The performance of the method according to the invention for the identification of the origin of a CUP is typically assessed using statistical measures. The performance of the characterization can be assessed by measuring sensitivity, specificity and related measures. A true positive is a subject with a characteristic, e.g., a disease or disorder, correctly identified as having the characteristic. A false positive is a subject without the characteristic that the test improperly identifies as having the characteristic. A true negative is a subject without the characteristic that the test correctly identifies as not having the characteristic. A false negative is a person with the characteristic that the test improperly identifies as not having the characteristic. The ability of the test to distinguish between these classes provides a measure of test performance.

The specificity of a test is defined as the number of true negatives divided by the number of actual negatives (i.e., sum of true negatives and false positives). Specificity is a measure of how many subjects are correctly identified as negatives. A specificity of 100 percent means that the test recognizes all actual negatives—for example, all healthy people will be recognized as healthy. A lower specificity indicates that more negatives will be determined as positive.

The sensitivity of a test is defined as the number of true positives divided by the number of actual positives (i.e., sum of true positives and false negatives). Specificity is a measure of how many subjects are correctly identified as positives. A sensitivity of 100 percent means that the test recognizes all actual positives—for example, all sick people will be recognized as sick. A lower sensitivity indicates that more positives will be missed by being determined as negative.

The accuracy of a test is defined as the number of true positives and true negatives divided by the sum of all true and false positives and all true and false negatives. It provides one number that combines sensitivity and specificity measurements.

The method according to the present invention can be used to characterize the origin of a CUP with at least 50, 51, 52, 53, 54, 55, 56, 57, 58, 59, 60, 61, 62, 63, 64, 65, 66, 67, 68, 69, or 70 percent sensitivity, such as with at least 71, 72, 73, 74, 75, 76, 77, 78, 79, 80, 81, 82, 83, 84, 85, 86, or 87 percent sensitivity. In some embodiments, the phenotype is characterized with at least 87.1, 87.2, 87.3, 87.4, 87.5, 87.6, 87.7, 87.8, 87.9, 88.0, or 89 percent sensitivity, such as at least 90 percent sensitivity. The phenotype can be characterized with at least 91, 92, 93, 94, 95, 96, 97, 98, 99 or 100 percent sensitivity.

The method according to the present invention can be used to characterize the origin of a CUP with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, or 97 percent specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100 percent specificity.

In another embodiment, the method of the invention further comprises the determination in the CUP of the methylation status of CpG sites which are indicative of a chemosensity to different drugs. This would allow not only the identification of the origin of the CUP but also to decide on therapeutic strategies for the CUP. Suitable CpG sites which can be used according to the present invention include, without limitation, MGMT-temodal/dacarbazine (Esteller, New England Journal of Medicine 2000; Oaz et al., Clin Cancer Res 2004, etc), WRN-irinotecan/topotecan (Agrelo et al., Proc Natl Acad Sci USA 2006) and BRCA1-Oxaliplatin/Cisplatin/PARP Inhibitors (Veeck et al., Journal of Clinical Oncology 2010).

Methods for Selecting a Therapy for a Cancer of Unknown Primary Origin (CUP)

The methods disclosed in the present invention are useful for determining the origin of a CUP. Since CUPs are therapeutically targeted using a therapy which is used for the primary tumor, the identification of the origin of the CUP will allow the design of specific therapies for the CUP based on the nature of the primary tumor.

Thus, in another aspect, the invention relates to a method for selecting a therapy for a cancer of unknown primary origin (CUP) (hereinafter second method of the invention) comprising the steps of:
(i) determining the methylation profile in a selected region of a DNA isolated from said CUP and
(ii) comparing the methylation profile of said selected region with the methylation profile of the same region in a DNA sample isolated from at least one primary tumor wherein a substantial identity between the methylation profile obtained in (i) and the methylation profile of the primary tumor is indicative that the CUP is to be treated with a therapy which is suitable for said primary tumor.

Steps (i) and (ii) are carried out essentially as described in the first method of the invention.

In a preferred embodiment, the primary tumor is selected from the group consisting of a lymphoid neoplasia, head and neck cancer, pancreatic cancer, endometrial cancer, colon cancer, prostate cancer, glioma, ovarian cancer, lung cancer, bladder cancer, melanoma, breast cancer, a myeloid neoplasia, testicular cancer, stomach cancer.

In a preferred embodiment, the determination of the methylation profile according to the second method of the invention comprises the determination of the methylation status in one or more CpG sites as defined in Tables 1 to 15 wherein
(i) the methylation status in one or more CpG sites as defined in Table 1A or in Table 1B is compared with the methylation status of a lymphoid neoplasia,
(ii) the methylation status in one or more CpG sites as defined in Table 2A or 2B is compared with the methylation status of a head and neck cancer,
(iii) the methylation status in one or more CpG sites as defined in Table 3A or 3B is compared with the methylation status of a pancreatic cancer,
(iv) the methylation status in one or more CpG sites as defined in Table 4A or 4B is compared with the methylation status of a endometrial cancer,
(v) the methylation status in one or more CpG sites as defined in Table 5A or 5B is compared with the methylation status of a colon cancer,
(vi) the methylation status in one or more CpG sites as defined in Table 6A or 6B is compared with the methylation status of a prostate cancer,
(vii) the methylation status in one or more CpG sites as defined in Table 7A or 7B is compared with the methylation status of a glioma,
(viii) the methylation status in one or more CpG sites as defined in Table 8A or 8B is compared with the methylation status of an ovarian cancer,
(ix) the methylation status in one or more CpG sites as defined in Table 9A or 9B is compared with the methylation status of a lung cancer,
(x) the methylation status in one or more CpG sites as defined in Table 10A or 10B is compared with the methylation status of a bladder cancer,
(xi) the methylation status in one or more CpG sites as defined in Table 11A or 11B is compared with the methylation status of a melanoma,
(xii) the methylation status in one or more CpG sites as defined in Table 12A is compared with the methylation status of a breast cancer,
(xiii) the methylation status in one or more CpG sites as defined in Table 13A or 13B is compared with the methylation status of a myeloid neoplasia,
(xiv) the methylation status in one or more CpG sites as defined in Table 14A or 14B or is compared with the methylation status of a testicular cancer and/or
(xv) the methylation status in one or more CpG sites as defined in Table 15A or 15B is compared with the methylation status of a stomach cancer.

Once the methylation pattern of the CUP has been matched with the methylation pattern of a primary cancer, a therapy is selected which is adequate for said primary cancer. Suitable therapies are shown in Table 16.

TABLE 16

Cancers and corresponding first line chemotherapeutic treatments

| Types of cancer | Therapy |
|---|---|
| Lung cancer | Platinum-based compounds |
| Colon cancer | Antimetabolites |
| Melanoma | Cytokines |
| Pancreatic cancer | Antimetabolites |
| Prostate cancer | Hormonal therapy and mitotic inhibitors for resistant patients |
| Glioma | DNA-alkylating drugs |
| Bladder cancer | Antimetabolites and platinum based compounds |
| Ovarian cancer | If epithelial cancer, platinum-based compounds |
| Hepatobiliary cancer | Antimetabolites or EGFR-targeted drugs |
| Breast cancer | Hormonal therapy alone, hormonal therapy combined with cytostatic cocktails (anthracycline/DNA alkylating drug/antimetabolite) or HER2-targeted drugs |
| Lymphoma | CD20-targeted drugs |
| Head and neck cancer | Mitotic inhibitors (taxol) alone or in combination with Platinum-based compounds (cisplatin) and antimetabolites (5-FU) |
| Endometrial cancer | Hormonal therapy |
| Myeloma | Corticoesteroids, proteasome inhibitors and thalidomide/lenalidomide |
| Testicular cancer | Topoisomerase inhibitor (etoposide) in combination with a platinum-based compound (cisplatin) |
| Stomach cancer | DNA intercalating agents (doxorubicine) and DNA cross-linking agents (Mitomycin C) |

The term "platinum-based compound", as used herein, refers to any compound containing a platinum atom capable of binding and cross-linking DNA, inducing the activation of the DNA repair and ultimately triggering apoptosis. Platinum-based compounds for treating cancer include, without limitation, carboplatin, cisplatin [cis-diamminedichloroplatinum, (CDDP)], oxaliplatin, iproplatin, nedaplatin, triplatin tetranitrate, tetraplatin, satraplatin (JM216), JM118 [cis ammine dichloro (II)], JM149 [cis ammine dichloro (cyclohexylamine) trans dihydroxo platinum (IV)], JM335 [trans ammine dichloro dihydroxo platinum (IV)], transplatin, ZD0473, cis, trans, cis-Pt(NH3)(C6H11NH2)(OOCC3H7)2Cl, malanate-1,2-diaminociclohexanoplatin (II), 5-sulphosalycilate-trans-(1,2-diaminociclohexane)platin (II) (SSP), poly-[(trans-1,2-diaminocyclohexane)platin]-carboxyamilose (POLY-PLAT) and 4-hydroxy-sulphonylphenylacetate (trans-1,2-diaminocyclohexane) platinum (II) (SAP) and the like. In a particular embodiment of the first method of the invention, the platinum-based compound is selected from carboplatin, cisplatin and oxaliplatin; preferably is cisplatin. When the subject suffers from lung cancer or bladder cancer the first line chemotherapeutic treatment is based on platinum-based compounds, preferably cisplatin. When the subject suffers from ovarian cancer, particularly epithelial ovarian cancer, the first line chemotherapeutic treatment is based on platinum-based compounds.

"Antimetabolite", as used herein, relates, in a broad sense, to substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). Antimetabolites suitable for use in the present invention include, without limitation, folic acid antimetabolites (aminopterin, denopterin, methotrexate, edatrexate, trimetrexate, nolatrexed, lometrexol, pemetrexed, raltitrexed, piritrexim, pteropterin, leucovorin, 10-propargyl-5,8-dideazafolate (PDDF, CB3717)), purine analogs (cladribine, clofarabine, fludarabine, mercaptopurine, pentostatin, thioguanine) and pyrimidine analogs (capecitabine, cytarabine or ara-C, decitabine, fluorouracil, 5-fluorouracil, doxifluridine, floxuridine and gemcitabine). In a preferred embodiment the antimetabolite is selected from 5-fluorouracil and gemcitabine. When the subject suffers from colon cancer the first line chemotherapeutic treatment are antimetabolites, preferably 5-fluorouracil. When the subject suffers from pancreatic cancer, bladder cancer or gallbladder cancer the first line chemotherapeutic treatment are antimetabolites, preferably gemcitabine. When the subject suffers from hepatobiliary cancer, the first line chemotherapeutic treatment is based on antimetabolites, preferably based on fluoropyrimidine. Examples of fluoropyrimidines useful in the treatment of hepatobiliary cancer are 5-fluorouracil, tegafur and capecitabine The term "cytokines" refers to immunomodulating agents, such as interleukins and interferons, which are polypeptides secreted by specific cells of the immune system and carrying signals locally between cells. Cytokines suitable for use in the present invention are, without limitation, interferon alpha, interferon beta, interferon gamma, interleukin 2, interleukin 12, tumor necrosis factor, granulocyte macrophage colony-stimulating factor (GM-CSF), granulocyte colony-stimulating factor (G-CSF), interleukin 4 (IL-4), interleukin 6 (IL-6), interleukin 18 (IL-18) and interferon alpha 2b. In a preferred embodiment the cytokine used is interferon. When the subject suffers from melanoma the first line chemotherapeutic treatment in stage III are cytokines, preferably interferon.

The term "hormonal therapy" refers to the administration of an anti-tumour agent that acts primarily by interacting with (e.g. interfering with) a hormonal pathway that is specific or relatively specific to particular cell type(s). Said treatment has for purpose to block, inhibit or reduce the effect of hormones, specifically to block the effect of estrogen or progesterone, or alternatively, lower estrogen or progesterone levels, including anti-estrogen or anti-progesterone therapy and estrogen or progesterone ablation therapy. Hormonal therapy includes, without limitation, tamoxifen, toremifene, anastrozole, arzoxifene, lasofoxifene, raloxifene, nafoxidine, fulvestrant, aminoglutethimide, testolactone, atamestane, exemestane, fadrozole, formestane, letrozole, goserelin, leuprorelin or leuprolide, buserelin, histrelin, megestrol and fluoxymesterone. In a preferred embodiment the hormonal therapy is androgen-deprivation therapy. The term "androgen-deprivation therapy" or "androgen suppression therapy" refers to treatments that reduce the levels of the male hormones, androgens, in the body. Androgen-deprivation therapy includes, without limitation, GnRH agonists such as leuprolide, buserelin, goserelin and histrelin. When the subject suffers from prostate cancer, the first line chemotherapeutic treatment is hormonal therapy, preferably androgen-deprivation therapy. When the subject suffers from breast cancer the first line chemotherapeutic treatment is hormonal therapy alone or hormonal therapy combined with cytostatic cocktails. The term "cytostatic cocktail", in the context of the present invention and related to the treatment of breast cancer, refers to a combination of an anthracycline, a DNA alkylating drug and an antimetabolite. Examples of "cytostatic cocktails", according to the present invention are, without limitation, FAC (adriamycin/cyclophosphamide/5-fluorouracil), FEC (5-fluorouracil/epirubicin/cyclophosphamide) and CNF (cyclophosphamide/mitoxantrone/5-fluorouracil). In a preferred embodiment the cytostatic cocktail is selected from FAC, FEC and CNF.

The term "mitotic inhibitor" refers to compounds which inhibit mitosis or cell division by disrupting microtubules. Examples of mitotic inhibitors include, without limitation, vinca alkaloids such as vindesine, vincristine, vinblastine, vinorelbine; taxanes such as paclitaxel (Taxol™), docetaxel (Taxotere™); colchicine (NSC 757), thiocolchicine (NSC 361792), colchicine derivatives (e. g., NSC 33410), and allocolchicine (NSC 406042); halichondrin B (NSC 609395); dolastatin 10 (NSC 376128); maytansine (NSC 153858); rhizoxin (NSC 332598); epothilone A, epothilone B; discodermolide; estramustine; nocodazole. In a preferred embodiment the mitotic inhibitor is docetaxel. When the subject suffers from prostate cancer, the second line chemotherapeutic treatment for a cancer that is resistant to hormonal therapy is a treatment with mitotic inhibitors, preferably docetaxel.

"DNA-alkylating drugs", as used herein, are alkylating agents used in cancer treatment that are capable of adding an alkyl group to DNA of rapidly dividing cells thus leading to replication arrest and cell death. DNA-alkylating agents are nitrogen mustards, nitrosoureas, ethylenimine derivatives, alkyl sulfonates and triazenes, including, but not limited to, cyclophosphamide (Cytoxan™), busulfan, improsulfan, piposulfan, pipobroman, melphalan (L-sarcolysin), chlorambucil, mechlorethamine or mustine, uramustine or uracil mustard, novembichin, phenesterine, trofosfamide, ifosfamide, carmustine (BCNU), lomustine (CCNU), chlorozotocin, fotemustine, nimustine, ranimnustine, semustine (methyl-CCNU), streptozocin, thiotepa, triethylenemelamine, triethylenethiophosphoramine, procarbazine, altretamine, dacarbazine, mitozolomide and temozolomide. In a preferred embodiment the DNA-alkylating drug is selected from temozolomide, nitrosoureas and procarbazine. When the subject suffers from glioma the first line chemotherapeutic treatment are DNA-alkylating drugs, preferably selected from temozolomide, nitrosoureas, procarbazine and combinations thereof.

The term "EGFR-targeted drug", as used herein, refers to any molecule which is capable of inhibiting totally or partially signaling through EGFR either by targeting the extracellular domain of the receptor and thereby blocking the binding of the ligand to the receptor or by inhibiting the tyrosine kinase activity of the cytoplasmic domain. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR (see WO98/50433, Abgenix), Bevacizumab (Avastin), 2C3, HuMV833, cetuximab (Erbitux®), panitumumab (Vectibix®), nimotuzumab (TheraCim®), matuzumab, zalutuzumab, mAb 806, or IMC-11F8. Examples of inhibitors of the tyrosine kinase activity of EGFR include ZD1839 or Gefitinib (IRESSA™; Astra Zeneca), CP-358774 (TARCEVA™; Genentech/OSI) and AG1478, AG1571 (SU 5271; Sugen), erlotinib (Tarceva), sutent (sunitinib), lapatinib, imatinib, sorafenib (nexavar), vandetanib, axitinib, bosutinib, cedivanib, dasatinib (sprycel), lestaurtinib, pazopanib and/or ARQ1 97. In a preferred embodiment the EGFR-targeted drug is sorafenib. When the subject suffers from hepatocelular carcinoma the first line chemotherapeutic treatment is an EGFR-targeted drug, preferably sorafenib.

The term "HER2-targeted drug" refers to a drug directed against the protein human epidermal growth factor receptor 2 (HER2) which is overexpressed in a particular subtype of breast cancers (HER2+). HER2-targeted drugs include, without limitation, trastuzumab, lapatinib, pertuzumab, neratinib, trastuzumab-DM1 and mTOR inhibitors such as everolimus or temsirolimus. In a preferred embodiment the HER2-targeted drug is trastuzumab. When the subject suffers from breast cancer HER2+ for hormonal receptors, the first line treatment is an HER2-targeted drug, preferably trastuzumab.

The term "CD20-targeted drug" refers to a drug directed to the CD20 antigen on B lymphocytes. CD20-targeted drugs include, without limitation, anti-CD20 antibodies such as rituximab, ocrelizumab, PRO70769, rhuH27, ofatumumab, veltuzumab, hA20, IMMU-106, AME-133, LY2469298, PRO131921, GA-101, tositumomab and RO5072759. In a preferred embodiment the CD20-targeted drug is rituximab. When the subject suffers from a Hodgkin's lymphoma the first line treatment is selected from combined chemotherapy, rituximab and combinations thereof. "Combined chemotherapy" is meant a combination of anticancer drugs that work through different cytotoxic mechanisms. Combined chemotherapy for the treatment of Hodgkin's lymphoma is, without limitation, ABVD (adriamycin/bleomycin/vinblastine/dacarbazine), MOPP (mechlorethamine/vincristine/procarbazine/prednisone), BEACOPP (bleomycin/etoposide/adriamycin/cyclophosphamide/vincristine/procarbazine/prednisone), Stanford V (a mustard derivative such as cyclophosphamide, mechlorethamine or ifosfamide/doxorubicin/vinblastine/vincristine/bleomycin/etoposide/prednisone), ChlVPP/EVA (chlorambucil, vincristine, procarbazine, prednisone, etoposide, vinblastine, adriamycin) and VAPEC-B (vincristine/adriamycin/prednisone/etoposide/cyclophosphamide/bleomycin). When the subject suffers from non-Hodgkin's lymphoma the first line chemotherapeutic treatment are combined chemotherapy selected from, without limitation, CHOP (cyclophosphamide/doxorubicin/vincristine/prednisone), CHOP-R or R-CHOP (CHOP+rituximab), COP or CVP (cyclophosphamide/vincristine/prednisone), COPP (cyclophosphamide/vincristine/procarbazine/prednisone), m-BACOD (methotrexate/bleomycin/adriamycin/cyclophosphamide/vincristine/dexamethasone), MACOP-B (methotrexate/leucovorin/adriamycin/cyclophosphamide/vincristine/prednisone/bleomycin), ProMACE-MOPP (methotrexate/adriamycin/cyclophosphamide/etoposide+ MOPP), ProMACE-CytaBOM (prednisone/adriamycin/cyclophosphamide/etoposide/cytarabine/bleomycin/vincristine/methotrexate/leucovorin) and R-FCM (rituximab/fludarabine/cyclophosphamide/mitoxantrone).

In another embodiment, the method of the invention further comprises the determination in the CUP of the methylation status of CpG sites which are indicative of a chemosensity to different drugs. This would allow improving the therapeutic decision for the CUP. Suitable CpG sites which can be used according to the present invention include, without limitation, MGMT-temodal/dacarbazine (Esteller, New England Journal of Medicine 2000; Oaz et al., Clin Cancer Res 2004, etc), WRN-irinotecan/topotecan (Agrelo et al., Proc Natl Acad Sci USA 2006) and BRCA1-Oxaliplatin/Cisplatin/PARP Inhibitors (Veeck et al., Journal of Clinical Oncology 2010).

Methods for the Personalized Treatment of a Subject Suffering from CUP

The methods disclosed in the present invention are useful for determining the origin of a CUP. Since CUPs are therapeutically targeted using a therapy which is adequate for the primary tumor, the identification of the origin of the CUP will allow the treatment of a patient suffering a CUP with a therapy using a therapy which has been previously confirmed as being adequate for the primary tumor.

Thus, in another aspect, the invention relates to a method for treating a cancer of unknown primary origin (CUP) in a subject (hereinafter third method of the invention) comprising the steps of:
  (i) determining the methylation profile in a selected region of a DNA isolated from said CUP,
  (ii) comparing the methylation profile of said selected region with the methylation profile of the same region in a DNA sample isolated from at least one primary tumor and
  (iii) treating the subject with a therapy adequate for said primary tumor wherein the methylation profile obtained in (i) shows a substantial identity with the methylation profile of the primary tumor.

Steps (i) and (ii) are carried out essentially as described in the first and second methods of the invention.

In a preferred embodiment, the primary tumor is selected from the group consisting of a lymphoid neoplasia, head and neck cancer, pancreatic cancer, endometrial cancer, colon cancer, prostate cancer, glioma, ovarian cancer, lung cancer, bladder cancer, melanoma, breast cancer, a myeloid neoplasia, testicular cancer, stomach cancer.

In a preferred embodiment, the determination of the methylation profile according to the third method of the invention comprises the determination of the methylation status in one or more CpG sites as defined in Tables 1 to 15 wherein
  (i) the methylation status in one or more CpG sites as defined in Table 1A or in Table 1B is compared with the methylation status of a lymphoid neoplasia,
  (ii) the methylation status in one or more CpG sites as defined in Table 2A or 2B is compared with the methylation status of a head and neck cancer,
  (iii) the methylation status in one or more CpG sites as defined in Table 3A or 3B is compared with the methylation status of a pancreatic cancer,
  (iv) the methylation status in one or more CpG sites as defined in Table 4A or 4B is compared with the methylation status of a endometrial cancer,
  (v) the methylation status in one or more CpG sites as defined in Table 5A or 5B is compared with the methylation status of a colon cancer,
  (vi) the methylation status in one or more CpG sites as defined in Table 6A or 6B is compared with the methylation status of a prostate cancer,
  (vii) the methylation status in one or more CpG sites as defined in Table 7A or 7B is compared with the methylation status of a glioma,
  (viii) the methylation status in one or more CpG sites as defined in Table 8A or 8B is compared with the methylation status of an ovarian cancer,
  (ix) the methylation status in one or more CpG sites as defined in Table 9A or 9B is compared with the methylation status of a lung cancer,
  (x) the methylation status in one or more CpG sites as defined in Table 10A or 10B is compared with the methylation status of a bladder cancer,
  (xi) the methylation status in one or more CpG sites as defined in Table 11A or 11B is compared with the methylation status of a melanoma, (xii) the methylation status in one or more CpG sites as defined in Table 12A is compared with the methylation status of a breast cancer, (xiii) the methylation status in one or more CpG sites as defined in Table 13A or 13B is compared with the methylation status of a myeloid neoplasia, (xiv) the methylation status in one or more CpG sites as defined in Table 14A or 14B or is compared with the methylation status of a testicular cancer and/or (xv) the methylation status in one or more CpG sites as defined in Table 15A or 15B is compared with the methylation status of a stomach cancer.

The therapy to be administered to the patient suffering CUP can then be determined on the basis of the therapy which is commonly applied to the primary tumor (see suitable therapies on Table 16).

In another embodiment, the method of the invention further comprises the determination in the CUP of the methylation status of CpG sites which are indicative of a chemosensity to different drugs. This would allow improving the therapeutic decision for the CUP. Suitable CpG sites which can be used according to the present invention include, without limitation, MGMT-temodal/dacarbazine (Esteller, New England Journal of Medicine 2000; Oaz et al., Clin Cancer Res 2004, etc), WRN-irinotecan/topotecan (Agrelo et al., Proc Natl Acad Sci USA 2006) and BRCA1-Oxaliplatin/Cisplatin/PARP Inhibitors (Veeck et al., Journal of Clinical Oncology 2010).

Kits

In another aspect, the invention relates to a kit for use in any of the methods according to the invention, wherein the kit comprises a plurality of primers or probes specific for determining a methylation status of a CpG site expressed by a CUP.

For kits for detection of methylation, the kits can comprise at least one polynucleotide that hybridizes to at least one of the methylation biomarker sequences and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. The kits can provide solid supports in the form of an assay apparatus that is adapted to use in the assay. In a particular aspect, kits for the methods of certain aspects of the present invention can include, e.g., one or more of methylation-dependent restriction enzymes, methylation-sensitive restriction enzymes, amplification (e.g., PCR) reagents, probes and/or primers.

The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In a certain aspect, these kits may comprise a plurality of agents for assessing the methylation of a plurality of methylation biomarkers, for example, one, two, three, four, five, six, seven or more of the methylation biomarkers as described above, wherein the kit is housed in a container.

In another particular embodiment, the primers or probes specific for determining a methylation status of a CpG site expressed by a CUP represent at least 10%, 20%, 30%, 40%, 50%, 60%, 70%, 80%, 90%, 95% or 99% of the total amounts of reagents in the kit.

The kits may further comprise instructions for using the kit for assessing methylation, means for converting the methylation data into methylation values and/or means for analyzing the methylation data or values to generate prognosis. The agents in the kit for measuring biomarker methylation may comprise a plurality of probes and/or primers for methylation-sensitive extension or amplification of the biomarkers. In another embodiment, the agents in the kit for measuring biomarker methylation may comprise an array of polynucleotides complementary to the nucleic acid sequence of the biomarkers of the invention. Possible means for converting the methylation data into methylation values and for analyzing the methylation values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

Computer Systems and Programs

In another aspect, the invention relates to a computer system that is provided with means for implementing the first, second or third method according to the invention. The computer system can include:

(a) at least one memory containing at least one computer program adapted to control the operation of the computer system to implement a method that includes: (i) receiving DNA methylation data e.g., the methylation profile of a CUP and the methylation profile of one or more primary tumors, (ii) determining the degree of identity between the methylation profile of the CUP and the methylation profile of the primary tumors and (b) at least one processor for executing the computer program.

Another aspect of the present invention relates to a computer program for controlling a computer system to execute the steps according to the first, second or third method of the invention.

The computer system can include one or more general or special purpose processors and associated memory, including volatile and non-volatile memory devices. The computer system memory can store software or computer programs for controlling the operation of the computer system to make a special purpose system according to the invention or to implement a system to perform the methods according to the invention. The computer system can include an Intel or AMD x86 based single or multi-core central processing unit (CPU), an ARM processor or similar computer processor for processing the data. The CPU or microprocessor can be any conventional general purpose single- or multi-chip microprocessor such as an Intel Pentium processor, an Intel 8051 processor, a RISC or MISS processor, a Power PC processor, or an ALPHA processor. In addition, the microprocessor may be any conventional or special purpose microprocessor such as a digital signal processor or a graphics processor. The microprocessor typically has conventional address lines, conventional data lines, and one or more conventional control lines. As described below, the software according to the invention can be executed on dedicated system or on a general purpose computer having a DOS, CPM, Windows, Unix, Linix or other operating system. The system can include non-volatile memory, such as disk memory and solid state memory for storing computer programs, software and data and volatile memory, such as high speed ram for executing programs and software.

Computer-readable physical storage media useful in various embodiments of the invention can include any physical computer-readable storage medium, e.g., solid state memory (such as flash memory), magnetic and optical computer-readable storage media and devices, and memory that uses other persistent storage technologies. In some embodiments, a computer readable media can be any tangible media that allows computer programs and data to be accessed by a computer. Computer readable media can include volatile and nonvolatile, removable and non-removable tangible media implemented in any method or technology capable of storing information such as computer readable instructions, program modules, programs, data, data structures, and database information. In some embodiments of the invention, computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store information and which can read by a computer including and any suitable combination of the foregoing.

The present invention can be implemented on a stand-alone computer or as part of a networked computer system. In a stand-alone computer, all the software and data can reside on local memory devices, for example an optical disk or flash memory device can be used to store the computer software for implementing the invention as well as the data. In alternative embodiments, the software or the data or both can be accessed through a network connection to remote devices. In one networked computer system embodiment, the invention use a client-server environment over a public network, such as the internet or a private network to connect to data and resources stored in remote and/or centrally located locations. In this embodiment, a server including a web server can provide access, either open access, pay as you go or subscription based access to the information provided according to the invention. In a client server environment, a client computer executing a client software or program, such as a web browser, connects to the server over a network. The client software or web browser provides a user interface for a user of the invention to input data and information and receive access to data and information. The client software can be viewed on a local computer display or other output device and can allow the user to input information, such as by using a computer keyboard, mouse or other input device. The server executes one or more computer programs that enable the client software to input data, process data according to the invention and output data to the user, as well as provide access to local and remote computer resources. For example, the user interface can include a graphical user interface comprising an access element, such as a text box, that permits entry of data from the assay, e.g., the DNA methylation data levels or DNA gene expression levels of target genes of a reference pluripotent stem cell population and/or pluripotent stem cell population of interest, as well as a display element that can provide a graphical read out of the results of a comparison with a score card, or data sets transmitted to or made available by a processor following execution of the instructions encoded on a computer-readable medium.

In some embodiments of the present invention, the methylation profiles from primary tumors, which are used as references can be electronically or digitally recorded, annotated and retrieved from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that may be employed to determine homologies between the reference data or genes or proteins within and among genomes.

In some embodiments of this aspect and all other aspects of the present invention, the system can compare the data in a "comparison module" which can use a variety of available software programs and formats for the comparison operative to compare sequence information determined in the determination module to reference data. In one embodiment, the comparison module is configured to use pattern recognition techniques to compare sequence information from one or more entries to one or more reference data patterns. The comparison module may be configured using existing commercially-available or freely-available software for comparing patterns, and may be optimized for particular data comparisons that are conducted. The comparison module can also provide computer readable information related to the sequence information that can include, for example, detection of the presence or absence of a CpG methylation sites in DNA sequences; determination of the level of methylation.

In some embodiments, the comparison module provides computer readable comparison result that can be processed in computer readable form by predefined criteria, or criteria defined by a user, to provide a report which comprises content based in part on the comparison result that may be stored and output as requested by a user using a display module. In some embodiments, a display module enables display of a content based in part on the comparison result for the user, wherein the content is a report indicative of the results of the comparison of methylation profile of the CUP of interest with the methylation profile of a tumor cell.

In some embodiments, the display module enables display of a report or content based in part on the comparison result for the end user, wherein the content is a report indicative of the results of the comparison of the methylation profile of the CUP with the methylation profile of the selected primary tumors. In some embodiments of this aspect and all other aspects of the present invention, the comparison module, or any other module of the invention, can include an operating system (e.g., UNIX, Windows) on which runs a relational database management system, a World Wide Web application, and a World Wide Web server. World Wide Web application can includes the executable code necessary for generation of database language statements [e.g., Standard Query Language (SQL) statements]. The executables can include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using an HTML interface provided by Web browsers and Web servers. In other embodiments of the invention, other interfaces, such as HTTP, FTP, SSH and VPN based interfaces can be used to connect to the Internet databases.

The computer instructions can be implemented in software, firmware or hardware and include any type of programmed step undertaken by modules of the information processing system. The computer system can be connected to a local area network (LAN) or a wide area network (WAN). One example of the local area network can be a corporate computing network, including access to the Internet, to which computers and computing devices comprising the data processing system are connected. In one embodiment, the LAN uses the industry standard Transmission Control Protocol/Internet Protocol (TCP/IP) network protocols for communication. Transmission Control Protocol Transmission Control Protocol (TCP) can be used as a transport layer protocol to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data retransmissions, and multiplexing multiple connections through a single network connection. Finally, TCP is responsible for encapsulating information into a datagram structure. In alternative embodiments, the LAN can conform to other network standards, including, but not limited to, the International Standards Organization's Open Systems Interconnection, IBM's SNA, Novell's Netware, and Banyan VINES.

In some embodiments of this aspect and all other aspects of the present invention, a comparison module provides computer readable data that can be processed in computer readable form by predefined criteria, or criteria defined by a user, to provide a retrieved content that may be stored and output as requested by a user using a display module.

In accordance with some embodiments of the invention, the computerized system can include or be operatively connected to a display module, such as computer monitor, touch screen or video display system. The display module allows user instructions to be presented to the user of the system, to view inputs to the system and for the system to display the results to the user as part of a user interface. Optionally, the computerized system can include or be operative connected to a printing device for producing printed copies of information output by the system.

In some embodiments of the present invention, a World Wide Web browser can be used to provide a user interface to allow the user to interact with the system to input information, construct requests and to display retrieved content. In addition, the various functional modules of the system can be adapted to use a web browser to provide a user interface. Using a Web browser, a user can construct requests for retrieving data from data sources, such as data bases and interact with the comparison module to perform comparisons and pattern matching. The user can point to and click on user interface elements such as buttons, pull down menus, scroll bars, etc. conventionally employed in graphical user interfaces to interact with the system and cause the system to perform the methods of the invention. The requests formulated with the user's Web browser can be transmitted over a network to a Web application that can process or format the request to produce a query of one or more database that can be employed to provide the pertinent information related to the DNA methylation levels and gene expression levels, the retrieved content, process this information and output the results.

The invention is described by way of the following examples which are to be construed as merely illustrative and not limitative of the scope of the invention.

Example 1

DNA Methylation Fingerprint of Human Normal Tissues and Human Cancer

Materials & Methods

DNA Samples

DNA human samples were collected by from 1,819 samples. Replicates used for validation (n=84), samples that did not attain control quality cut-offs (n=87) and the in vitro methylated DNAs used as whole genome positive marker for CpG methylation (IVD; n=20) were excluded. Thus, finally 1,628 human samples were analyzed. A criterion to define the quality of a sample is explained below. A detailed list of all the samples included in the study is displayed in Table 17.

TABLE 17

Complete list of 1,628 human samples included in the study

| Normal Tissues (n: 424) | n | Tumorigenic Samples (n: 1054) | n | Non-cancerous diseases (n: 150) | n |
|---|---|---|---|---|---|
| Primary tissues (n: 390) | | Solid tumors (n: 611) | | Aorta (n: 18) | |
| | | Bladder | 44 | Atherosclerotic lesions | 18 |
| Aorta | 2 | Breast | 76 | Blood (n: 86) | |
| Apheresis | 4 | Cervix | 4 | Lupus | 7 |

TABLE 17-continued

Complete list of 1,628 human samples included in the study

| Normal Tissues (n: 424) | n | Tumorigenic Samples (n: 1054) | n | Non-cancerous diseases (n: 150) | n |
|---|---|---|---|---|---|
| Bladder | 8 | Colon | 110 | Autism | 30 |
| Blood | 180 | Endometrium | 68 | Alzheimer | 35 |
| Bone marrow | 14 | Esophagus | 13 | Primary biliary cirrhosis (PBC) | 4 |
| Brain | 6 | Ganglioneurom | 1 | | |
| Breast | 2 | Glioma | 90 | Systemic sclerosis (SSc) | 10 |
| Buccal epithelium | 21 | Head-neck | 9 | | |
| Cerebellum | 1 | Kidney | 5 | Brain (n: 26) | |
| Cervix | 1 | Liver | 19 | Alzheimer | 11 |
| Colon | 97 | Melanoma | 21 | Dementia (with Lewy bodies) | 13 |
| Endometrium | 2 | Neuroblastoma | 16 | | |
| Esophagus | 5 | Non-small Cell Lung Carcinoma | 23 | Parkinson | 1 |
| Fetal brain | 1 | | | Muscle (n: 17) | |
| Heart | 2 | Ovarian | 30 | Myopathies | 17 |
| Liver | 5 | Pancreas* | 29 | Immunodeficiency, Centromere instability and Facial anomalies syndrome (ICF syndrome) | 4 |
| Lung | 3 | Prostate | 14 | | |
| Muscle | 5 | Stomach | 16 | | |
| Ovary | 2 | Testis | 23 | | |
| Pancreas | 7 | Hematologic malignancies (n: 244) | | | |
| Prostate | 5 | | | | |
| Skin | 5 | Acute lymphoblastic leukemia (ALL) | 58 | | |
| Stomach | 7 | | | | |
| Suprarenal gland | 1 | Acute myeloblastic leukemia (AML) | 34 | | |
| Testis | 4 | | | | |
| Normal cell lines (n: 7) | | Chronic lymphocytic leukemia (CLL) | 25 | | |
| Lymphoblastoid | 6 | Diffuse large B-cell lymphoma (DLBCL) | 49 | | |
| Melanocyte | 1 | | | | |
| Stem Cells (n: 27) | | Follicular lymphoma (FL) | 14 | | |
| Adult | 19 | | | | |
| Embryonic | 8 | Mantle cell lymphoma (MCL) | 10 | | |
| | | Molecular Burkitt's lymphoma (mBL) | 18 | | |
| | | Multip myeloma (MM) | 14 | | |
| | | Myeloproliferative syndromes (MDS/MPS) | 13 | | |
| | | Mixed lineage leukemia | 9 | | |
| | | Metastases (n: 50) | | | |
| | | Colon to Liver | 32 | | |
| | | Colon to Brain | 13 | | |
| | | Kidney to Brain | 5 | | |
| | | Premalignant lesions (n: 25) | | | |
| | | Adenomas (colon) | 12 | | |
| | | Breast | 7 | | |
| | | Endometrium hyperplasia | 6 | | |
| | | Cancer cell lines (n: 82) | | | |
| | | Breast | 6 | | |
| | | Cervix | 4 | | |
| | | Colon | 10 | | |
| | | Esophagus | 2 | | |
| | | Head-neck | 2 | | |
| | | Leukemia | 3 | | |
| | | Liver | 3 | | |
| | | Lung | 10 | | |
| | | Lymphoma | 23 | | |
| | | Melanocyte | 2 | | |
| | | Neuroblastoma | 2 | | |
| | | Pancreas | 12 | | |
| | | Prostate | 3 | | |
| | | Carcinoma of unknow primary (CUP) | 42 | | |

All patients provided informed consent and the study was conducted under the approval of the corresponding Institutional Review Boards. For primary malignancies, fresh-frozen tissue samples were macrodissected to obtain a 90-95% purity of non-necrotic tumor and non-involved adjacent non-neoplastic tissue. In order to assess the quality of the dataset, the Pearson correlation coefficient of all pairs of methylation profiles was computed; almost all replicate pairs had values close to 1. For subsequent analyses, replicates were combined by averaging the CpG methylation profiles of all records for a sample.

DNA Methylation Analysis Using Universal BeadArrays

Microarray-based DNA methylation profiling was performed on all samples with the GoldenGate Methylation Cancer Panel I (Illumina, Inc.). The panel was developed to assay 1,505 CpG sites selected from 807 genes, which include oncogenes and tumor suppressor genes, previously reported differentially methylated or differentially expressed genes, imprinted genes, genes involved in various signaling pathways, and those responsible for DNA repair, cell cycle control, metastasis, differentiation and apoptosis. The DNA methylation analyses were performed in the Human Genotyping Unit—CEGEN of the Spanish National Cancer Research Centre (Madrid, Spain), except for 8% of cases (127 hematological malignancies) where the analysis was developed at the Illumina Headquarters (San Diego, Calif.). No significant inter-laboratory variation was observed.

DNA methylation assay was performed as previously described by Bibikova et al. in 2006 (Bibikova et al. 2006. High-throughput DNA methylation profiling using universal bead arrays. *Genome Res* 16(3): 383-393). Briefly, four probes were designed for each CpG site: two allele-specific oligos (ASOs) and two locus-specific oligos (LSOs). Each ASO-LSO oligo pair corresponded to either the methylated or unmethylated state of the CpG site. Bisulfite conversion of DNA samples was done using the EZ DNA methylation kit (Zymo Research, Orange, Calif.). After bisulfite treatment, the remaining assay steps were identical to the GoldenGate genotyping assay (Fan et al. 2003. Highly parallel SNP genotyping. *Cold Spring Harb Symp Quant Biol* 68: 69-78) using Illumina-supplied reagents and conditions. The array hybridization was conducted under a temperature gradient program, and arrays were imaged using a BeadArray Reader (Illumina Inc.). Image processing and intensity data extraction software were performed as described previously (Galinsky. 2003. Automatic registration of microarray images. I. Rectangular grid. *Bioinformatics* 19(14): 1824-1831; Galinsky. 2003. Automatic registration of microarray images. II. Hexagonal grid. *Bioinformatics* 19(14): 1832-1836). Each methylation data point is represented by fluorescent signals from the M (methylated) and U (unmethylated) alleles. Background intensity computed from a set of negative controls was subtracted from each analytical data point. The ratio of fluorescent signals was then computed from the two alleles according to the following formula:

$$\text{Beta} = \frac{\text{Max}(M, 0)}{\text{Max}(U, 0) + \text{Max}(M, 0) + 100}$$

Beta is a quantitative measure of DNA methylation levels of specific CpGs, and ranges from 0 for complete unmethylation to 1 for complete methylation. DNA methylation Beta values and p-values (measure of quality) for the 1,628 samples are available on the website: http://ubio.bioinfo.cnio.es/biotools/Human_DNA_Methylomes/ (user: data; password: 10HUMAN54). The sequence data from this study have been submitted to the NCBI Gene Expression Omnibus (http://www.ncbi.nlm.nih.gov/geo) under accession no. GSE28094.

Filtering of Probes and Samples

Although the GoldenGate Assay by Illumina is an established, highly reproducible method for DNA methylation detection, there is currently no standard procedure for post-filtering of probes and samples commonly used. Before analyzing the methylation data, several ways of excluding possible sources of biological and technical biases that could have affected and improved the accuracy of the results were explored. Every beta value in the GoldenGate platform is accompanied by a detection P-value. The criteria of filtering was based on these P-values reported by the assay. Two aspects of filtering out probes and samples based on the detection P-values were examined, selecting a threshold and a cutoff. The analyses indicated that a threshold value of 0.01 allows a clear distinction to be made between reliable and unreliable beta values. A cutoff value as 5% was selected. Following this criterion, all probes with detection P-values>0.01 in 5% or more of the samples were first removed. As a second step, all samples with detection P-values>0.01 in 5% or more of their (remaining) probes were removed. In total, 130 probes and 87 samples were removed. Consistently unmethylated and methylated probes were checked for and removed. All cell line samples were ignored and inventors focused on the remaining 1521 (primary tissue) samples. All probes exhibiting a degree of methylation <0.25 for all primary tissue samples were considered to be consistently unmethylated. Similarly, probes with a degree of methylation >0.75 for all primary tissue samples were considered to be consistently methylated. Nine consistently unmethylated probes were identified; none of the probes fit the inventor's definition for being consistently methylated. A known biological factor is that one copy of chromosome X is methylated in women, and, therefore, all probes with prominent gender-specific methylation were identified and removed in order to avoid hidden bias in the subsequent analyses. The set of 1271 samples with gender information was considered; approximately half of them were female. A probe was defined to be gender-specific if (1) the probe showed a significant differential methylation between the two sample groups, as determined by the Mann-Whitney U-test with FDR correction; and (2) the mean methylation degrees of females and males for this probe differed by at least 0.17 (a limitation of the GoldenGate assay). After excluding 130 probes that were not of sufficient quality, nine that were consistently unmethylated and 44 that were gender-specific, 1322 probes were available for further statistical analyses.

Analysis of Differentially Methylated Probes

The large cohort of heterogeneous methylation profiles allows inventor to identify differentially methylated probes under a variety of scenarios. Different groups of tissue samples were separately examined (normal primary tissues, cancerous diseases, and cancer cell lines). All statistical analyses were performed using the R environment for statistical computing (version 2.10; http://www.R-project.org). Further explanation about detection of differentially methylated probes and genes in each scenario, statistical analyses, and graphical representations are provided below.

Different methods of analysis were used depending on (1) the number of groups compared, and (2) when comparing two groups, the number of samples in the "case" and "control" groups.

Elastic net methods were used to compare several groups of samples. The probes were selected by elastic net classifiers, trained with 10-fold cross-validation using misclassification loss. This approach was designed for applications, in which the number of features (probes) greatly exceeds the number of analyzed samples. These methods have recently been introduced to the Bioinformatics community and have been applied in SNP and gene expression datasets.

The Kruskal-Wallis test with the Benjamini-Hochberg algorithm was used to calculate the false discovery rate when two groups with a large number of samples were compared. Note that all methods were applied after a pre-filtering step, as suggested by Martin-Subero et al. (Martin-Subero et al. 2009, *Blood* 113: 2488-2497) and only probes with mean methylation group differences of at least 0.25 were considered.

It was implemented a specific strategy for determining differentially methylated probes in cases where two sample groups (cases and controls) were compared, and the control group was relatively small. This strategy does not include a prefiltering step, and is based on a heuristic approach, described briefly below. With this algorithm, a very small number of control (healthy) samples are compared with a larger group of case (disease) samples. A probe P was defined as unmethylated in a set of control samples, when the mean methylation value for this probe was <0.25. Similarly, P was taken to be methylated if the average methylation value was >0.75. P was reported as hypermethylated in the case samples if and only if P was unmethylated in the control samples and the beta value of P was >0.75 in at least 10% of the case samples. Likewise, the set of hypomethylated probes are those probes P that were methylated in the control group and had methylation values <0.25 in at least 10% of the samples in case group. Another situation in which standard statistical methods are inapplicable is when the methylation profiles of two very small groups of samples (controls and cases) are compared. A heuristic approach very similar to the previous one was applied. A probe was first classified in the control group as unmethylated if the all methylation values for this probe among samples in the group were <0.5 and the mean values were <0.25. Alternatively, a probe was considered to be methylated in the control group if the observed values for all samples were >0.5 and the mean value was >0.75. The criteria for case group membership were stricter: unmethylated probes were those in which the observed methylation value in all samples was <0.25; the methylation values for all samples in a methylated probe were >0.75. The set of differentially methylated probes consists of all probes that were methylated in the control group but unmethylated in the case (hypomethylated probes), as well as all probes that were unmethylated in the controls but methylated in the cases (hypermethylated probes).

In all settings, in which the methylation profiles of two groups were compared, the differentially methylated probes were characterized as being hypomethylated or hypermethylated with respect to the control groups, using the Kruskal-Wallis test with the Benjamini-Hochberg algorithm or heuristic methods. Associations between differentially methylated probes and CGI or non CGI location were compared using Fisher's exact test. In addition to Fisher's exact test, permutation-based p-values were calculated to account for interdependencies between the methylation states of different CpGs. Briefly, Fisher's exact test was performed in $10^4$ random reassignments of the studied samples and calculated the proportion of resulting p-values that is lower than or equal to the originally obtained one.

For normal primary tissues the probes were classified as consistently unmethylated and consistently methylated. The consistently unmethylated group consisted of all probes that <0.25 methylation in at least 99% of the samples. All probes with >0.75 methylation in at least 99% of the samples formed the group of consistently methylated probes. The top-scoring genes with tissue-specific DNA methylation were defined as genes with methylation values >0.75 in each tissue type.

Hierarchical Cluster Analysis and Graphical Representations

Statistical analyses were done and graphs produced with R (version 2.1.0) and Excel (Microsoft). Hierarchical clustering and heatmaps often contained tissue-, or cancer-specific probes calculated by Kruskal-Wallis test and elastic nets with misclassification. The Manhattan distance was used as the appropriate metric. A methylated CpG was always represented in red and an unmethylated CpG in green. The track legend that accompanies the heatmaps represents the CpG location as inside or outside a CpG island (in red and blue, respectively).

The deviation plot depicts the variability of methylation values for set samples. Probes are ordered on the x-axis and are ranked with respect to their median methylation, as visualized by a curve. The yellow area enclosed within a grey border depicts the 5th and 95th percentile among the methylation values for each probe. Additional information about the probes is presented color-coded below the x-axis; CpG island- and non-CpG island-(CGI- and non-CGI-) associated probes are marked in red, and blue, respectively. The amount of variation in the methylation profiles can be quantified as the relative area of deviation (yellow bars) in a deviation plot, which is a number between 0 and 1. An area of zero indicates no variation, whereas the value of 1 depicts that all possible degrees of methylation are observed for every probe. The Wilcoxon test was used to calculate p-values for the association between methylation variability and CGI overlap. The variability of a probe was estimated as the difference between the 5th and 95th percentile of the methylation values of this probe. The differences between two deviation plots were measured, taking into account the median and variation in methylation. For this purpose, the number of samples used in both plots was firstly equalized, and then performed a paired Wilcoxon test using the values of the visualized sequences.

Pyrosequencing

Pyrosequencing assays were designed to analyze and validate the results obtained from the array under different scenarios. Sodium bisulfite modification of 0.5 mg of genomic DNA isolated from different tissues was carried out with the EZ DNA Methylation Kit (Zymo Research Corporation) following the manufacturer's protocol. Bisulfite-treated DNA was eluted in 15-mL volumes with 2 mL used for each PCR. The set of primers for PCR amplification and sequencing were designed with a specific program (PyroMark assay design version 2.0.01.15). Primer sequences were designed to hybridize with CpG-free sites to ensure methylation-independent amplification. PCR was performed with primers biotinylated to convert the PCR product to single-stranded DNA templates. The Vacuum Prep Tool (Biotage) was used to prepare single-stranded PCR products according to the manufacturer's instructions. Pyrosequencing reactions and quantification methylation were performed in a PyroMark Q24 System version 2.0.6 (QIAGEN). Graphs of methylation values show bars identifying CpG sites with values from 0% (white) to 100% (black).

Classification of CUPs

The advanced method L1-regularized logistic regression with misclassification was used to classify the 42 CUP samples in the data set into one of the known cancer types. By classifying a CUP, this classifier gives probabilities (values between 0 and 1) for every known cancer type. A CUP prediction heatmap was derived in R (version 2.1.0). The CUP samples were selected on the basis of having a >30% probability of being ascribed to a specific tumor type. The arrangement of the samples in the heatmap was established by (1) ordering the tumor types by the number of CUPs ascribed to each one; and (2) within each tumor type, ranking the CUPs from the highest to lowest probability of ascription.

Expression Data Analysis

CEL files containing normal tissue gene expression data were downloaded from the GEO database using the following data series:

TABLE 18

List of data series containing normal tissue gene expression data from the GEO database.

| Tissue | GEO ID |
|---|---|
| Aorta | GSE7307 |
| Blood | GSE7307 |
| Bone marrow | GSE3526, GSE7307 |
| Brain | GSE3526 |
| Breast (mammary) | GSE3526, GSE7307 |
| Oral mucosa | GSE3526 |
| Cerebellum | GSE3526 |
| Cervix | GSE3526 |
| Colon (cecum) | GSE3526, GSE7307 |
| Endometrium | GSE3526 |
| Esophagus | GSE3526 |
| Heart | GSE3526 |
| Liver | GSE3526 |
| Lung | GSE3526 |
| Muscle | GSE3526 |
| Ovary | GSE3526 |
| Prostate | GSE7307 |
| Skin | GSE7307 |
| Stomach | GSE3526, GSE7307 |
| Suprarenal gland | GSE7307 |
| Testis | GSE3526 |

Raw data were imported into Flexarray (version 1.4.1) and RMA normalized using Affymetrix Power Tools (32bit, version 1.12.0). Affymetrix annotation file HG-U133_Plus_2.na30.annot.csv was used to select Affymetrix probeset ID-s that corresponded to genes with tissue-specific methylation patterns. Ambiguous probesets associated with more than one gene were not included. If there were multiple probesets reporting on same gene, their intensity values were averaged to yield gene-wise expression data. Selected expression data were imported into Genesis (version 1.7.1), median-centered and gene-wise normalized. Unsupervised hierarchical clustering and heatmaps using the expression data for the 354 genes (including the 511 tissue specific CpG sites) was carried out on the basis of Manhattan distance calculation and average linkage clustering. Gene expression data downloaded from GEO database and the same data series were used to define a gene as housekeeping gene. Genes expressed in 90% of the normal tissues included in the panel were selected. The following procedure was used: absent-present calls were generated from 99 normal tissue samples using the "mas5calls" function in the R package "affy". 8,643 probesets were found to be present ("P") in ≥90% of the samples. For these probesets, the corresponding gene symbols were determined using the Affymetrix annotation file HG-U133 Plus2.na30.annot.csv, yielding a list of "≥90%_expressed_genes" (5,427 genes identified). "≥90%_expressed_genes" list "unmethylated_genes in normal tissues" and "other_genes" list was crossed.

A density plot of microarray-based gene expression data in colon cancer patients was also experimentally obtained. Expression data were obtained from 19 primary colorectal tumors for which inventor had obtained DNA methylation profiles. 5 µg of RNA were hybridized on the Affymetrix Human GeneChip U133 Plus 2.0 expression array (Affymetrix, Santa Clara, Calif.). Expression data were normalized and analyzed following the same procedures as described above.

Data Access

The microarray data from this study have been submitted to the NCBI Gene expression Omnibus (http://www.ncbi.nlm.nih.gov/geo) under accession number GSE28094.

Results

Description of 1628 Samples and Analysis of 1505 CpG Sites

The genomic DNA from 1628 human samples corresponding to 424 normal tissues (180 leukocytes, 97 colon mucosa; and 227 other normal samples), 1054 tumorigenic samples (premalignant lesions, primary tumors, and metastases), and 150 non-cancerous disorders was studied. Table 17 shows the complete list of samples studied. The age of donors ranged from 6 months to 102 years, with an average age of 57 years. Forty percent (n=648) were men, and 38% (n=623) were women, the gender of the remaining 22% (n=357) not being known. Eighty-seven percent (n=1421) of the samples were from European volunteers and patients, while 4% (n=59) and 2% (n=36) were from Asian and North American populations, respectively; the origin was not known for 7% (n=112) of cases. Finally, 93% (n=1512) of the samples were primary tissues obtained at the time of the clinically indicated procedures, while 7% (n=116) were obtained from established cell lines. For all these samples, the DNA methylation fingerprints, defined by the status of 1505 CpG sites located from −1500 bp to 4-500 bp around the transcription start sites (TSS) of 808 selected genes using the GoldenGate DNA methylation BeadArray Inc.) assay, were obtained. The panel of genes includes oncogenes and tumor-suppressor genes, imprinted genes, genes involved in various signaling pathways, and those responsible for DNA repair, cell cycle control; metastasis, differentiation, and apoptosis. Sixty-nine percent (n=1044) of the 1505 CpG sites studied are located within a canonical CpG island (Takai and Jones 2002, Proc Natl Acad Sci 99: 3740-3745); while 31% (n=461) are situated outside CpG islands. All human chromosomes, except the Y chromosome, are included among the CpG sites analyzed. CpG sites in "CpG island shores", regions of comparatively low CpG density within 2 kb of CpG islands, are not printed in the array used, and their biological relevance has already been extensively studied (Doi et al. 2009, Nat. Genet., 41: 1350-1353; Irizarry et al. 2009, Nat Genet 41: 178-186). Briefly, in this case, four probes were designed for each CpG site: two allele-specific oligos (ASOs) and two locus-specific oligos (LSOs). Each ASO-LSO oligo pair corresponded to either the methylated or unmethylated state of the CpG site. After bisulfite treatment conversion, the remaining assay steps were identical to those of the GoldenGate genotyping assay using Illumina-supplied reagents and conditions, and the arrays were imaged using a BeadArray Reader (Illumina, Inc.). Each methylation data point was represented by fluorescent signals from the M (methylated) and U (unmethylated) alleles. Before analyzing the CpG methylation data, possible sources of technical biases that could have influenced the results were excluded. Every beta value in the GoldenGate platform is accompanied by a detection P-value, and it was observed that a threshold P-value above 0.01 indicated unreliable beta values (130 CpGs). X-chromosome CpG sites with female-specific DNA methylation (Reik and Lewis 2005, Nat. Rev. Genet 6: 403-410) were also excluded (44 CpGs). Finally, nine CpG sites that were unmethylated in all normal and disease-associated samples were also excluded. Using these filters, 1322 CpGs proved to be reliable and were used subsequently in the study. The precise DNA methylation status of every CpG dinucleotide analyzed in each of the 1628 samples studied is freely available by downloading from the NCBI Gene Expression Omnibus (www.ncbi.nlm.nih.gov) under accession number GSE28094, DNA Methylation Fingerprint of Human Normal Tissues Firstly, the DNA methylation fingerprints for 424 human normal tissues were analyzed. Of the 424 normal tissues studied, only 1% (n=17) of CpGs (corresponding to 14 genes) were methylated in all the samples studied. These exclusively methylated CpG dinucleotides were preferentially located outside CpG islands (82%; Fisher's exact test, $p=1.97\times10^{-5}$). Conversely, 37% (n=488) of the CpGs, corresponding to 359 5' ends of genes, were exclusively unmethylated in every normal tissue studied. These always unmethylated CpG dinucleotides were almost exclusively located within CpG islands (98%; Fisher's exact test, $p=2.20\times10\text{-}85$) and were associated with housekeeping expression genes (Fisher's exact test, $p=1.13\times10^{-4}$). Most importantly, significant differential DNA methylation (Kruskal-Wallis rank-sum test, $p<2.21\times10^{-16}$) was encountered between different normal samples of 511 CpG dinucleotides using elastic net classifiers, which enabled their distinction on the basis of tissue type using an unsupervised hierarchical clustering approach. The 511 CpG sites described correspond to 359 genes and, providing further validation to the data, 220 genes (61%; 220) and 137 (38%) were previously identified as genes with tissue-specific DNA methylation using the same 1505 CpG platform (Byun et al. 2009, Hum Mol Genet 18: 4808-4817) or a 27,000-CpG microarray (Nagae et al. 2011, Hum Mol Genet doi: 10.1093/hmg/ddr170), respectively. Illustrative examples of genes found in the three sets, and also confirmed by bisulfite genomic sequencing in another independent study (Eckhardt et al. 2006, Nat Genet 38: 1378-1385), include TBX1 (T-box 1), OSM (oncostatin M), and GP1BB (glycoprotein Ib (platelet) beta polypeptide).

For the 359 genes with tissue-type-specific CpG methylation, their expression patterns in the 21 normal tissues are known (GEO Expression Omnibus, GEO; http://www.ncbi.nih.gov/geo/). Unsupervised clustering analysis of the expression of these 359 genes discriminates each normal tissue type, as the CpG methylation did, reinforcing the association between DNA methylation and transcriptional silencing of the neighboring gene for these targets. Strikingly, the CpG sites for which methylation status was the most valuable for discriminating between tissue types were those located in non-CpG-island 5' ends (Fisher's exact test, $p=5.85\times10^{-49}$). These data support the long-standing hypothesis that most housekeeping genes contain CpG islands around their transcription start sites, while half of the tissue-specific genes have a CpG island at their 5' ends, and the other half are 5'-CpG-poor. The tissue-type-specific DNA methylation patterns, which are in line with previous observations in humans also match the developmental layers in which the tissues originated (endoderm, mesoderm, or ectoderm), implying the existence of germ-layer-specific DNA methylation (Sakamoto et al. 2007, Genes Cells 12: 1123-1132).

DNA Methylation Fingerprint of Human Cancer

The DNA methylation fingerprints for 1054 human tumorigenesis samples were also studied including 855 primary malignancies (611 solid tumors from 19 tissue types and 244 hematological malignancies), 50 metastatic lesions, 25 premalignant lesions, 82 cancer cell lines, and 42 cancers of unknown primary origin (CUPs) (Table 17). The DNA methylation map that emerges shows a tumor-type-specific profile characterized by the progressive gain of CpG methylation within CpG-island-associated promoters and a cumulative loss of CpG methylation outside CpG islands in the different steps of tumorigensis.

First, unsupervised clustering of the DNA methylation profiles obtained from the 855 primary tumors demonstrated that each type of malignancy had its own aberrant DNA methylation landscape. From a quantitative standpoint, 1003 CpG sites (76% of the 1322 validated CpGs) had significantly different methylation levels between tumor types (Kruskal-Wallis rank-sum test, $p<2.2\times10^{-16}$). The distinction of primary tumors by their tissue of origin was maintained even when the tissue-type-specific DNA methylation described above (511 CpG sites) from the analysis of the DNA methylation profiles for each normal tissue was substracted. Comparing each tumor type with its corresponding normal tissue, 729 CpG sites (55% of the 1322 CpGs) showed differential DNA methylation. Using these tumor/normal differentially methylated CpG sites, overall human primary tumors were characterized by increased levels of CpG dinucleotide methylation: 68% (n=496) were hypermethylated and 32% (n=233) were hypomethylated (t-test, $p=3.521\times10^{-5}$). Most importantly, the location of these DNA methylation events differed: CpG dinucleotide hypermethylation occurred within CpG islands (78%), while CpG hypomethylation was present in 5' ends of non-CpG-island genes (78%; Fisher's exact test, $p=2.59\times10^{-47}$; permutation P-value<0.001). A DNA methylation deviation plot for the 1322 CpG sites studied in all normal primary tissues (n=390) versus all primary tumors (n=855) shows the hypermethylated CpG sites within CpG islands and hypomethylated CpG sites outside CpG islands observed in the malignancies (paired Wilcoxon test, $p<2.2\times10^{-16}$). CpG sites with cancer-specific differential methylation according to tumor type in comparison with their corresponding normal tissue are provided in Tables 1A, 2A, 3A, 4A, 5A, 6A, 7A, 8A, 9A, 10A, 11A, 12A, 13A, 14A and 15A. Those CpG sites with highly specific methylation changes occurring only in one tumor type are shown in Tables 1B, 2B, 3B, 4B, 5B, 6B, 7B, 8B, 9B, 10B, 11B, 12B, 13B, 14B and 15B.

For the largest set of samples with paired normal-tumor tissues from the same patient (41 cases of colorectal cancer), it was observed that of the 1322 CpG sites studied, CpG dinucleotides within CpG-island promoters became significantly more DNA methylated in 79% of cases (34 of 43 normal/tumor pairs; Wilcoxon test, $p=2.47\times10^{-7}$), while CpGs located in non-CpG-island promoters more commonly underwent DNA hypomethylation events, in 51% of cases (22 of 43 normal/tumor pairs; Wilcoxon test, $p=0.001$). Considering the colorectal tumor population as a whole, in 68% of cases (28 of 41) the primary malignancy gained CpG dinucleotide methylation within promoter CpG islands and non-CpG-island promoters, while in 15% of tumors (6 of 41)

the gain of CpG island methylation occurred in a context of loss of promoter non-CpG-island methylation. Interestingly, 17% of cases (seven of 41) featured a loss of methylation in both promoter CpG islands and non-CpG-island promoters (FIG. 3A). Thus, the presence of hypermethylation of promoter CpG islands appears to be a common hallmark of human tumors, but there are subsets of cancers that present other DNA methylation profiles at promoter CpG sites that suggest additional and complex aberrant DNA methylation pathways in tumorigenesis. For example, the possibility that DNA hypomethylation events at CpGs located in non-CpG-island promoters, typical of genes with restricted tissue-specific expression (Illingworth and Bird 2009), can cause a loss of cellular identity in transformed cells is worth further investigation.

The DNA methylation fingerprints of human cancer obtained in this study can also provide additional important molecular diagnostic and prognostic biomarkers for the management of neoplasias. One example assessed is the case of the clinical entities classified as cancers of unknown primary origin (CUPs). These are patients who present metastatic diseases for which the primary site cannot be found despite standard investigation. The median survival in randomized studies of these patients is extremely poor (Abbruzzese et al. 1995, J Clin Oncol 13: 2094-2103); however if it were possible to predict the primary tumor site, the patient could be treated with a site-specific program, potentially resulting in better survival than that provided by non-specific treatment, for which the current median is only 7 months (Greco and Pavlidis 2009, Semin Oncol 36: 65-74). Deaths due to CUP were estimated to be 45,230 in 2007 in the United States (American Cancer Society 2007). CUPs have an incidence of 6% among all malignancies, and in 25% of cases, the primary site cannot be identified even upon postmortem examination (American Cancer Society 2007). The inability to identify the primary site of the cancer and the impossibility to provide the right treatment has a large impact on the expected clinical outcome of these patients.

Thus, the DNA methylation fingerprints of 42 CUPs that have been analyzed and compared the DNA methylation landscapes obtained with those from the aforementioned human malignancy collection where the original tissue type was known. It was not possible to assign a given tumor type for these CUPs in 69% (29 of 42) of cases using L1-regularized logistic regression with misclassification (R, version 2.10) to create a prediction heatmap (FIG. 2). A proposed foster primary in these 29 cases was also achieved by conventional clustering analysis. Most importantly, the tumor type prediction of the CUPs based on the DNA methylation analyses was fully confirmed in 78% of cases (7 of 9) for which detailed pathological analysis developed at a later stage in a blind fashion was able to provide a diagnosis. It might also be concluded that the remaining 31% (13 of 42) of the studied CUP cases did not represent any of the 19 tumor types included in this analysis (Table 17). The three most common tumor types present in the DNA methylation-assigned CUPs were colorectal cancer (34%, 10 of 29), non-small-cell lung cancer (17%, 5 of 29), and breast tumors (17%, 5 of 29). These cases are particularly interesting because the introduction of targeted therapies, such as treatment with epidermal growth factor receptor (EGFR) antibodies in colorectal cancer, small-molecule inhibitors for EGFR mutations in lung adenocarcinoma, and more personalized chemotherapy options for breast cancer as a function of the hormonal and ERBB2 receptor status have improved the outcome of said patients. Thus, it is tempting to propose that the prediction of a foster primary site for CUPs based on the DNA methylation profiles might identify a more specific treatment regimen for said patients that would improve their quality of life and survival.

The invention claimed is:

1. A method for diagnosing and treating a primary tumor in a subject suffering from a cancer of unknown primary origin (CUP), the method in a subject comprising:
   (i) obtaining a biological sample from the CUP,
   (ii) isolating DNA from the biological sample,
   (iii) determining a methylation profile of a selected region of the DNA isolated from the CUP, wherein determining the methylation profile comprises detecting methylation statuses of at least 9 CpG sites within the DNA isolated from the CUP by contacting the DNA with a plurality of probes specific for each CpG site and a reagent for detecting methylation,
   (iv) comparing the methylation profile of the selected region of the DNA isolated from the CUP with a methylation profile of the same selected region in a DNA sample isolated from a primary tumor,
   (v) diagnosing the subject as having the primary tumor when the methylation profile of the selected region of the DNA isolated from the CUP is identified as having the same methylation profile as the same region in the DNA sample isolated from the primary tumor, and
   (vi) treating the subject with a therapy targeted to the primary tumor according to the following Table:

| Type of Cancer | Therapy |
| --- | --- |
| Lung Cancer | Platinum-based compounds |
| Colon Cancer | Antimetabolites |
| Melanoma | Cytokines |
| Pancreatic Cancer | Antimetabolites |
| Prostate Cancer | Hormonal therapy and/or mitotic inhibitors for resistant patients |
| Glioma | DNA-alkylating drugs |
| Bladder Cancer | Antimetabolites and/or platinum-based compounds |
| Ovarian epithelial Cancer | Platinum-based compounds |
| Hepatobiliary Cancer | Antimetabolites and/or EGFR-targeted drugs |
| Breast Cancer | Hormonal therapy; hormonal therapy combined with cytostatic drugs selected from the group consisting of anthracycline, DNA-alkylating drug, and antimetabolite, and combinations thereof; and/or HER2-targeted drugs |
| Lymphoma | CD20-targeted drugs |
| Head and Neck Cancer | Mitotic inhibitors; and/or mitotic inhibitors in combination with platinum-based compounds and/or antimetabolites |
| Endometrial Cancer | Hormonal therapy |
| Myeloma | Corticosteroids; proteasome inhibitors; thalidomide; and/or lenalidomide |
| Testicular Cancer | Topoisomerase inhibitors in combination with platinum-based compounds |
| Stomach Cancer | DNA intercalating agents and/or DNA cross-linking agents. |

2. The method according to claim 1 wherein the primary tumor is selected from the group consisting of a lymphoid neoplasia, head and neck cancer, pancreatic cancer, endometrial cancer, colon cancer, prostate cancer, glioma, ovarian cancer, lung cancer, bladder cancer, melanoma, breast cancer, a myeloid neoplasia, testicular cancer, and stomach cancer.

3. The method according to claim 2 wherein detecting the methylation status comprises detecting the methylation status in one or more CpG sites as defined in Tables 1A and 1B, wherein the methylation status in one or more CpG sites as defined in Table 1A

| Lymphoid neoplasias hypermetylation (n:200) | CGI | Lymphoid neoplasias hypomethylation (n:54) | CGI |
|---|---|---|---|
| DBC1_P351_R | Y | DDR1_P332_R | N |
| NEFL_P209_R | Y | BLK_P14_F | N |
| HTR1B_P222_F | Y | LTA_P214_R | N |
| HS3ST2_E145_R | Y | NOTCH4_P938_F | N |
| IGSF4_P86_R | Y | RUNX3_P393_R | Y |
| DLK1_E227_R | Y | BLK_P668_R | N |
| SLC22A3_E122_R | Y | PADI4_P1011_R | N |
| ISL1_P379_F | Y | RUNX3_P247_F | Y |
| MYOD1_E156_F | Y | PLA2G2A_P528_F | N |
| DBC1_E204_F | Y | HLA-DOB_E432_R | N |
| IGFBP3_P423_R | Y | LCK_E28_F | Y |
| SOX1_P294_F | Y | DES_P1006_R | N |
| FAT_P279_R | Y | PMP22_P975_F | N |
| MOS_E60_R | Y | TMPRSS4_P552_F | N |
| SLIT2_P208_F | Y | RHOH_P953_R | N |
| HS3ST2_P171_F | Y | IL18BP_E285_F | N |
| PALM2-AKAP2_P420_R | Y | KLK11_P103_R | N |
| CFTR_P372_R | Y | RUNX3_E27_R | N |
| HTR1B_E232_R | Y | BGN_P333_R | N |
| RAB32_P493_R | Y | AOC3_P890_R | N |
| DIO3_P674_ | Y | LEFTY2_P561_F | N |
| NGFB_E353_F | Y | CCL3_E53_R | N |
| CHGA_E52_ | Y | IL12B_P1453_F | Y |
| IGF2_E134_ | Y | NOS2A_P288_R | N |
| SFRP1_P157_F | Y | NAT2_P11_F | N |
| SFRP1_E398_R | Y | E2F5_P516_R | Y |
| FGFR2_P460_R | Y | MPL_P657_F | N |
| PTGS2_P308_F | Y | PTHR1_P258_F | N |
| SEMA3C_E49_R | Y | PRSS1_E45_R | N |
| EYA4_P794_F | Y | PLA2G2A_E268_F | N |
| GATA6_P726_F | Y | CPA4_E20_F | N |
| CDH13_P88_F | Y | PI3_P1394_R | N |
| CDH13_E102_F | Y | TRIM29_P135_F | N |
| TFAP2C_E260_F | Y | EPHX1_E152_F | N |
| TUSC3_E29_R | Y | EPHX1_P1358_R | N |
| PITX2_E24_R | Y | DLC1_P695_F | N |
| MLF1_E243_F | Y | DSG1_P159_R | N |
| PLS3_E70_F | Y | SFTPB_P689_R | N |
| WNT2_P217_F | Y | IGF1_P933_F | N |
| FRZB_E186_R | Y | CLDN4_P1120_R | N |
| EYA4_E277_F | Y | IGF1_E394_F | N |
| HOXA9_E252_R | Y | HLA-DPB1_P540_F | N |
| ISL1_E87_R | Y | CSF1R_P73_F | N |
| HOXA9_P1141_R | Y | AIM2_E208_F | N |
| FZD9_E458_F | Y | IL1B_P829_F | N |
| ONECUT2_E96_F | Y | GRB7_P160_R | N |
| SOX17_P287_R | Y | MAGEC3_E307_F | N |
| ASCL2_P360_F | Y | AATK_E63_R | N |
| FAT_P973_R | Y | MMP9_E88_R | N |
| KDR_E79_F | Y | KRT13_P676_F | N |
| CDH11_P354_R | Y | IAPP_E280_F | N |
| GABRB3_E42_F | Y | SMARCB1_P220_R | Y |
| HOXA11_P698_F | Y | IFNG_P188_F | N |
| DCC_P471_R | Y | KRT1_P798_R | N |
| DSC2_E90_F | Y | | |
| IMPACT_P234_R | Y | | |
| GALR1_E52_F | Y | | |
| ADAMTS12_E52_R | Y | | |
| TJP1_P390_F | Y | | |
| IGFBP3_E65_R | Y | | |
| SLC5A8_E60_R | Y | | |
| TIMP3_seq_7_538_F | Y | | |
| PENK_P447_R | Y | | |
| KDR_P445_R | Y | | |
| ISL1_P554_F | Y | | |
| ADCYAP1_P398_F | Y | | |
| CDH11_P203_R | Y | | |
| CDH1_P52_R | Y | | |
| ETV1_P515_F | Y | | |
| EGFR_E295_R | Y | | |
| NTRK2_P10_F | Y | | |
| CTSL_P81_F | Y | | |
| SOX1_P1018_R | Y | | |
| SCGB3A1_E55_R | Y | | |
| RBP1_E158_F | Y | | |
| CALCA_E174_R | Y | | |
| HOXI313_P17_R | Y | | |
| ALOX12_E85_R | Y | | |
| FGFR2_P266_R | Y | | |
| DAPK1_P10_F | Y | | |
| RET_seq_54_5260_F | Y | | |
| NGFB_P13_F | Y | | |
| TJP1_P326_R | Y | | |
| PENK_E26_F | Y | | |
| ERBB4_P541_F | Y | | |
| TAL1_P594_F | Y | | |
| NTRK2_P395_R | Y | | |
| IPF1_P234_F | Y | | |
| FGF3_P171_R | Y | | |
| IHH_E186_F | Y | | |
| ASCL1_P747_F | Y | | |
| DES_E228_R | Y | | |
| DCC_P177_F | Y | | |
| SLIT2_E111_R | Y | | |
| SOX2_P546_F | Y | | |
| TPEF_seq_44_588_R | Y | | |
| ASCL2_P609_R | Y | | |
| SOX17_P303_F | Y | | |
| TNK1_P41_R | Y | | |
| DCC_E53_R | Y | | |
| NRG1_E74_F | Y | | |
| AGTR1_P41_F | Y | | |
| MAF_P826_R | Y | | |
| IHH_P246_R | Y | | |
| TMEFF2_P152_R | Y | | |
| PRKCDBP_E206_F | Y | | |
| IGFBP2_P306_F | Y | | |
| COL18A1_P365_R | Y | | |
| TFAP2C_P765_F | Y | | |
| RAB32_E314_R | Y | | |
| CCKBR_P480_F | Y | | |
| SLC5A8_P38_R | Y | | |
| FOSL2_E384_F | Y | | |
| EGFR_P260_R | Y | | |
| EPHA7_E6_F | Y | | |
| DAPK1_E46_R | Y | | |
| PTGS2_P524_R | Y | | |
| WT1_P853_F | Y | | |
| PDGFRA_E125_F | N | | |
| NTSR1_P318_F | Y | | |
| IGSF4_P454_F | Y | | |
| CYP1B1_E83_R | Y | | |
| RBP1_P426_R | Y | | |
| PLXDC2_E337_F | Y | | |
| WT1_E32_F | Y | | |
| PALM2-AKAP2_P183_R | Y | | |
| F2R_P839_F | Y | | |
| RASGRF1_E16_F | Y | | |
| NOTCH3_P198_R | Y | | |
| CEBPA_P706_F | Y | | |
| EVI1_E47_R | Y | | |
| HS3ST2_P546_F | Y | | |
| LOX_P313_R | Y | | |
| DAPK1_P345_R | Y | | |
| CDH11_E102_R | Y | | |
| ERG_E28_F | Y | | |
| GRB1O_E85_R | Y | | |
| GATA6_P21_R | Y | | |
| CCNA1_E7_F | Y | | |
| EPHA5_P66_F | Y | | |
| HOXI313_E21_F | Y | | |
| NPY_E31_R | Y | | |
| EPHB1_E202_R | Y | | |
| IGFBP7_P297_F | Y | | |
| COL18A1_P494_R | Y | | |
| NOTCH3_E403_F | Y | | |
| TUSC3_P85_R | Y | | |
| MT1A_P49_R | Y | | |
| BMP2_E48_R | Y | | |

-continued

| Lymphoid neoplasias hypermetylation (n:200) | CGI | Lymphoid neoplasias hypomethylation (n:54) | CGI |
|---|---|---|---|
| IGFBP1_E48_R | Y | | |
| ERBB4_P255_F | Y | | |
| IGFBP2_P353_R | Y | | |
| CALCA_P75_F | Y | | |
| ADCYAP1_P455_R | Y | | |
| PAX6_P50_R | Y | | |
| IGF2AS_E4_F | Y | | |
| GABRB3_P92_F | Y | | |
| RIPK4_P172_F | Y | | |
| TWIST1_E117_R | Y | | |
| ALK_E183_R | Y | | |
| EPHA3_P106_R | Y | | |
| TBX1_P885_R | Y | | |
| PAX6_E129_F | Y | | |
| RET_seq_53_5374_F | Y | | |
| TWIST1_P355_R | Y | | |
| GRB1O_P260_F | Y | | |
| BDNF_E19_R | Y | | |
| CDH1_P45_F | Y | | |
| EPHA5_E158_R | Y | | |
| TRIP6_P1090_F | Y | | |
| DIO3_P90_F | Y | | |
| OPCML_E219_R | Y | | |
| FGF5_P238_R | Y | | |
| HRASLS_E72_R | Y | | |
| ASCL1_E24_F | Y | | |
| EPHA7_P205_R | Y | | |
| HOXA11_E35_F | Y | | |
| HLF_E192_F | Y | | |
| IRAK3_P185_F | Y | | |
| INHA_P1189_F | Y | | |
| PYCARD_P150_F | Y | | |
| MT1A_P600_F | Y | | |
| LOX_P71_F | Y | | |
| PDGFRA_P1429_F | Y | | |
| FLT4_P180_R | Y | | |
| GAS7_E148_F | Y | | |
| DST_E31_F | Y | | |
| TEK_E75_F | N | | |
| THBS1_E207_R | Y | | |
| ROR2_E112_F | Y | | |
| IGFBP1_P12_R | Y | | |
| HIC2_P498_F | Y | | |
| MMP2_E21_R | Y | | |
| IHH_P529_F | Y | | |
| INHA_P1144_R | Y | | |
| PROK2_P390_F | Y | | |
| NRG1_P558_R | Y | | |
| TGFBI_P173_F | Y | | |
| FZD9_P175_F | Y | | |
| MEST_P62_R | Y | | | or in Table 1B

| Lymphoid neoplasias (hypermethylation) (n:69) | CGI | Lymphoid neoplasias (hypomethylation) (n:27) | CGI |
|---|---|---|---|
| IGSF4_P86_R | Y | DDR1_P332_R | N |
| FAT_P279_R | Y | LTA_P214_R | N |
| RAB32_P493_R | Y | NOTCH4_P938_F | N |
| IGF2_E134_R | Y | BLK_P668_R | N |
| FGFR2_P460_R | Y | PLA2G2A_P528_F | N |
| PTGS2_P308_F | Y | LCK_E28_F | Y |
| SEMA3C_E49_R | Y | DES_P1006_R | N |
| TFAP2C_E260_F | Y | PMP22_P975_F | N |
| ONECUT2_E96_F | Y | RHOH_P953_R | N |
| FAT_P973_R | Y | IL18BP_E285_F | N |
| IMPACT_P234_R | Y | BGN_P333_R | N |
| TJP1_P390_F | Y | NAT2_P11_F | N |
| IGFBP3_E65_R | Y | E2F5_P516_R | Y |
| CDH11_P203_R | Y | MPL_P657_F | N |
| CDH1_P52_R | Y | PLA2G2A_E268_F | N |
| ETV1_P515_F | Y | EPHX1_E152_F | N |
| EGFR_E295_R | Y | EPHX1_P1358_R | N |

-continued

| Lymphoid neoplasias (hypermethylation) (n:69) | CGI | Lymphoid neoplasias (hypomethylation) (n:27) | CGI |
|---|---|---|---|
| NTRK2_P10_F | Y | SFTPB_P689_R | N |
| CTSL_P81_F | Y | IGF1_P933_F | N |
| RBP1_E158_F | Y | IGF1_E394_F | N |
| FGFR2_P266_R | Y | HLA-DPB1_P540_F | N |
| DAPK1_P10_F | Y | CSF1R_P73_F | N |
| RET_seq_54_5260_F | Y | I_L1B_P829_F | N |
| TJP1_P326_R | Y | GRB7_P160_R | N |
| ERBB4_P541_F | Y | MMP9_E88_R | N |
| NTRK2_P395_R | Y | KRT13_P676_F | N |
| SOX2_P546_F | Y | SMARCB1_P220_R | Y |
| TNK1_P41_R | Y | | |
| MAF_P826_R | Y | | |
| IHH_P246_R | Y | | |
| IGFBP2_P306_F | Y | | |
| COL18A1_P365_R | Y | | |
| RAB32_E314_R | Y | | |
| CCKBR_P480_F | Y | | |
| EGFR_P260_R | Y | | |
| EPHA7_E6_F | Y | | |
| DAPK1_E46_R | Y | | |
| PDGFRA_E125_F | N | | |
| IGSF4_P454_F | Y | | |
| PD(DC2_E337_F | Y | | |
| PALM2-AKAP2_P183_R | Y | | |
| F2R_P839_F | Y | | |
| CEBPA_P706_F | Y | | |
| EVI1_E47_R | Y | | |
| LOX_P313_R | Y | | |
| DAPK1_P345_R | Y | | |
| GRB1O_E85_R | Y | | |
| HOXI313_E21_F | Y | | |
| NOTCH3_E403_F | Y | | |
| MT1A_P49_R | Y | | |
| BMP2_E48_R | Y | | |
| IGFBP1_E48_R | Y | | |
| ERBB4_P255_F | Y | | |
| IGFBP2_P353_R | Y | | |
| PAX6_P50_R | Y | | |
| RIPK4_P172_F | Y | | |
| PAX6_E129_F | Y | | |
| GRBIO_P260_F | Y | | |
| CDH1_P45_F | Y | | |
| HRASLS_E72_R | Y | | |
| EPHA7_P205_R | Y | | |
| HLF_E192_F | Y | | |
| INHA_P1189_F | Y | | |
| LOX_P71_F | Y | | |
| PDGFRA_P1429_F | Y | | |
| DST_E31_F | Y | | |
| THBS1_E207_R | Y | | |
| IHH_P529_F | Y | | |
| INHA_P1144_R | Y | | | is compared with the methylation status of a lymphoid neoplasia, wherein CGI is CpG island associated, Y is yes, and N is not.

4. The method of claim 1, wherein the methylation profile is determined by a method selected from the group consisting of: Methylation-Specific PCR (MSP); an enrichment-based method selected from the group consisting of MeDIP, MBD-seq, and MethylCap; a bisulfite-based method selected from the group consisting of RRBS, bisulfite sequencing, Infinium, GoldenGate, COBRA, MSP, and MethyLight; a MRE-seq restriction-digestion method; differential-conversion; and differential restriction.

5. The method according to claim 2, wherein detecting the methylation status comprises detecting the methylation status in one or more CpG sites as defined in Tables 2A and 2B, wherein the methylation status in one or more CpG sites as defined in Table 2A

| Head and neck cancer (hypermethylation) (n:171) | CGI | Head and neck cancer (hypomethylation) (n:20) | CGI |
|---|---|---|---|
| LCN2_P141_R | N | MMP2_P303_R | Y |
| PI3_P274_R | N | ERN1_P809_R | Y |
| KRT13_P341_R | N | MT1A_P600_F | Y |
| SLC22A18_P216_R | N | DLC1_E276_F | N |
| TMPRSS4_E83_F | N | RAB32_P493_R | Y |
| LCN2_P86_R | N | ICAM1_P386_R | Y |
| VAMP8_P241_F | N | JAK3_P156_R | N |
| KRT5_E196_R | Y | RUNX3_P247_F | Y |
| TRIP6_P1274_R | Y | TNFSF8_E258_R | N |
| TRIM29_P261_F | N | HLA-DPA1_P28_R | N |
| DSG1_P159_R | N | RUNX3_P393_R | Y |
| PENK_E26_F | Y | OSM_P188_F | Y |
| LY6G6E_P45_R | N | MPO_P883_R | N |
| TRIP6_P1090_F | Y | DLC1_P695_F | N |
| PSCA_P135_F | N | FANCE_P356_R | Y |
| JAK3_P1075_R | N | RUNX3_E27_R | N |
| STAT5A_P704_R | N | SERPINA5_P156_F | N |
| MST1R_E42_R | Y | HLA-DPA1_P205_R | N |
| HLA-DOB_E432_R | N | TNFSF8_P184_F | Y |
| EMR3_P39_R | N | DLC1_P88_R | N |
| NBLI_E205_R | N | | |
| NBLI_P24_F | N | | |
| ZIM3_P718_R | N | | |
| FGF1_P357_R | N | | |
| MAP3K8_P1036_F | Y | | |
| TGFB3_E58_R | N | | |
| AATK_E63_R | N | | |
| SERPINB5_P19_R | Y | | |
| MSH2_P1008_F | Y | | |
| CREBBP_P712_R | Y | | |
| MMP14_P13_F | Y | | |
| GRB7_P160_R | N | | |
| SFN_E118_F | Y | | |
| GLI2_E90_F | N | | |
| MST1R_P87_R | Y | | |
| TNFRSF1A_P678_F | N | | |
| GLI2_P295_F | Y | | |
| IL1RN_E42_F | N | | |
| BCR_P422_F | Y | | |
| CXCL9_E268_R | N | | |
| FGF1_E5_F | N | | |
| FER_P581_F | N | | |
| SEPT9_P58_R | Y | | |
| TRIM29_P135_F | N | | |
| SRC_P164_F | N | | |
| WEE1_P924_R | N | | |
| ALOX12_E85_R | Y | | |
| KCNK4_E3_F | Y | | |
| EGF_E339_F | N | | |
| S100A2_P1186_F | N | | |
| MOS_E60_R | Y | | |
| CD9_P585_R | Y | | |
| AATK_P519_R | Y | | |
| HOXA5_E187_F | Y | | |
| EPHA5_P66_F | Y | | |
| PTPN6_P282_R | N | | |
| CLDN4_P1120_R | N | | |
| SNCG_P98_R | Y | | |
| AATK_P709_R | Y | | |
| HOXA9_E252_R | Y | | |
| DHCR24_P652_R | N | | |
| CSF1R_P73_F | N | | |
| KRT5_P308_F | N | | |
| FRK_P36_F | N | | |
| EPHA2_P203_F | Y | | |
| IL1RN_P93_R | N | | |
| IFNGR2_P377_R | Y | | |
| RIPK3_P124_F | N | | |
| IL1213_P392_R | N | | |
| KLK11_P103_R | N | | |
| HS3ST2_E145_R | Y | | |
| HOXA9_P1141_R | Y | | |
| IGF1_E394_F | N | | |
| SLC14A1_P369_R | N | | |
| LEFTY2_P561_F | N | | |
| DDIT3_P1313_R | Y | | |
| PADI4_P1158_R | N | | |
| HOXA11_P698_F | Y | | |
| HOXI32_P99_F | Y | | |
| FASTK_P598_R | Y | | |
| TRIM29_E189_F | Y | | |
| LIG3_P622_R | N | | |
| SNCG_E119_F | N | | |
| SPDEF_P6_R | N | | |
| SNCG_P53_F | Y | | |
| CALCA_E174_R | Y | | |
| ALOX12_P223_R | Y | | |
| OGG1_E400_F | Y | | |
| HS3ST2_P171_F | Y | | |
| CEACAM1_P44_R | N | | |
| CALCA_P171_F | Y | | |
| DI3C1_E204_F | Y | | |
| DES_P1006_R | N | | |
| DDR1_P332_R | N | | |
| NPR2_P1093_F | Y | | |
| NID1_P677_F | N | | |
| GSTM2_P453_R | N | | |
| GRI37_E71_R | N | | |
| KCNK4_P171_R | N | | |
| HTR113_E232_R | Y | | |
| GFAP_P56_R | N | | |
| SOX1_P294_F | Y | | |
| IL1A_E113_R | N | | |
| PITX2_E24_R | Y | | |
| HOXA5_P479_F | Y | | |
| PAD14_P1011_11 | N | | |
| PLAT_E158_F | N | | |
| ASCL1_P747_F | Y | | |
| HTR1B_P222_F | Y | | |
| DSG1_E292_F | N | | |
| PRSS8_E134_11 | Y | | |
| AIM2_E208_F | N | | |
| CSF3_P309_11 | N | | |
| CHI3L2_E1O_F | N | | |
| SOX17_P303_F | Y | | |
| RARA_P176_11 | N | | |
| ZIM3_P451_11 | Y | | |
| DIO3_E230_11 | Y | | |
| DLK1_P227_11 | Y | | |
| ASB4_P391_F | N | | |
| SOX17_P287_11 | Y | | |
| CAPG_E228_F | N | | |
| CSF1R_E26_F | N | | |
| ARHGDIB_P148_11 | N | | |
| FZD9_E458_F | Y | | |
| CYP2E1_P416_F | N | | |
| THBS2_P605_11 | N | | |
| TAL1_P594_F | Y | | |
| MMP14_P208_11 | N | | |
| SEPT9_P374_F | Y | | |
| FGFR4_P610_F | N | | |
| ZP3_P220_F | N | | |
| IGFBP5_P9_11 | N | | |
| SEPT5_P441_F | Y | | |
| SPARC_P195_F | N | | |
| S100A4_E315_F | N | | |
| PENK_P447_11 | Y | | |
| S100A2_E36_11 | N | | |
| PTHR1_P258_F | N | | |
| TNFRSF10C_P7_F | Y | | |
| CD9_P504_F | Y | | |
| RAD5O_P191_F | Y | | |
| MYH11_P22_F | Y | | |
| IHH_E186_F | Y | | |
| BMP4_P199_11 | Y | | |
| DCC_P471_R | Y | | |
| PTPRH_E173_F | N | | |
| BCR_P346_F | Y | | |
| EYA4_E277_F | Y | | |
| SERPINE1_P519_F | N | | |
| PTK6_E50_F | Y | | |
| TBX1_P885_R | Y | | |
| ESR1_P151_R | Y | | |
| CD81_P272_R | Y | | |

| Head and neck cancer (hypermethylation) (n:171) | CGI | Head and neck cancer (hypomethylation) (n:20) | CGI |
|---|---|---|---|
| SEMA3A_P658_R | N | | |
| TGFBI_P173_F | Y | | |
| HGF_E102_R | N | | |
| CTSL_P264_R | Y | | |
| TNK1_P221_F | Y | | |
| NOTCH3_P198_R | Y | | |
| VAMP8_P114_F | N | | |
| EPHA2_P340_R | N | | |
| BAX_E281_R | Y | | |
| CPA4_E20_F | N | | |
| CD82_P557_R | Y | | |
| IGFBP3_P423_R | Y | | |
| CTSD_P726_F | Y | | |
| MYOD1_E156_F | Y | | |
| SEPT5_P464_R | Y | | |
| TPEF_seq_44_588_R | Y | | |
| CPA4_P1265_R | N | | | or in Table 2B

| Head and neck cancer (hypermethylation) (n:97) | CGI | Head and neck cancer (hypomethylation) (n:10) | CGI |
|---|---|---|---|
| LCN2_P141_R | N | ERN1_P809_R | Y |
| PI3_P274_R | N | MT1A_P600_F | Y |
| KRT13_P341_R | N | DLC1_E276_F | N |
| SLC22A18_P216_R | N | RAB32_P493_R | Y |
| TMPRSS4_E83_F | N | ICAM1_P386_R | Y |
| VAMP8_P241_F | N | JAK3_P156_R | N |
| KRT5_E196_R | Y | TNFSF8_E258_R | N |
| TRIP6_P1274_R | Y | FANCE_P356_R | Y |
| DSG1_P159_R | N | SERPINA5_P156_F | N |
| LY6G6E_P45_R | N | DLC1_P88_R | N |
| PSCA_P135_F | N | | |
| JAK3_P1075_R | N | | |
| MST1R_E42_R | Y | | |
| HLA-DOB_E432_R | N | | |
| EMR3_P39_R | N | | |
| NBL1_E205_R | N | | |
| NBL1_P24_F | N | | |
| ZIM3_P718_R | N | | |
| FGF1_P357_R | N | | |
| MAP3K8_P1036_F | Y | | |
| AATK_E63_R | N | | |
| SERPINB5_P19_R | Y | | |
| MSH2_P1008_F | Y | | |
| CREBBP_P712_R | Y | | |
| MMP14_P13_F | Y | | |
| GRB7_P160_R | N | | |
| SFN_E118_F | Y | | |
| GLI2_E90_F | N | | |
| MST1R_P87_R | Y | | |
| TNFRSF1A_P678_F | N | | |
| GLI2_P295_F | Y | | |
| IL1RN_E42_F | N | | |
| CXCL9_E268_R | N | | |
| FGF1_E5_F | N | | |
| FER_P581_F | N | | |
| SEPT9_P58_R | Y | | |
| TRIM29_P135_F | N | | |
| SRC_P164_F | N | | |
| WEE1_P924_R | N | | |
| EGF_E339_F | N | | |
| AATK_P519_R | Y | | |
| CLDN4_P1120_R | N | | |
| CSF1R_P73_F | N | | |
| KRT5_P308_F | N | | |
| FRK_P36_F | N | | |
| EPHA2_P203_F | Y | | |
| RIPK3_P124_F | N | | |
| IL12B_P392_R | N | | |
| KLK11_P103_R | N | | |
| IGF1_E394_F | N | | |

| Head and neck cancer (hypermethylation) (n:97) | CGI | Head and neck cancer (hypomethylation) (n:10) | CGI |
|---|---|---|---|
| PADI4_P1158_R | N | | |
| HOXB2_P99_F | Y | | |
| FASTK_P598_R | Y | | |
| TRIM29_E189_F | Y | | |
| LIG3_P622_R | N | | |
| SPDEF_P6_R | N | | |
| OGG1_E400_F | Y | | |
| CEACAM1_P44_R | N | | |
| CALCA_P171_F | Y | | |
| DES_P1006_R | N | | |
| NPR2_P1093_F | Y | | |
| NID1_P677_F | N | | |
| KCNK4_P171_R | N | | |
| GFAP_P56_F | N | | |
| IL1A_E113_R | N | | |
| HOXA5_P479_F | Y | | |
| PAD14_P1011_R | N | | |
| PLAT_E158_F | N | | |
| DSG1_E292_F | N | | |
| PRSS8_E134_R | Y | | |
| AIM2_E208_F | N | | |
| CSF3_P309_R | N | | |
| ZIM3_P451_R | Y | | |
| ASB4_P391_F | N | | |
| CAPG_E228_F | N | | |
| CSF1R_E26_F | N | | |
| CYP2E1_P416_F | N | | |
| THBS2_P605_R | N | | |
| MMP14_P208_R | N | | |
| FGFR4_P610_F | N | | |
| ZP3_P220_F | N | | |
| S100A4_E315_F | N | | |
| S100A2_E36_R | N | | |
| PTHR1_P258_F | N | | |
| RAD5O_P191_F | Y | | |
| PTPRH_E173_F | N | | |
| PTK6_E50_F | Y | | |
| SEMA3A_P658_R | N | | |
| HGF_E102_R | N | | |
| CTSL_P264_R | Y | | |
| TNK1_P221_F | Y | | |
| VAMP8_P114_F | N | | |
| EPHA2_P340_R | N | | |
| CPA4_E20_F | N | | |
| CD82_P557_R | Y | | |
| CTSD_P726_F | Y | | |
| CPA4_P1265_R | N | | | is compared with the methylation status of a head and neck cancer, wherein CGI is CpG island associated, Y is yes, and N is not.

6. The method according to claim 2, wherein detecting the methylation status comprises detecting the methylation status in one or more CpG sites as defined in Tables 3A and 3B, wherein the methylation status in one or more CpG sites as defined in Table 3A

| Pancreatic cancer (hypermethylation) (n:150) | CGI | Pancreatic cancer (hypomethylation) (n:98) | CGI |
|---|---|---|---|
| CDH13_E102_F | Y | SERPINB5_P19_R | Y |
| GAS7_E148_F | Y | S100A2_P1186_F | N |
| TWIST1_E117_R | Y | PI3_P274_R | N |
| CCNA1_P216_F | Y | SFN_E118_F | Y |
| SLIT2_P208_F | Y | IAPP_E280_F | N |
| FLT3_E326_R | Y | TRIM29_P135_F | N |
| CCNA1_E7_F | Y | PTPRH_P255_F | N |
| NPY_P295_F | Y | NOS2A_E117_R | N |
| GALR1_E52_F | Y | CYP2E1_P416_F | N |
| WT1_E32_F | Y | SFTPA1_E340_R | N |
| RASGRF1_E16_F | Y | CREBBP_P712_R | Y |
| SFRP1_E398_R | Y | NDN_P1110_F | N |

| Pancreatic cancer (hypermethylation) (n:150) | CGI | Pancreatic cancer (hypomethylation) (n:98) | CGI |
|---|---|---|---|
| TPEF_seq_44_S88_R | Y | TRIM29_E189_F | Y |
| MYOD1_E156_F | Y | CSF2_E248_R | N |
| NTRK3_P636_R | Y | ITK_P114_F | N |
| MDR1_seq_42_S300_R | Y | TRIM29_P261_F | N |
| DBC1_P351_R | Y | TRIP6_P1090_F | Y |
| EYA4_E277_F | Y | IL1RN_E42_F | N |
| FGF8_P473_F | Y | SEPT9_P58_R | Y |
| HS3ST2_P171_F | Y | GLI2_P295_F | Y |
| SOX1_P294_F | Y | TFF2_P178_F | N |
| CDH13_P88_F | Y | CXCL9_E268_R | N |
| NTRK3_P752_F | Y | TFF1_P180_R | N |
| SEZ6L_P249_F | Y | MST1R_E42_R | Y |
| NTRK3_E131_F | Y | PI3_E107_F | N |
| DLK1_E227_R | Y | GLI2_E90_F | N |
| HOXA9_P1141_R | Y | NBL1_P24_F | N |
| SOX17_P303_F | Y | CSF2_P605_F | N |
| MYH11_P22_F | Y | NOS3_P38_F | N |
| SOX1_P1018_R | Y | TMPRSS4_P552_F | N |
| HIC2_P498_F | Y | UGT1A1_P315_R | N |
| MOS_E60_R | Y | NID1_P677_F | N |
| IGFBP3_P423_R | Y | NBL1_E205_R | N |
| ERG_E28_F | Y | S100A2_E36_R | N |
| HS3ST2_E145_R | Y | LCN2_P141_R | N |
| FLT1_P302_F | Y | UGT1A1_E11_F | N |
| TBX1_P885_R | Y | PRSS1_E45_R | N |
| TAL1_P594_F | Y | IFNG_E293_F | N |
| SOX17_P287_R | Y | NCL_P1102_F | Y |
| HOXA9_E252_R | Y | APBA2_P305_R | N |
| ADCYAP1_P398_F | Y | SPI1_P929_F | N |
| TMEFF2_P152_R | Y | FGFR4_P610_F | N |
| PENK_P447_R | Y | SRC_P164_F | N |
| MMP2_P303_R | Y | SEPT9_P374_F | Y |
| BMP3_P56_R | Y | EMR3_P39_R | N |
| COL1A2_E299_F | Y | KRT1_P798_R | N |
| TFPI2_P9_F | Y | PRSS8_E134_R | Y |
| NGFB_E353_F | Y | MST1R_P87_R | Y |
| TUSC3_E29_R | Y | CPA4_E20_F | N |
| FLT1_P615_R | Y | IFNG_P188_F | N |
| CHGA_E52_F | Y | NOS2A_P288_R | N |
| GABRB3_E42_F | Y | SLC22A3_P634_F | Y |
| SFRP1_P157_F | Y | KIAA0125_E29_F | N |
| NEFL_P209_R | Y | NOTCH4_E4_F | N |
| SEZ6L_P299_F | Y | SNCG_E119_F | N |
| ASCL2_P360_F | Y | ZP3_P220_F | N |
| HS3ST2_P546_F | Y | PTK6_E50_F | Y |
| FLT4_P180_R | Y | CLDN4_P1120_R | N |
| EPHA5_E158_R | Y | MPO_E302_R | N |
| FLT1_E444_F | Y | BRCA1_P835_R | Y |
| GABRB3_P92_F | Y | LCN2_P86_R | N |
| ESR1_P151_R | Y | GUCY2F_P255_F | N |
| CCND2_P898_R | Y | PTPRH_E173_F | N |
| RET_seq_53_S374_F | Y | PTPN6_P282_R | N |
| NEFL_E23_R | Y | GML_P281_R | N |
| COL1A2_P48_R | Y | PSCA_P135_F | N |
| EYA4_P794_F | Y | LIG3_P622_R | N |
| SLC5A8_E60_R | Y | CEACAM1_P44_R | N |
| SLIT2_E111_R | Y | WNT8B_E487_F | N |
| FLI1_E29_F | Y | BMP4_P199_R | Y |
| WT1_P853_F | Y | GABRG3_E123_R | N |
| KDR_P445_R | Y | MAPK4_E273_R | N |
| MYH11_P236_R | Y | CAPG_E228_F | N |
| HOXA11_P698_F | Y | FGF1_P357_R | N |
| THY1_P149_R | Y | DLC1_P695_F | N |
| ADAMTS12_E52_R | Y | VAMP8_P241_F | N |
| SCGB3A1_E55_R | Y | APOA1_P261_F | N |
| ESR1_E298_R | Y | MAGEC3_E307_F | N |
| TMEFF2_E94_R | Y | CCR5_P630_R | N |
| PROK2_P390_F | Y | PWCR1_P811_F | N |
| KIT_P367_R | Y | TRIP6_P1274_R | Y |
| HOXA9_P303_F | Y | CASP8_E474_F | N |
| NPY_E31_F | Y | CTLA4_P1128_F | N |
| TFPI2_P152_R | Y | GABRA5_P862_R | N |
| TFPI2_E141_F | Y | GFAP_P56_R | N |
| PITX2_E24_R | Y | MMP10_E136_R | N |
| DES_E228_R | Y | KLK10_P268_R | N |
| ASCL1_E24_F | Y | IL12B_P1453_F | Y |
| GSTM2_E153_F | Y | PAD14_P1011_R | N |
| NPY_P91_F | Y | PWCR1_P357_F | N |
| FZD9_E458_F | Y | AATK_E63_R | N |
| TIMP3_seq_7_538_F | Y | HLA-DOB_E432_R | N |
| NGFB_P13_F | Y | IL1RN_P93_R | N |
| MMP2_P197_F | Y | FRK_P36_F | N |
| DBC1_E204_F | Y | EPHA2_P203_F | Y |
| GSTM2_P109_R | N | SPP1_P647_F | N |
| CDH11_E102_R | Y | PTHR1_P258_F | N |
| ADCYAP1_P455_R | Y | BAX_E281_R | Y |
| COL1A1_P5_F | Y | | |
| TWIST1_P355_R | Y | | |
| ATP10A_P147_F | Y | | |
| FRZB_E186_R | Y | | |
| SMO_P455_R | Y | | |
| CALCA_E174_R | Y | | |
| HCK_P858_F | Y | | |
| PENK_E26_F | Y | | |
| MMP2_E21_R | Y | | |
| TIAM1_P117_F | Y | | |
| TSP5O_P137_F | Y | | |
| PTCH2_P568_R | Y | | |
| BMP3_E147_F | Y | | |
| GUCY2D_E419_R | Y | | |
| ASCL2_P609_R | Y | | |
| GDF1O_P95_R | Y | | |
| CCND2_P887_F | Y | | |
| GDF1O_E39_F | Y | | |
| FLT3_P302_F | Y | | |
| IGFBP7_P297_F | Y | | |
| SLC5A8_P38_11 | Y | | |
| FGF5_E16_F | Y | | |
| CALCA_P75_F | Y | | |
| POMC_P53_F | Y | | |
| DCC_E53_11 | Y | | |
| KIT_P405_F | Y | | |
| ZIM2_P22_F | Y | | |
| ASCL1_P747_F | Y | | |
| TUSC3_P85_11 | Y | | |
| TMEFF1_P234_F | Y | | |
| POMC_P400_11 | Y | | |
| POMC_E254_F | Y | | |
| FGF3_E198_11 | Y | | |
| BDNF_E19_11 | Y | | |
| EYA4_P508_F | Y | | |
| ROR2_E112_F | Y | | |
| SGCE_E149_F | Y | | |
| HCK_P46_11 | Y | | |
| ADCYAP1_E163_11 | Y | | |
| TPEF_seq_44_536_F | Y | | |
| ADAMTS12_P250_11 | Y | | |
| HOXA5_E187_F | Y | | |
| NRG1_E74_F | Y | | |
| MCAM_P265_11 | Y | | |
| ER_seq_a1_560_F | Y | | |
| MT1A_P600_F | Y | | |
| GSTM1_P266_F | Y | | |
| GSTM2_P453_11 | N | | |
| EPHA5_P66_F | Y | | |
| MFAP4_P197_F | N | | |
| RET_P717_F | Y | | |
| HIC2_P528_11 | Y | | | or in Table 3B

| Pancreatic cancer (hypermethylation) (n:150) | CGI | Pancreatic cancer (hypomethylation) (n:98) | CGI |
|---|---|---|---|
| FGF8_P473_F | Y | CYP2E1_P416_F | N |
| SEZ6L_P249_F | Y | CREBBP_P712_R | Y |
| FLT1_P302_F | Y | NDN_P1110_F | N |
| FLT1_P615_R | Y | CSF2_E248_R | N |
| SEZ6L_P299_F | Y | SEPT9_P58_R | Y |
| FLT1_E444_F | Y | TFF1_P180_R | N |

-continued

| Pancreatic cancer (hypermethylation) (n:150) | CGI | Pancreatic cancer (hypomethylation) (n:98) | CGI |
|---|---|---|---|
| NEFL_E23_R | Y | CSF2_P605_F | N |
| COL1A2_P48_R | Y | LCN2_P141_R | N |
| MYH11_P236_R | Y | UGT1A1_E11_F | N |
| MMP2_P197_F | Y | NCL_P1102_F | Y |
| COL1A1_P5_ | Y | SPI1_P929_F | N |
| SMO_P455_ | Y | FGFR4_P610_F | N |
| PTCH2_P568R | Y | SEPT9_P374_F | Y |
| GDF1O_P95_R | Y | MST1R_P87_R | N |
| GDF1O_E39_ | Y | SLC22A3_P634_F | Y |
| POMC_P53_F | Y | KIAA0125_E29_F | N |
| ZIM2_P22_F | Y | SNCG_E119_F | N |
| TMEFF1_P234_F | Y | GUCY2F_P255_F | N |
| POMC_E254_F | Y | GML_P281_R | N |
| FGF3_E198_R | Y | LIG3_P622_R | N |
| SGCE_E149_F | Y | WNT8B_E487_F | N |
| ADCYAP1_E163_R | Y | BMP4_P199_R | Y |
| TPEF_seq_44_536_F | Y | GABRG3_E123_R | N |
| MCAM_P265_R | Y | MAPK4_E273_R | N |
| RET_P717_F | N | FGF1_P357_R | N |
| HIC2_P528_R | Y | APOA1_P261_F | N |
|  |  | PWCR1_P811_F | N |
|  |  | CTLA4_P1128_F | N |
|  |  | GFAP_P56_R | N |
|  |  | KLK10_P268_R | N |
|  |  | PWCR1_P357_F | N |
|  |  | IL1RN_P93_R | N |
|  |  | FRK_P36_F | N |
|  |  | EPHA2_P203_F | Y | is compared with the methylation status of a pancreatic cancer, wherein CGI is CpG island associated, Y is yes, and N is not.

7. The method according to claim 2, wherein detecting the methylation status comprises detecting the methylation status in one or more CpG sites as defined in Tables 4A and 4B, wherein the methylation status in one or more CpG sites as defined in Table 4A

| Endometrial cancer hypermethylation (n:102) | CGI | Endometrial cancer hypomethylation (n:22) | CGI |
|---|---|---|---|
| PENK_E26_F | Y | BLK_P14_F | N |
| DLK1_E227_R | Y | IFNG_E293_F | N |
| SOX1_P294_F | Y | MEST_P62_R | Y |
| NEFL_P209_R | Y | EMR3_E61_F | N |
| HTR1B_P222_F | Y | PTHLH_E251_F | N |
| NPY_P295_F | Y | NBL1_P24_F | N |
| CDH13_P88_F | Y | SPP1_P647_F | N |
| CDH13_E102_F | Y | CEACAM1_P44_R | N |
| HTR1B_E232_R | Y | WIST1R_E42_R | Y |
| DCC_P471_R | Y | NID1_P677_F | N |
| ADCYAP1_P455_R | Y | PTHLH_P15_R | N |
| ADCYAP1_P398_F | Y | MEST_P4_F | Y |
| TPEF_seq_44_S88_R | Y | PI3E107F | N |
| NPY_E31_R | Y | PTPN6_P282_R | N |
| PENK_P447_R | Y | PTPRH_E173_F | N |
| HS3ST2_E145_R | Y | EMR3_P39_R | N |
| HS3ST2_P171_F | Y | IL2_P607_R | N |
| CFTR_P372_R | Y | CLDN4_P1120_R | N |
| DBC1_E204_F | Y | TRIP6_P1090_F | Y |
| ASCL2_P360_F | Y | ASB4_P52_R | N |
| MOS_E60_R | Y | GFI1_P208_R | Y |
| TERT_P360_R | Y | TRIP6_P1274_R | Y |
| EPHA5_E158_R | Y |  |  |
| DBC1_P351_R | Y |  |  |
| OPCML_E219_R | Y |  |  |
| DIO3_P674_F | Y |  |  |
| DCC_P177_F | Y |  |  |
| SOX1_P1018_R | Y |  |  |
| THY1_P149_R | Y |  |  |
| RASSF1_E116_F | Y |  |  |
| ASCL1_P747_F | Y |  |  |
| GSTM2_E153_F | Y |  |  |

-continued

| Endometrial cancer hypermethylation (n:102) | CGI | Endometrial cancer hypomethylation (n:22) | CGI |
|---|---|---|---|
| SLC5A8_E60_R | Y |  |  |
| MYOD1_E156_F | Y |  |  |
| ISL1_E87_R | Y |  |  |
| GUCY2D_E419_R | Y |  |  |
| HOXA9_E252_R | Y |  |  |
| HCK_P858_F | Y |  |  |
| ZNF215_P129_R | Y |  |  |
| PRKCDBP_E206_F | Y |  |  |
| SEPT9_P374_F | Y |  |  |
| PLS3_E70_F | Y |  |  |
| CD4O_P372_R | Y |  |  |
| TMEFF2_E94_R | Y |  |  |
| CALCA_E174_R | Y |  |  |
| GSTM1_P266_F | Y |  |  |
| CYP1B1_E83_R | Y |  |  |
| SPARC_P195_F | N |  |  |
| SLC22A3_E122_R | Y |  |  |
| TMEFF2_P152_R | Y |  |  |
| ISL1_P379_F | Y |  |  |
| D103_P90_F | Y |  |  |
| NTRK3_P752_F | Y |  |  |
| RASSF1_P244_F | Y |  |  |
| HOXA11_P698_F | Y |  |  |
| AGTR1_P41_F | Y |  |  |
| MLF1_E243_F | Y |  |  |
| EYA4_E277_F | Y |  |  |
| HLA-F_E402_F | Y |  |  |
| NTRK3_P636_R | Y |  |  |
| FLI1_E29_F | Y |  |  |
| BDNF_E19_R | Y |  |  |
| TJP2_P330_R | Y |  |  |
| TSP5O_P137_F | Y |  |  |
| ISL1_P554_F | Y |  |  |
| ABO_P312_F | Y |  |  |
| STAT5A_E42_F | N |  |  |
| FGF2_P229_F | Y |  |  |
| MFAP4_P10_R | N |  |  |
| MME_E29_F | Y |  |  |
| MDR1_seq_42_S300_R | Y |  |  |
| MLH1_P381_F | Y |  |  |
| GSTM2_P109_R | N |  |  |
| GSTM2_P453_R | N |  |  |
| NTSR1_P318_F | Y |  |  |
| JAK3_E64_F | Y |  |  |
| NRG1_P558_R | Y |  |  |
| TUSC3_E29_R | Y |  |  |
| ZNF215_P71_R | Y |  |  |
| APC_P14_F | Y |  |  |
| GABRB3_E42_F | Y |  |  |
| NTRK3_E131_F | Y |  |  |
| IRAK3_P185_F | Y |  |  |
| TIMP3_seq_7_538_F | Y |  |  |
| TAL1_P594_F | Y |  |  |
| WT1_P853_F | Y |  |  |
| BMP3_P56_R | Y |  |  |
| MMP2_P303_R | Y |  |  |
| BMP3_E147_F | Y |  |  |
| IRAK3_P13_F | Y |  |  |
| IRAK3_E130_F | Y |  |  |
| EPHA3_P106_R | Y |  |  |
| CD9_P585_R | Y |  |  |
| FRZB_E186_R | Y |  |  |
| WNT2_P217_F | Y |  |  |
| TNFRSF10D_E27_F | Y |  |  |
| WT1_E32_F | Y |  |  |
| DAB2IP_E18_R | Y |  |  |

-continued

| Endometrial cancer hypermethylation (n:102) | CGI | Endometrial cancer hypomethylation (n:22) | CGI |
|---|---|---|---|
| TIAM1_P117_F | Y | | |
| CDH11_P354_R | Y | | |
| PITX2_E24_R | Y | | |
| CHFR_P501_F | Y | | | or in Table 4B

| Endometrial cancer (hypermethylation) (n:102) | CGI | Endometrial cancer (hypomethylation) (n:22) | CGI |
|---|---|---|---|
| HLA-F_E402_F | Y | PTHLH_E251_F | N |
| ABO_P312_F | Y | PTHLH_P15_R | N |
| MLH1_P381_F | Y | IL2_P607_R | N |
| JAK3_E64_F | Y | ASB4_P52_R | N |
| | | GFI1_P208_R | Y | is compared with the methylation status of a endometrial cancer, wherein CGI is CpG island associated, Y is yes, and N is not.

8. The method according to claim 2, wherein detecting the methylation status comprises detecting the methylation status in one or more CpG sites as defined in Tables 5A and 5B, wherein the methylation status in one or more CpG sites as defined in Table 5A

| Colon cancer (hypermethylation) (96) | CGI | Colon cancer (hypomethylation) (3) | CGI |
|---|---|---|---|
| EYA4_E277_F | Y | PI3_E107_F | N |
| TWIST1_E117_R | Y | NEU1_P745_F | Y |
| SFRP1_P157_F | Y | S100A2_E36_R | N |
| SLIT2_E111_R | Y | | |
| TMEFF2_E94_R | Y | | |
| SFRP1_E398_R | Y | | |
| NPY_E31_R | Y | | |
| TFP12_P9_F | Y | | |
| NPY_P295_F | Y | | |
| TFP12_P152_R | Y | | |
| FLT4_P180_R | Y | | |
| HS3ST2_E145_R | Y | | |
| SLIT2_P208_F | Y | | |
| DAB2IP_E18_R | Y | | |
| GAS7_E148_F | Y | | |
| NGFB_P13_F | Y | | |
| TMEFF2_P152_R | Y | | |
| NTSR1_P318_F | Y | | |
| FLI1_E29_F | Y | | |
| GSTM2_E153_F | Y | | |
| RASGRF1_E16_F | Y | | |
| MME_E29_F | Y | | |
| NGFB_E353_F | Y | | |
| EYA4_P794_F | Y | | |
| FGF5_P238_R | Y | | |
| CD4O_P372_R | Y | | |
| WNT2_P217_F | Y | | |
| IGFBP3_P423_R | Y | | |
| NTRK3_P752_F | Y | | |
| WT1_E32_F | Y | | |
| SCGB3A1_E55_R | Y | | |
| HS3ST2_P171_F | Y | | |
| AGTR1_P41_F | Y | | |
| DBC1_E204_F | Y | | |
| FLT3_E326_R | Y | | |
| TBX1_P885_R | Y | | |
| DLK1_E227_R | Y | | |
| CDH13_P88_F | Y | | |
| TPEF_seq_44_588_R | Y | | |
| ESR1_E298_R | Y | | |
| NTRK3_E131_F | Y | | |
| THY1_P149_R | Y | | |

-continued

| Colon cancer (hypermethylation) (96) | CGI | Colon cancer (hypomethylation) (3) | CGI |
|---|---|---|---|
| NPY_P91_F | Y | | |
| ER_seq_a1_560_F | Y | | |
| ALK_E183_R | Y | | |
| FGF5_E16_F | Y | | |
| ALK_P28_F | Y | | |
| TWIST1_P355_11 | Y | | |
| ADCYAP1_P398_F | Y | | |
| ESR1_P151_11 | Y | | |
| SOX17_P287_11 | Y | | |
| IRAK3_P13_F | Y | | |
| GABRB3_P92_F | Y | | |
| SOX1_P294_F | Y | | |
| HOXA5_E187_F | Y | | |
| HTR1B_E232_11 | Y | | |
| EPHA5_E158_11 | Y | | |
| CDH13_E102_F | Y | | |
| MOS_E60_R | Y | | |
| MYOD1_E156_F | Y | | |
| CHFR_P501_F | Y | | |
| EYA4_P508_F | Y | | |
| HIC-1_seq_48_5103_11 | Y | | |
| CYP1B1_E83_11 | Y | | |
| KDR_P445_11 | Y | | |
| MYH11_P22_F | Y | | |
| ADAMTS12_E52_11 | Y | | |
| NTRK3_P636_11 | Y | | |
| DCC_P471_11 | Y | | |
| TUSC3_E29_11 | Y | | |
| KDR_E79_F | Y | | |
| CSPG2_E38_F | Y | | |
| PENK_P447_11 | Y | | |
| HCK_P858_F | Y | | |
| ADCYAP1_P455_11 | Y | | |
| CSPG2_P82_11 | Y | | |
| NRG1_P558_11 | Y | | |
| IGF2AS_E4_F | Y | | |
| GABRB3_E42_F | Y | | |
| CCNA1_P216_F | Y | | |
| SOX17_P303_F | Y | | |
| CDH11_P354_R | Y | | |
| FGF3_P171_R | Y | | |
| GSTM2_P109_R | N | | |
| DBC1_P351_R | Y | | |
| OPCML_E219_R | Y | | |
| WT1_P853_F | Y | | |
| COL1A2_E299_F | Y | | |
| TFPI2_E141_F | Y | | |
| PDE1B_P263_R | Y | | |
| IRAK3_E130_F | Y | | |
| HS3ST2_P546_F | Y | | |
| MMP2_P303_R | Y | | |
| NEFL_P209_R | Y | | |
| TIAM1_P117_F | Y | | |
| TUSC3_P85_R | Y | | | or in Table 5B

| Colon cancer (hypermethylation) (3) | CGI | Colon cancer (hypomethylation) (1) | CGI |
|---|---|---|---|
| ALK_P28_F | Y | NEU1_P745_F | Y |
| CSPG2_E38_F | Y | | |
| PDE1B_P263_11 | Y | | | is compared with the methylation status of a colon cancer, wherein CGI is CpG island associated, Y is yes, and N is not.

9. The method according to claim 2, wherein detecting the methylation status comprises detecting the methylation status in one or more CpG sites as defined in Tables 6A and 6B, wherein the methylation status in one or more CpG sites as defined in Table 6A

| Prostate cancer (hypermethylation) (n:76) | CGI | Prostate cancer (hypomethylation) (n:4) | CGI |
|---|---|---|---|
| GSTP1_E322_R | Y | MEST_P4_F | Y |
| GSTM2_E153_F | Y | DLC1_P695_F | N |
| RARB_P60_F | Y | MEST_P62_R | Y |
| COL18A1_P494_R | Y | PTPN6_P282_R | N |
| PDGFRB_P273_F | Y | | |
| APC_P14_F | Y | | |
| MFAP4_P10_R | N | | |
| SCGB3A1_E55_R | Y | | |
| ALOX12_P223_R | Y | | |
| POMC_P400_R | Y | | |
| ALOX12_E85_R | Y | | |
| GSTM2_P109_R | N | | |
| PDGFRB_E195_R | N | | |
| TJP2_P330_R | Y | | |
| IGFBP7_P297_F | Y | | |
| GSTP1_P74_F | Y | | |
| GSTP1_seq_38_S153_R | Y | | |
| RARA_P176_R | N | | |
| RARB_E114_F | Y | | |
| NEU1_P745_F | Y | | |
| ADAMTS12_E52_R | Y | | |
| TRIP6_E33_F | Y | | |
| SERPINE1_E189_R | Y | | |
| SEPT9_P374_F | Y | | |
| MFAP4_P197_F | N | | |
| ADAMTS12_P250_R | Y | | |
| CFTR_P372_R | Y | | |
| KIT_P367_R | Y | | |
| PDGFRB_P343_F | Y | | |
| TERT_P360_R | Y | | |
| GSTM2_P453_R | N | | |
| CD4O_P372_R | Y | | |
| HFE_E273_R | Y | | |
| RASSF1_E116_F | Y | | |
| HHIP_E94_F | Y | | |
| TBX1_P885_R | Y | | |
| NOTCH4_E4_F | N | | |
| FGF2_P229_F | Y | | |
| HDAC9_E38_F | N | | |
| SPARC_P195_F | N | | |
| CD9_P585_R | Y | | |
| KIT_P405_F | Y | | |
| APC_E117_R | Y | | |
| RBP1_P426_R | Y | | |
| HDAC9_P137_R | N | | |
| EYA4_E277_F | Y | | |
| SERPINE1_P519_F | N | | |
| GADD45A_P737_R | N | | |
| NGFR_P355_F | Y | | |
| COL1A2_E299_F | Y | | |
| PTGS2_P524_R | Y | | |
| APC_P280_R | Y | | |
| SPARC_E50_R | Y | | |
| SLC14A1_P369_R | N | | |
| SNCG_E119_F | N | | |
| CDKN1B_P1161_F | N | | |
| CSPG2_P82_R | Y | | |
| PTCH2_E173_F | Y | | |
| PYCARD_P150_F | Y | | |
| CCND2_P887_F | Y | | |
| KLK1O_P268_R | N | | |
| TMEFF1_P626_R | Y | | |
| TRIM29_P261_F | N | | |
| PYCARD_E87_F | Y | | |
| PYCARD_P393_F | N | | |
| CCND2_P898_R | Y | | |
| LEFTY2_P561_F | N | | |
| CHI3L2_E1O_F | N | | |
| CD9_P504_F | Y | | |
| VIM_P811_R | Y | | |
| CDH13_E102_F | Y | | |
| RARA_E128_R | N | | |
| IFNGR2_P377_R | Y | | |
| TEK_E75_F | N | | |
| SLC14A1_E295_F | N | | |
| SLC5A5_E60_F | Y | | | or in Table 6B

| Prostate cancer (hypermethylation) (n:28) | CGI |
|---|---|
| RARB_P60_F | Y |
| PDGFRB_P273_F | Y |
| PDGFRB_E195_R | N |
| GSTP1_P74_F | Y |
| GSTP1_seq_38_S153_R | Y |
| RARB_E114_F | Y |
| NEU1_P745_F | Y |
| TRIP6_E33_F | Y |
| SERPINE1_E189_R | Y |
| PDGFRB_P343_F | Y |
| HFE_E273_R | Y |
| HHIP_E94_F | Y |
| HDAC9_E38_F | N |
| HDAC9_P137_R | N |
| GADD45A_P737_R | N |
| NGFR_P355_F | Y |
| APC_P280_R | Y |
| SPARC_E50_R | Y |
| CDKN1B_P1161_F | N |
| PTCH2_E173_F | Y |
| KLK1O_P268_R | N |
| TMEFF1_P626_R | Y |
| PYCARD_E87_F | Y |
| PYCARD_P393_F | N |
| VIM_P811_R | Y |
| RARA_E128_R | N |
| SLC14A1_E295_F | N |
| SLC5A5_E60_F | Y | is compared with the methylation status of a prostate cancer, wherein CGI is CpG island associated, Y is yes, and N is not.

10. The method according to claim 2, wherein detecting the methylation status comprises detecting the methylation status in one or more CpG sites as defined in Tables 7A and 7B, wherein the methylation status in one or more CpG sites as defined in Table 7A

| Glioma hypermethylation (n: 66) | CGI | Glioma hypomethylation (n: 64) | CGI |
|---|---|---|---|
| FZD9_E458_F | Y | MPO_P883_R | N |
| HOXA11_P698_F | Y | IL8_E118_R | N |
| TES_P182_F | Y | NOTCH4_E4_F | N |
| HOXA9_E252_R | Y | CASP10_P334_F | N |
| CD81_P272_R | Y | SERPINE1_P519_F | N |
| HTR1B_E232_R | Y | MMP14_P13_F | Y |
| TNFRSF10A_P171_F | Y | CCL3_E53_R | N |
| TNFRSF10A_P91_F | Y | CASP10_P186_F | N |
| HOXA9_P1141_R | Y | S100A2_E36_R | N |
| TES_E172_F | Y | HLA-DPA1_P205_R | N |
| TAL1_P594_F | Y | MMP9_P189_F | N |
| HTR1B_P222_F | Y | JAK3_P1075_R | N |
| FLT3_E326_R | Y | TRIP6_P1090_F | Y |
| AHR_P166_R | Y | PTHR1_P258_F | N |
| GATA6_P21_R | Y | TRIP6_P1274_R | Y |
| MEST_E150_F | Y | PADI4_P1011_R | N |
| IRAK3_E130_F | Y | MMP2_P303_R | Y |
| PENK_E26_F | Y | CSF3R_P8_F | N |
| MOS_E60_R | Y | S100A2_P1186_F | N |

| Glioma hypermethylation (n: 66) | CGI | Glioma hypomethylation (n: 64) | CGI |
|---|---|---|---|
| NEFL_P209_R | Y | SH3BP2_E18_F | N |
| HOXA11_E35_F | Y | GSTM2_E153_F | Y |
| NPY_P295_F | Y | EMR3_P39_R | N |
| GATA6_P726_F | Y | PSCA_E359_F | N |
| TNFRSF10D_E27_F | Y | HDAC1_P414_R | Y |
| DSC2_E90_F | Y | CASP10_E139_F | N |
| HOXA5_E187_F | Y | PRSS1_E45_R | N |
| DIO3_P674_F | Y | ALPL_P433_F | Y |
| ALOX12_E85_R | Y | RIPK3_P24_F | N |
| ISL1_P379_F | Y | EMR3_E61_F | N |
| TFAP2C_P765_F | Y | RIPK3_P124_F | N |
| IRAK3_P13_F | Y | TMPRSS4_P552_F | N |
| MEST_P62_R | Y | HLA-DPA1_P28_R | N |
| IRAK3_P185_F | Y | GFAP_P1214_F | N |
| PCTK1_E77_R | Y | LEFTY2_P561_F | N |
| GFI1_P45_R | Y | STAT5A_P704_R | N |
| NPY_E31_R | Y | CD86_P3_F | N |
| DIO3_E230_R | Y | TNFSF10_E53_F | N |
| DDIT3_P1313_R | Y | NOS2A_P288_R | N |
| FLT3_P302_F | Y | KLK11_P103_R | N |
| MEST_P4_F | Y | FGFR2_P460_R | Y |
| IPF1_P750_F | Y | SPDEF_P6_R | N |
| TUSC3_E29_R | Y | STAT5A_E42_F | N |
| BCR_P346_F | Y | VAV1_P317_F | N |
| FZD9_P175_F | Y | DSG1_P159_R | N |
| HOXA9_P303_F | Y | FAS_P322_R | N |
| IPF1_P234_F | Y | SPP1_E140_F | N |
| DNAJC15_P65_F | Y | CHI3L2_E10_F | N |
| PALM2-AKAP2_P420_R | Y | PGR_P790_F | N |
| MDR1_seq_42_S300_R | Y | TNFSF8_P184_F | Y |
| PRKCDBP_E206_F | Y | TJP2_P518_F | Y |
| AHR_E103_F | Y | GSTM2_P453_R | N |
| RASSF1_E116_F | Y | ITK_P114_F | N |
| MYOD1_E156_F | Y | CPA4_E20_F | N |
| DSP_P36_F | Y | PI3_P1394_R | N |
| ISL1_E87_R | Y | MPO_E302_R | N |
| TAL1_E122_F | Y | ACVR1_P983_F | N |
| ICA1_P72_R | Y | GSTM2_P109_R | N |
| IGFBP1_P12_R | Y | LTB4R_E64_R | N |
| RARA_P176_R | N | CCR5_P630_R | N |
| DIO3_P90_F | Y | KRT1_P798_R | N |
| WRN_P969_F | Y | AOC3_P890_R | N |
| PENK_P447_R | Y | IL10_P85_F | N |
| TERT_P360_R | Y | SPI1_E205_F | Y |
| SOX17_P287_R | Y | IFNG_E293_F | N |
| SFRP1_P157_F | Y | | |
| WT1_P853_F | Y | | | or in Table 7B

| Glioma (hypermethylation) (n: 15) | CGI | Glioma (hypomethylation) (n: 29) | CGI |
|---|---|---|---|
| TES_P182_F | Y | IL8_E118_R | N |
| TNFRSF10A_P171_F | Y | CASP10_P334_F | N |
| TNFRSF10A_P91_F | Y | SERPINE1_P519_F | N |
| TES_E172_F | Y | MMP14_P13_F | Y |
| AHR_P166_R | Y | CASP10_P186_F | N |
| MEST_E150_F | Y | MMP9_P189_F | N |
| PCTK1_E77_R | Y | SH3BP2_E18_F | N |
| GFI1_P45_R | Y | GSTM2_E153_F | Y |
| MEST_P4_F | Y | CASP10_E139_F | N |
| DNAJC15_P65_F | Y | ALPL_P433_F | Y |
| AHR_E103_F | Y | RIPK3_P24_F | N |
| DSP_P36_F | Y | GFAP_P1214_F | N |
| TAL1_E122_F | Y | STAT5A_P704_R | N |
| ICA1_P72_R | Y | CD86_P3_F | N |
| WRN_P969_F | Y | TNFSF10_E53_F | N |
| | | FGFR2_P460_R | Y |
| | | SPDEF_P6_R | N |
| | | STAT5A_E42_F | N |
| | | VAV1_P317_F | N |
| | | FAS_P322_R | N |
| | | SPP1_E140_F | N |
| | | CHI3L2_E10_F | N |
| | | TJP2_P518_F | N |
| | | GSTM2_P453_R | N |
| | | ACVR1_P983_F | N |
| | | GSTM2_P109_R | N |
| | | LTB4R_E64_R | N |
| | | IL10_P85_F | N |
| | | SPI1_E205_F | Y | is compared with the methylation status of a glioma, wherein CGI is CpG island associated, Y is yes, and N is not.

11. The method according to claim 2, wherein detecting the methylation status comprises detecting the methylation status in one or more CpG sites as defined in Tables 8A and 8B, wherein the methylation status in one or more CpG sites as defined in Table 8A

| Ovarian cancer hypermethylation (n: 40) | CGI | Ovarian cancer hypomethylation (n: 16) | CGI |
|---|---|---|---|
| CFTR_P372_R | Y | MEST_P4_F | Y |
| HCK_P858_F | Y | PI3_E107_F | N |
| MOS_E60_R | Y | NBL1_P24_F | N |
| HOXA9_E252_R | Y | PTPN6_P282_R | N |
| TAL1_P594_F | Y | WEE1_P924_R | N |
| DIO3_P674_F | Y | S100A2_P1186_F | N |
| PENK_E26_F | Y | NID1_P677_F | N |
| SOX1_P294_F | Y | CTLA4_E176_R | N |
| LEFTY2_P561_F | N | GLI2_E90_F | N |
| CALCA_E174_R | Y | MST1R_E42_R | Y |
| THY1_P149_R | Y | GPATC3_P410_R | N |
| HOXA11_P698_F | Y | TRIM29_E189_F | Y |
| ALOX12_P223_R | Y | GLI2_P295_F | Y |
| DIO3_P90_F | Y | EMR3_E61_F | N |
| GLI3_P453_R | Y | MSH2_P1008_F | Y |
| ATP10A_P147_F | Y | IFNG_E293_F | N |
| ASCL1_P747_F | Y | | |
| MFAP4_P10_R | N | | |
| HS3ST2_E145_R | Y | | |
| ALOX12_E85_R | Y | | |
| DCC_E53_R | Y | | |
| HS3ST2_P171_F | Y | | |
| FRZB_E186_R | Y | | |
| THY1_P20_R | Y | | |
| TNFRSF10C_P7_F | Y | | |
| HOXA9_P303_F | Y | | |
| DDR2_P743_R | N | | |
| RASSF1_P244_F | Y | | |
| DBC1_P351_R | Y | | |
| MFAP4_P197_F | N | | |
| ZNF215_P71_R | Y | | |
| EPHA5_P66_F | Y | | |
| HCK_P46_R | Y | | |
| MMP2_P303_R | Y | | |
| CYP1B1_E83_R | Y | | |
| PITX2_E24_R | Y | | |
| ZNF215_P129_R | Y | | |

-continued

| Ovarian cancer hypermethylation (n: 40) | CGI | Ovarian cancer hypomethylation (n: 16) | CGI |
|---|---|---|---|
| TSP50_P137_F | Y | | |
| SEPT9_P374_F | Y | | |
| SEPT5_P441_F | Y | | | or in Table 8B

| Ovarian cancer* (n: 3) | CGI | Ovarian cancer* (n: 4) | CGI |
|---|---|---|---|
| GLI3_P453_R | Y | WEE1_P924_R | N |
| THY1_P20_R | Y | CTLA4_E176_R | N |
| DDR2_P743_R | N | GPATC3_P410_R | N |
| | | MSH2_P1008_F | Y | is compared with the methylation status of an ovarian cancer, wherein CGI is CpG island associated, Y is yes, and N is not.

12. The method according to claim 2, wherein detecting the methylation status comprises detecting the methylation status in one or more CpG sites as defined in Tables 9A and 9B, wherein the methylation status in one or more CpG sites as defined in Table 9A

| Lung cancer hypermethylation (n: 39) | CGI | Lung cancer hypomethylation (n: 1) | CGI |
|---|---|---|---|
| HOXA9_E252_R | Y | SPI1_P48_F | N |
| MOS_E60_R | Y | | |
| HS3ST2_E145_R | Y | | |
| EYA4_P794_F | Y | | |
| TAL1_P594_F | Y | | |
| STAT5A_E42_F | N | | |
| HOXA9_P1141_R | Y | | |
| TPEF_seq_44_S88_R | Y | | |
| FZD9_E458_F | Y | | |
| DIO3_P90_F | Y | | |
| FRZB_E186_R | Y | | |
| HCK_P858_F | Y | | |
| DLK1_E227_R | Y | | |
| JAK3_P156_R | N | | |
| NOTCH4_E4_F | N | | |
| ASCL2_P609_R | Y | | |
| HOXA11_P698_F | Y | | |
| SOX17_P287_R | Y | | |
| PENK_E26_F | Y | | |
| HS3ST2_P171_F | Y | | |
| HTR1B_E232_R | Y | | |
| GP1BB_P278_R | Y | | |
| SOX1_P294_F | Y | | |
| POMC_P400_R | Y | | |
| CFTR_P372_R | Y | | |
| FGF2_P229_F | Y | | |
| CDH13_P88_F | Y | | |
| RBP1_P426_R | Y | | |
| CALCA_E174_R | Y | | |
| CSPG2_P82_R | Y | | |
| APC_P14_F | Y | | |
| ZNF215_P71_R | Y | | |
| CHGA_E52_F | Y | | |
| HOXB13_P17_R | Y | | |
| COL1A2_E299_F | Y | | |
| TJP2_P518_F | Y | | |

-continued

| Lung cancer hypermethylation (n: 39) | CGI | Lung cancer hypomethylation (n: 1) | CGI |
|---|---|---|---|
| GAS7_E148_F | Y | | |
| TBX1_P885_R | Y | | |
| GSTM2_E153_F | Y | | | or in Table 9B

| Lung cancer* (n: 2) | CGI | Lung cancer* (n: 1) | CGI |
|---|---|---|---|
| JAK3_P156_R | N | SPI1_P48_F | N |
| GP1BB_P278_R | Y | | | is compared with the methylation status of a lung cancer, wherein CGI is CpG island associated, Y is yes, and N is not.

13. The method according to claim 2, wherein detecting the methylation status comprises detecting the methylation status in one or more CpG sites as defined in Tables 10A and 10B, wherein the methylation status in one or more CpG sites as defined in Table 10A

| Bladder cancer hypermethylation (n: 36) | CGI | Bladder cancer hypomethylation (n: 80) | CGI |
|---|---|---|---|
| HOXA9_E252_R | Y | TRIM29_P261_F | N |
| HOXA11_P698_F | Y | PI3_E107_F | N |
| TJP2_P330_R | Y | CEACAM1_P44_R | N |
| TJP2_P518_F | Y | IFNG_E293_F | N |
| PENK_E26_F | Y | NOS2A_E117_R | N |
| CYP1B1_P83_R | Y | NOS3_P38_F | N |
| WT1_P853_F | Y | PSCA_P135_F | N |
| TAL1_P594_F | Y | PTPRH_P255_F | N |
| DLK1_E227_R | Y | TMPRSS4_E83_F | N |
| SLIT2_P208_F | Y | SRC_E100_R | N |
| HOXA9_P303_F | Y | CDH17_P376_F | N |
| FLT3_E326_R | Y | AATK_E63_R | N |
| SOX17_P287_R | Y | THBS2_P605_R | N |
| PENK_P447_R | Y | CDH17_E31_F | N |
| NPY_E31_R | Y | KRT5_E196_R | Y |
| NPY_P295_F | Y | P2RX7_P597_F | N |
| SOX1_P294_F | Y | IL1RN_E42_F | N |
| CDH11_P354_R | Y | AIM2_P624_F | N |
| TPEF_seq_44_S88_R | Y | NBL1_P24_F | N |
| MYOD1_E156_F | Y | PI3_P274_R | N |
| HOXA11_E35_F | Y | NID1_P677_F | N |
| LEFTY2_P561_F | N | SERPINB5_P19_R | Y |
| GSTM1_P266_F | Y | S100A2_P1186_F | N |
| SLIT2_E111_R | Y | SLC14A1_E295_F | N |
| HS3ST2_E145_R | Y | CLDN4_P1120_R | N |
| GSTM1_P363_F | Y | EMR3_E61_F | N |
| TERT_P360_R | Y | PTPRH_E173_F | N |
| HS3ST2_P171_F | Y | BCR_P422_F | Y |
| PITX2_E24_R | Y | TRIM29_P135_F | N |
| TERT_E20_F | Y | EMR3_P39_R | N |
| NPR2_P618_F | Y | VAMP8_P114_F | N |
| NEFL_P209_R | Y | MST1R_E42_R | Y |
| ISL1_P554_F | Y | PTPN6_P282_R | N |
| TWIST1_P355_R | Y | TRPM5_P979_F | N |
| HIC-1_seq_48_S103_R | Y | IGFBP1_P12_R | Y |
| SOX1_P1018_R | Y | VAMP8_E7_F | N |
| | | SFN_E118_F | Y |
| | | TFF2_P178_F | N |
| | | IGFBP1_E48_R | Y |
| | | EDNRB_P709_R | N |
| | | GPR116_E328_R | N |
| | | CXCL9_E268_R | N |
| | | VAMP8_P241_F | N |
| | | UGT1A1_P315_R | N |
| | | PGR_P790_F | N |
| | | GLI2_P295_F | Y |
| | | CASP8_E474_F | N |

-continued

| Bladder cancer hypermethylation (n: 36) | CGI | Bladder cancer hypomethylation (n: 80) | CGI |
|---|---|---|---|
| | | GABRA5_P862_R | N |
| | | TRIP6_P1090_F | Y |
| | | AIM2_E208_F | N |
| | | NID1_P714_R | N |
| | | HDAC1_P414_R | Y |
| | | TIMP1_P615_R | N |
| | | BRCA1_P835_R | Y |
| | | PTK6_E50_F | Y |
| | | ARHGDIB_P148_R | N |
| | | PRSS8_E134_R | Y |
| | | VAV1_E9_F | Y |
| | | KRT13_P341_R | N |
| | | OSM_P188_F | Y |
| | | GABRA5_P1016_F | N |
| | | RIPK3_P124_F | N |
| | | TRIM29_E189_F | Y |
| | | CSF1R_E26_F | N |
| | | JAK3_P1075_R | N |
| | | NBL1_E205_R | N |
| | | LCN2_P86_R | N |
| | | MMP19_E274_R | N |
| | | GLI2_E90_F | N |
| | | ZP3_P220_F | N |
| | | MMP10_E136_R | N |
| | | HPN_P823_F | N |
| | | AFF3_P122_F | N |
| | | SRC_P164_F | N |
| | | PADI4_E24_F | N |
| | | CAPG_E228_F | N |
| | | MAPK10_E26_F | N |
| | | SFTPA1_E340_R | N |
| | | PSCA_E359_F | N |
| | | APBA2_P305_R | N | or in Table 10B

| Bladder cancer (hypermethylation) (n: 2) | CGI | Bladder cancer (hypomethylation) (n: 27) | CGI |
|---|---|---|---|
| TERT_E20_F | Y | TMPRSS4_E83_F | N |
| NPR2_P618_F | Y | SRC_E100_R | N |
| | | CDH17_P376_F | N |
| | | THBS2_P605_R | N |
| | | CDH17_E31_F | N |
| | | KRT5_E196_R | Y |
| | | P2RX7_P597_F | N |
| | | AIM2_P624_F | N |
| | | SLC14A1_E295_F | N |
| | | BCR_P422_F | Y |
| | | VAMP8_P114_F | N |
| | | TRPM5_P979_F | N |
| | | IGFBP1_P12_R | Y |
| | | VAMP8_E7_F | N |
| | | IGFBP1_E48_R | Y |
| | | EDNRB_P709_R | N |
| | | GPR116_E328_R | N |
| | | NID1_P714_R | N |
| | | TIMP1_P615_R | N |
| | | ARHGDIB_P148_R | N |
| | | KRT13_P341_R | N |
| | | GABRA5_P1016_F | N |
| | | CSF1R_E26_F | N |
| | | MMP19_E274_R | N |
| | | HPN_P823_F | N |
| | | PADI4_E24_F | N |
| | | MAPK10_E26_F | N | is compared with the methylation status of a bladder cancer, wherein CGI is island associated, Y is yes, and N is not.

14. The method according to claim 2, wherein detecting the methylation status comprises detecting the methylation status in one or more CpG sites as defined in Tables 11A and 11B, wherein the methylation status in one or more CpG sites as defined in Table 11A

| Melanoma hypermethylation (n: 28) | CGI | Melanoma hypomethylation (n: 5) | CGI |
|---|---|---|---|
| ALOX12_P223_R | Y | EVI2A_P94_R | N |
| ALOX12_E85_R | Y | IFNG_E293_F | N |
| MET_E333_F | Y | PI3_P1394_R | N |
| SNCG_E119_F | N | TNFSF8_P184_F | Y |
| GRB7_E71_R | N | VAV1_E9_F | Y |
| AATK_P709_R | Y | | |
| DDR1_P332_R | N | | |
| DHCR24_P652_R | N | | |
| SNCG_P53_F | Y | | |
| RARA_P176_R | N | | |
| IL1RN_P93_R | N | | |
| TGFB3_E58_R | N | | |
| TNFRSF10D_E27_F | Y | | |
| STAT5A_P704_R | N | | |
| COL1A2_P407_R | N | | |
| POMC_P400_R | Y | | |
| IGFBP5_P9_R | Y | | |
| SNCG_P98_R | Y | | |
| BMP4_P123_R | Y | | |
| CYP1B1_E83_R | Y | | |
| KCNK4_E3_F | Y | | |
| IL17RB_P788_R | Y | | |
| IL6_E168_F | N | | |
| BMP4_P199_R | Y | | |
| S100A2_P1186_F | N | | |
| FRZB_E186_R | Y | | |
| TRIP6_P1090_F | Y | | |
| LCN2_P86_R | N | | | or in Table 11B

| Melanoma (hypermethylation) (n: 4) | CGI | Melanoma (hypermethylation) (n: 1) | CGI |
|---|---|---|---|
| MET_E333_F | Y | EVI2A_P94_R | N |
| COL1A2_P407_R | N | | |
| IL17RB_P788_R | Y | | |
| IL6_E168_F | N | | | is compared with the methylation status of a melanoma, wherein CGI is CpG island associated, Y is yes, and N is not.

15. The method according to claim 2, wherein detecting the methylation status comprises detecting the methylation status in one or more CpG sites as defined in Table 12A, wherein the methylation status in one or more CpG sites as defined in Table 12A

| Breast cancer (hypomethylation) (n: 18) | CGI | Breast cancer (hypomethylation) (n: 1) | CGI |
|---|---|---|---|
| CFTR_P372_R | Y | PI3_E107_F | N |
| HOXA9_E252_R | Y | | |
| RBP1_P426_R | Y | | |
| TNFRSF10D_E27_F | Y | | |
| MME_E29_F | Y | | |
| TSP50_P137_F | Y | | |
| TERT_P360_R | Y | | |
| APC_P14_F | Y | | |
| GSTP1_E322_R | Y | | |
| RASSF1_E116_F | Y | | |
| SOX1_P294_F | Y | | |
| SOX17_P287_R | Y | | |
| MOS_E60_R | Y | | |
| CDH13_P88_F | Y | | |
| APC_E117_R | Y | | |

| Breast cancer (hypomethylation) (n: 18) | CGI | Breast cancer (hypomethylation) (n: 1) | CGI |
|---|---|---|---|
| BMP4_P123_R | Y | | |
| IRAK3_P185_F | Y | | |
| IGFBP3_P423_R | Y | | | is compared with the methylation status of a breast cancer, wherein CGI is CpG island associated, Y is yes, and N is not.

16. The method according to claim 2, wherein detecting the methylation status comprises detecting the methylation status in one or more CpG sites as defined in Tables 14A and 14B, wherein the methylation status in one or more CpG sites as defined in Table 14A

| Testicular cancer hypermethylation (n: 10) | CGI |
|---|---|
| BCR_P346_F | Y |
| SEPT5_P464_R | Y |
| GSTM1_P363_F | Y |
| IPF1_P750_F | Y |
| BCR_P422_F | Y |
| HOXA5_E187_F | Y |
| TBX1_P520_F | N |
| HIC-1_seq_48_S103_R | Y |
| ARHGDIB_P148_R | N |
| GPATC3_P410_R | N | or in Table 14B

| Testis cancer (hypermethylation) (n: 2) | CGI | Testis cancer (hypomethylation) (n: 1) | CGI |
|---|---|---|---|
| TBX1_P520_F | N | H19_P1411_R | Y |
| GPATC3_P410_R | N | | | is compared with the methylation status of a testicular cancer, wherein CGI is CpG island associated, Y is yes, and N is not.

17. The method according to claim 2, wherein detecting the methylation status comprises detecting the methylation status in one or more CpG sites as defined in Tables 15A and 15B, wherein the methylation status in one or more CpG sites as defined in Table 15A

| Stomach cancer hypermethylation (n: 7) | CGI | Stomach cancer hypomethylation (n: 2) | CGI |
|---|---|---|---|
| GAS7_E148_F | Y | TNFSF8_P184_F | Y |
| TGFB3_E58_R | N | CSF3R_P8_F | N |
| SFRP1_P157_F | Y | | |
| SOX1_P294_F | Y | | |
| MDR1_seq_42_S300_R | Y | | |
| HS3ST2_E145_R | Y | | |
| CCKAR_P270_F | N | | | or in Table 15B

| Stomach cancer (hypermethylation) (n: 1) | CGI |
|---|---|
| CCKAR_P270_F | N | is compared with the methylation status of a stomach cancer, wherein CGI is CpG island associated, Y is yes, and N is not.

18. The method according to claim 1, wherein the the primary tumor is lymphoid neoplasia and the therapy targeted to said lymphoid neoplasia is a CD20-targeted drug selected from the group consisting of rituximab, ocrelizumab, PRO70769, rhuH27, ofatumumab, veltuzumab, hA20, IMMU-106, AME-133, LY2469298, PRO131921, GA-101, tositumomab and R05072759.

19. The method according to claim 1, wherein the primary tumor is pancreatic cancer and the therapy targeted to said pancreatic cancer is an antimetabolite selected from the group consisting of aminopterin, denopterin, methotrexate, edatrexate, trimetrexate, nolatrexed, lometrexol, pemetrexed, raltitrexed, piritrexim, pteropterin, leucovorin, 10-propargyl-5,8-dideazafolate, cladribine, clofarabine, fludarabine, mercaptopurine, pentostatin, thioguanine, capecitabine, cytarabine, decitabine, fluorouracil, 5-fluorouracil, doxifluridine, floxuridine and gemcitabine.

* * * * *

UNITED STATES PATENT AND TRADEMARK OFFICE
CERTIFICATE OF CORRECTION

PATENT NO. : 10,233,503 B2
APPLICATION NO. : 14/402736
DATED : March 19, 2019
INVENTOR(S) : Manel Esteller Badosa Page 1 of 1

It is certified that error appears in the above-identified patent and that said Letters Patent is hereby corrected as shown below:

On the Title Page

Item (73), Assignee should read:
FUNDACIÓ INSTITUT D'INVESTIGACIÓ BIOMÈDICA DE BELLVITGE (IDIBELL), Barcelona (ES)
FUNDACIÓ INSTITUCIÓ CATALANA DE RECERCA I ESTUDIS AVANÇATS, Barcelona (ES)

Signed and Sealed this
Seventh Day of April, 2020

Andrei Iancu
*Director of the United States Patent and Trademark Office*